United States Patent
Dipoto et al.

(10) Patent No.: US 11,849,931 B2
(45) Date of Patent: Dec. 26, 2023

(54) METHODS AND APPARATUS FOR ACCESS TO AND/OR TREATMENT OF THE SPINE

(71) Applicant: Zimmer Spine, Inc., Edina, MN (US)

(72) Inventors: Gene P Dipoto, Upton, MA (US); Stephen J Anderson, Hopkinton, MA (US); Alan E. Shluzas, Redwood City, CA (US)

(73) Assignee: Zimmer Biomet Spine, Inc., Edina, MN (US)

( * ) Notice: Subject to any disclaimer, the term of this patent is extended or adjusted under 35 U.S.C. 154(b) by 286 days.

(21) Appl. No.: 17/135,740

(22) Filed: Dec. 28, 2020

(65) Prior Publication Data
US 2021/0113201 A1      Apr. 22, 2021

Related U.S. Application Data

(63) Continuation of application No. 16/122,668, filed on Sep. 5, 2018, now Pat. No. 10,905,407, which is a
(Continued)

(51) Int. Cl.
*A61B 17/70* (2006.01)
*A61B 17/88* (2006.01)
(Continued)

(52) U.S. Cl.
CPC ........ *A61B 17/02* (2013.01); *A61B 17/06109* (2013.01); *A61B 17/3439* (2013.01);
(Continued)

(58) Field of Classification Search
CPC .............. A61B 17/02; A61B 17/06109; A61B 17/3439; A61B 17/7002; A61B 17/7032;
(Continued)

(56) References Cited

U.S. PATENT DOCUMENTS

| 2,541,516 A | 2/1951 | Ivory et al. |
| 5,125,396 A | 6/1992 | Ray |

(Continued)

FOREIGN PATENT DOCUMENTS

| CA | 2555868 A1 * | 10/2005 | ......... A61B 17/7088 |
| CA | 2587478 A1 * | 5/2006 | ......... A61B 17/7088 |

(Continued)

OTHER PUBLICATIONS

"U.S. Appl. No. 11/760,551, Non Final Office Action dated Apr. 30, 2009", 13 pgs.

(Continued)

*Primary Examiner* — Eduardo C Robert
*Assistant Examiner* — David C Comstock
(74) *Attorney, Agent, or Firm* — Sheridan Ross P.C.

(57) ABSTRACT

Systems, devices, and methods suitable for use with procedures performed at least partially percutaneously are provided. In some procedures, two or more access devices for providing access to adjacent surgical locations within a patient are used. Certain embodiments of the access device comprise an elongate body having a distal end with one or more cutouts. The cutouts on adjacent access devices are generally aligned with each other to permit passage of a portion of a fixation element from one access device to the other access device. A fastener with an elongated removable head may be delivered to the surgical site through the access device. After a distal end of the fastener is secured to the surgical site, a portion of the elongated housing is detached from the remainder of the fastener and removed from the patient.

20 Claims, 47 Drawing Sheets

Related U.S. Application Data continuation of application No. 14/727,142, filed on Jun. 1, 2015, now Pat. No. 10,085,732, which is a continuation of application No. 11/760,551, filed on Jun. 8, 2007, now Pat. No. 9,055,934.

(60) Provisional application No. 60/812,703, filed on Jun. 9, 2006.

(51) Int. Cl.
*A61B 17/02* (2006.01)
*A61B 17/06* (2006.01)
*A61B 17/34* (2006.01)
*A61B 17/04* (2006.01)

(52) U.S. Cl.
CPC ........ *A61B 17/7002* (2013.01); *A61B 17/708* (2013.01); *A61B 17/7032* (2013.01); *A61B 17/7035* (2013.01); *A61B 17/7082* (2013.01); *A61B 17/7083* (2013.01); *A61B 17/7085* (2013.01); *A61B 17/7091* (2013.01); *A61B 17/8863* (2013.01); *A61B 17/0218* (2013.01); *A61B 17/0482* (2013.01); *A61B 17/0483* (2013.01); *A61B 17/3421* (2013.01); *A61B 2017/0256* (2013.01); *A61B 2017/3443* (2013.01)

(58) Field of Classification Search
CPC .............. A61B 17/7035; A61B 17/708; A61B 17/7082; A61B 17/7083; A61B 17/7085; A61B 17/7091; A61B 17/8863; A61B 17/0218; A61B 17/0482; A61B 17/0483; A61B 17/3421; A61B 2017/0256; A61B 2017/3443
USPC ......... 606/606, 265, 279, 305, 308, 99, 104, 606/86 A
See application file for complete search history.

(56) References Cited

U.S. PATENT DOCUMENTS

| | | | |
|---|---|---|---|
| 5,158,543 A | 10/1992 | Lazarus | |
| 5,292,309 A | 3/1994 | Van Tassel et al. | |
| 5,531,751 A | 7/1996 | Schultheiss et al. | |
| 5,618,290 A | 4/1997 | Toy et al. | |
| 5,667,520 A | 9/1997 | Bonutti | |
| 5,755,728 A | 5/1998 | Maki | |
| 5,882,340 A | 3/1999 | Yoon | |
| 6,171,299 B1 | 1/2001 | Bonutti | |
| 6,361,488 B1 | 3/2002 | Davison et al. | |
| 6,423,071 B1 | 7/2002 | Lawson | |
| 6,530,880 B2 | 3/2003 | Pagliuca | |
| 6,554,832 B2 | 4/2003 | Shluzas | |
| 6,641,583 B2 | 11/2003 | Shluzas et al. | |
| 6,648,888 B1 | 11/2003 | Shluzas | |
| 6,652,553 B2 | 11/2003 | Davison et al. | |
| 6,673,074 B2 | 1/2004 | Shluzas | |
| 6,821,243 B2 | 11/2004 | Pagliuca et al. | |
| 6,821,277 B2 | 11/2004 | Teitelbaum | |
| 6,837,889 B2 | 1/2005 | Shluzas | |
| 6,945,933 B2 | 9/2005 | Branch et al. | |
| 6,945,974 B2 | 9/2005 | Dalton | |
| 6,969,392 B2 | 11/2005 | Gitis et al. | |
| 7,004,947 B2 | 2/2006 | Shluzas et al. | |
| 7,008,422 B2 | 3/2006 | Foley et al. | |
| 7,008,424 B2 | 3/2006 | Teitelbaum | |
| 7,014,608 B2 | 3/2006 | Larson et al. | |
| 7,056,321 B2 | 6/2006 | Pagliuca et al. | |
| 7,066,937 B2 | 6/2006 | Shluzas | |
| 7,118,576 B2 | 10/2006 | Gitis et al. | |
| 7,144,393 B2 | 12/2006 | DiPoto et al. | |
| 7,179,225 B2 | 2/2007 | Shluzas et al. | |
| 7,226,451 B2 | 6/2007 | Shluzas et al. | |
| 7,261,688 B2 | 8/2007 | Smith et al. | |
| 7,462,182 B2 * | 12/2008 | Lim ................... | A61B 17/7086 606/99 |
| 7,695,475 B2 | 4/2010 | Justis et al. | |
| 7,794,464 B2 | 9/2010 | Bridwell et al. | |
| 7,811,288 B2 | 10/2010 | Jones et al. | |
| 7,892,238 B2 | 2/2011 | DiPoto et al. | |
| 7,918,792 B2 | 4/2011 | Drzyzga et al. | |
| 8,075,591 B2 | 12/2011 | Ludwig et al. | |
| 8,123,751 B2 | 2/2012 | Shluzas | |
| 8,956,361 B2 | 2/2015 | Davenport et al. | |
| 9,055,934 B2 | 6/2015 | DiPoto et al. | |
| 9,173,687 B2 | 11/2015 | Fowler et al. | |
| 10,085,732 B2 | 10/2018 | Dipoto et al. | |
| 2002/0082523 A1 | 6/2002 | Kinsella et al. | |
| 2002/0161368 A1 | 10/2002 | Foley et al. | |
| 2003/0060826 A1 | 3/2003 | Foley et al. | |
| 2003/0073998 A1 | 4/2003 | Pagliuca et al. | |
| 2003/0187453 A1 | 10/2003 | Schiapfer et al. | |
| 2003/0191371 A1 | 10/2003 | Smith et al. | |
| 2003/0199873 A1 | 10/2003 | Richelsoph | |
| 2004/0006344 A1 | 1/2004 | Nguyen et al. | |
| 2004/0039384 A1 | 2/2004 | Boehm, Jr. et al. | |
| 2004/0133201 A1 | 7/2004 | Shluzas et al. | |
| 2004/0138662 A1 | 7/2004 | Landry et al. | |
| 2004/0143265 A1 | 7/2004 | Landry et al. | |
| 2004/0176665 A1 | 9/2004 | Branch et al. | |
| 2004/0215190 A1 | 10/2004 | Nguyen et al. | |
| 2004/0215193 A1 | 10/2004 | Shaolian et al. | |
| 2004/0002301 A1 | 11/2004 | Shluzas | |
| 2005/0021030 A1 | 1/2005 | Pagliuca et al. | |
| 2005/0043742 A1 | 2/2005 | Bruneau et al. | |
| 2005/0065515 A1 | 3/2005 | Jahng | |
| 2005/0065517 A1 | 3/2005 | Chin | |
| 2005/0075644 A1 | 4/2005 | Dipoto et al. | |
| 2005/0080418 A1 | 4/2005 | Simonson et al. | |
| 2005/0085813 A1 | 4/2005 | Spitler | |
| 2005/0090822 A1 | 4/2005 | Dipoto | |
| 2005/0090833 A1 | 4/2005 | Dipoto | |
| 2005/0090899 A1 | 4/2005 | Dipoto et al. | |
| 2005/0107789 A1 | 5/2005 | Sweeney | |
| 2005/0131408 A1 | 6/2005 | Sicvol et al. | |
| 2005/0131421 A1 | 6/2005 | Anderson et al. | |
| 2005/0154389 A1 | 7/2005 | Selover et al. | |
| 2005/0159651 A1 | 7/2005 | Raymond et al. | |
| 2005/0159756 A1 | 7/2005 | Ray | |
| 2005/0171540 A1 | 8/2005 | Lim et al. | |
| 2005/0192570 A1 | 9/2005 | Jackson | |
| 2005/0192579 A1 | 9/2005 | Jackson | |
| 2005/0215999 A1 | 9/2005 | Birkmeyer et al. | |
| 2005/0234304 A1 | 10/2005 | Dewey et al. | |
| 2005/0234449 A1 | 10/2005 | Aferzon | |
| 2005/0245928 A1 | 11/2005 | Colleran et al. | |
| 2005/0245942 A1 | 11/2005 | Dipoto | |
| 2005/0251139 A1 | 11/2005 | Roh | |
| 2005/0251192 A1 | 11/2005 | Shluzas et al. | |
| 2005/0273101 A1 | 12/2005 | Schumacher | |
| 2005/0273131 A1 | 12/2005 | Shluzas et al. | |
| 2005/0273132 A1 | 12/2005 | Shluzas et al. | |
| 2005/0273133 A1 | 12/2005 | Shluzas et al. | |
| 2005/0277812 A1 | 12/2005 | Myles | |
| 2005/0277934 A1 | 12/2005 | Vardiman | |
| 2005/0283171 A1 | 12/2005 | Bellafiore et al. | |
| 2006/0009777 A1 | 1/2006 | Lim et al. | |
| 2006/0030850 A1 | 2/2006 | Keegan et al. | |
| 2006/0036252 A1 | 2/2006 | Baynham et al. | |
| 2006/0036255 A1 | 2/2006 | Pond, Jr. et al. | |
| 2006/0058794 A1 | 3/2006 | Jackson | |
| 2006/0069391 A1 | 3/2006 | Jackson | |
| 2006/0069404 A1 | 3/2006 | Shluzas et al. | |
| 2006/0084980 A1 | 4/2006 | Melkent et al. | |
| 2006/0106416 A1 | 5/2006 | Raymond et al. | |
| 2006/0106934 A1 | 5/2006 | Figaro et al. | |
| 2006/0111712 A1 | 5/2006 | Jackson | |
| 2006/0111713 A1 | 5/2006 | Jackson | |
| 2006/0206008 A1 | 9/2006 | Daiton | |
| 2006/0217735 A1 | 9/2006 | MacDonald et al. | |
| 2006/0229636 A1 | 10/2006 | Woodburn et al. | |

(56) References Cited

U.S. PATENT DOCUMENTS

| | | |
|---|---|---|
| 2006/0247630 A1 | 11/2006 | Iott et al. |
| 2006/0264962 A1 | 11/2006 | Chin et al. |
| 2006/0271057 A1 | 11/2006 | Shluzas et al. |
| 2006/0276791 A1 | 12/2006 | Shluzas |
| 2006/0287584 A1* | 12/2006 | Garcia-Bengochia ............ A61B 17/02 600/213 |
| 2006/0293693 A1 | 12/2006 | Farr et al. |
| 2007/0005077 A1* | 1/2007 | Null .................. A61B 17/8883 606/104 |
| 2007/0088357 A1 | 4/2007 | Johnson. et al. |
| 2007/0106123 A1 | 5/2007 | Gorek et al. |
| 2007/0191840 A1 | 8/2007 | Pond, Jr. et al. |
| 2007/0213715 A1 | 9/2007 | Bridwell et al. |
| 2007/0213716 A1* | 9/2007 | Lenke ................ A61B 17/7032 606/264 |
| 2007/0288026 A1 | 12/2007 | Shluzas |
| 2007/0299443 A1 | 12/2007 | Dipoto et al. |
| 2007/0299444 A1 | 12/2007 | Dipoto et al. |
| 2008/0015582 A1 | 1/2008 | Dipoto et al. |
| 2008/0039839 A1 | 2/2008 | Songer et al. |
| 2008/0065114 A1 | 3/2008 | Stone et al. |
| 2008/0077155 A1 | 3/2008 | Diederich |
| 2008/0082103 A1 | 4/2008 | Hutton et al. |
| 2008/0114403 A1 | 5/2008 | Kuester et al. |
| 2008/0119849 A1 | 5/2008 | Beardsley et al. |
| 2008/0125788 A1 | 5/2008 | Cohen et al. |
| 2008/0183214 A1 | 7/2008 | Copp et al. |
| 2008/0262318 A1 | 10/2008 | Gorek et al. |
| 2008/0300638 A1 | 12/2008 | Beardsley et al. |
| 2010/0004695 A1 | 1/2010 | Stad et al. |
| 2010/0036443 A1 | 2/2010 | Hutton et al. |
| 2010/0331901 A1 | 12/2010 | Iott et al. |
| 2014/0277168 A1 | 9/2014 | Hutton et al. |
| 2015/0320457 A1 | 11/2015 | Dipoto et al. |
| 2019/0000437 A1 | 1/2019 | Dipoto et al. |

FOREIGN PATENT DOCUMENTS

| | | | |
|---|---|---|---|
| EP | 2043528 | | 4/2009 |
| EP | 2529668 A1 | | 12/2012 |
| EP | 2529668 | | 8/2014 |
| FR | 2827758 A1 * | 1/2003 | ......... A61B 17/7088 |
| WO | WO-2004041100 A1 | | 5/2004 |
| WO | WO-2004103188 | | 12/2004 |
| WO | WO-2004103188 A2 | | 12/2004 |
| WO | WO-2005018466 | | 3/2005 |
| WO | WO-2005018466 A2 | | 3/2005 |
| WO | WO-2005041863 | | 5/2005 |
| WO | WO-2005041863 A2 | | 5/2005 |
| WO | WO-2005046492 A1 | | 5/2005 |
| WO | WO-2005096968 A1 | | 10/2005 |
| WO | WO-2007146833 | | 12/2007 |
| WO | WO-2007146833 A3 | | 3/2008 |

OTHER PUBLICATIONS

"U.S. Appl. No. 11/760,551, Advisory Action dated Jan. 13, 2010", 3 pgs.
"U.S. Appl. No. 11/760,551, Final Office Action dated Jun. 1, 2012", 14 pgs.
"U.S. Appl. No. 11/760,551, Final Office Action dated Nov. 5, 2009", 14 pgs.
"U.S. Appl. No. 11/760,551, Final Office Action dated Dec. 26, 2014", 7 pgs.
"U.S. Appl. No. 11/760,551, Non Final Office Action dated Apr. 30, 2009", 10 pgs.
"U.S. Appl. No. 11/760,551, Non Final Office Action dated Jun. 18, 2014", 10 pgs.
"U.S. Appl. No. 11/780,551, Non Final Office Action dated Nov. 9, 2011", 13 pgs.
"U.S. Appl. No. 11/760,551, Notice of Allowance dated Feb. 10, 2015", 5 pgs.
"U.S. Appl. No. 11/760,551, Response filed Jan. 4, 2010 to Final Office Action dated Nov. 5, 2009", 8 pgs.
"U.S. Appl. No. 11/760,551, Response filed Jan. 30, 2015 to Final Office Action dated Dec. 26, 2014", 4 pgs.
"U.S. Appl. No. 11/760,551, Response filed Feb. 5, 2010 to Advisory Action dated Jan. 13, 2010", 10 pgs.
"U.S. Appl. No. 11/780,551, Response filed Feb. 8, 2012 to Non Final Office Action dated Nov. 9, 2011", 8 pgs.
"U.S. Appl. No. 11/760,551, Response filed Jul. 27, 2009 to Non Final Office Action dated Apr. 30, 2009", 7 pgs.
"U.S. Appl. No. 11/760,551, Response filed Sep. 4, 2012 to Final Office Action dated Jun. 1, 2012", 6 pgs.
"U.S. Appl. No. 11/760,551, Response filed Sep. 16, 2014 to Non Final Office Action dated Jun. 18, 2014", 6 pgs.
"U.S. Appl. No. 11/780,558, Advisory Action dated Apr. 25, 2011", 3 pgs.
"U.S. Appl. No. 11/760,558, Final Office Action dated Jan. 11, 2011", 9 pgs.
"U.S. Appl. No. 11/760,558, Non Final Office Action dated Aug. 2, 2010", 12 pgs.
"U.S. Appl. No. 11/760,558, Notice of Allowance dated Oct. 27, 2011", 7 pgs.
"U.S. Appl. No. 11/760,558, Response filed Apr. 11, 2011 to Final Office Action dated Jan. 11, 2011", 7 pgs.
"U.S. Appl. No. 11/760,558, Response filed Nov. 2, 2010 to Non Final Office Action dated Aug. 2, 2010", 9 pgs.
"U.S. Appl. No. 11/760,569, Advisory Action dated Jul. 29, 2010", 3 pgs.
"U.S. Appl. No. 11/760,569, Appeal Decision mailed Oct. 6, 2010", 2 pgs.
"U.S. Appl. No. 11/760,569, Final Office Action dated May 17, 2010", 10 pgs.
"U.S. Appl. No. 11/760,569, Non Final Office Action dated Apr. 30, 2009", 12 pgs.
"U.S. Appl. No. 11/780,569, Non Final Office Action dated Nov. 17, 2009", 9 pgs.
"U.S. Appl. No. 11/760,569, Notice of Allowance dated Oct. 27, 2010", 8 pgs.
"U.S. Appl. No. 11/760,569, Response filed Feb. 17, 2010 to Non Final Office Action dated Nov. 17, 2009", 8 pgs.
"U.S. Appl. No. 11/780,569, Response filed Jul. 16, 2010 to Final Office Action dated May 17, 2010", 9 pgs.
"U.S. Appl. No. 11/760,569, Response filed Jul. 27, 2009 to Non Final Office Action dated Apr. 30, 2009", 7 pgs.
"U.S. Appl. No. 14/727,142, Examiner Interview Summary dated Feb. 7, 2018", 4 pgs.
"U.S. Appl. No. 14/727,142, Final Office Action dated May 11, 2017", 13 pgs.
"U.S. Appl. No. 14/727,142, Non Final Office Action dated Jul. 15, 2016", 14 pgs.
"U.S. Appl. No. 14/727,142, Non Final Office Action dated Nov. 8, 2017", 12 pgs.
"U.S. Appl. No. 14/727,142, Notice of Allowance dated May 29, 2018", 10 pgs.
"U.S. Appl. No. 14/727,142, Response Filed Mar. 7, 2013 to Non-Final Office Action dated Nov. 8, 2017", 9 pgs.
"U.S. Appl. No. 14/727,142, Response Filed Jun. 27, 2016 to Restriction Requirement dated May 5, 2016", 7 pgs.
"U.S. Appl. No. 14/727,142, Response filed Aug. 11, 2017 to Final Office Action dated May 11, 2017", 10 pgs.
"U.S. Appl. No. 14/727,142, Response filed Dec. 14, 2016 to Non Final Office Action dated Jul. 15, 2016", 11 pgs.
"U.S. Appl. No. 14/727,142, Restriction Requirement dated May 5, 2016", 7 pgs.
"U.S. Appl. No. 16/122,668, Non Final Office Action dated Mar. 16, 2020", 19 pgs.
"U.S. Appl. No. 16/122,668, Notice of Allowance dated Sep. 24, 2020", 7 pgs.
"U.S. Appl. No. 16/122,668, Response filed Jun. 15, 2020 to Non Final Office Action dated Mar. 16, 2020", 8 pgs.
"Attached", Oxford University Press, [Online]. Retrieved from the Internet: <http://www.oxforddictionaries.com/definition/attached?view=uk>, (2010).

(56) References Cited

OTHER PUBLICATIONS

"European Application Serial No. 07784378.7, Communication Pursuant to Article 94(3) EPC dated Jun. 5, 2012", 4 pgs.
"European Application Serial No. 07784378.7, Communication Pursuant to Article 94(3) EPC dated Aug. 26, 2010", 4 pgs.
"European Application Serial No. 07784378.7, Response filed Mar. 7, 2011 to Communication Pursuant to Article 94(3) EPC dated Aug. 26, 2010", 16 pgs.
"European Application Serial No. 12182380.1, Communication Pursuant to Article 94(3) EPC dated Oct. 1, 2013", 5 pgs.
"European Application Serial No. 12182380.1, Extended European Search Report dated Oct. 10, 2012", 5 pgs.
"European Application Serial No. 12182380.1, Intention to Grant dated Mar. 24, 2014", 43 pgs.
"European Application Serial No. 12182380.1, Response filed Feb. 11, 2014 to Communication Pursuant to Article 94(3) EPC dated Oct. 1, 2013", 10 pgs.
"European Application Serial No. 12182380.1, Response filed Jun. 5, 2013 to Extended European Search Report dated Oct. 10, 2012", 11 pgs.
"International Application Serial No. PCT/US2007/070798, International Preliminary Report on Patentability dated Dec. 10, 2008", 8 pgs.
"International Application Serial No. PCT/US2007/070798, International Search Report dated Jan. 10, 2008", 5 pgs.
"International Application Serial No. PCT/US2007/070798, Written Opinion dated Jan. 10, 2008", 8 pgs.
"Viper 2 System Guide", DePuy Spine, (May 2008).
U.S. Appl. No. 11/760,551 U.S. Pat. No. 9,055,934, filed Jun. 8, 2007, Methods and Apparatus for Access to and/or Treatment of the Spine.
U.S. Appl. No. 14/727,142 U.S. Pat. No. 10,085,732, filed Jun. 1, 2015, Methods and Apparatus for Access to and/or Treatment of the Spine.
U.S. Appl. No. 11/760,537, filed Jun. 8, 2007, Methods and Apparatus for Access to and/or Treatment of the Spine.
U.S. Appl. No. 11/760,558 U.S. Pat. No. 8,123,751, filed Jun. 8, 2007, Methods and Apparatus for Access to and/or Treatment of the Spine.
U.S. Appl. No. 11/760,569 U.S. Pat. No. 7,892,238, filed Jun. 8, 2007, Methods and Apparatuses for Percutaneous Access to the Spine.
U.S. Appl. No. 16/122,668, filed Sep. 5, 2018, Methods and Apparatus for Access to and/or Treatment of the Spine.

\* cited by examiner

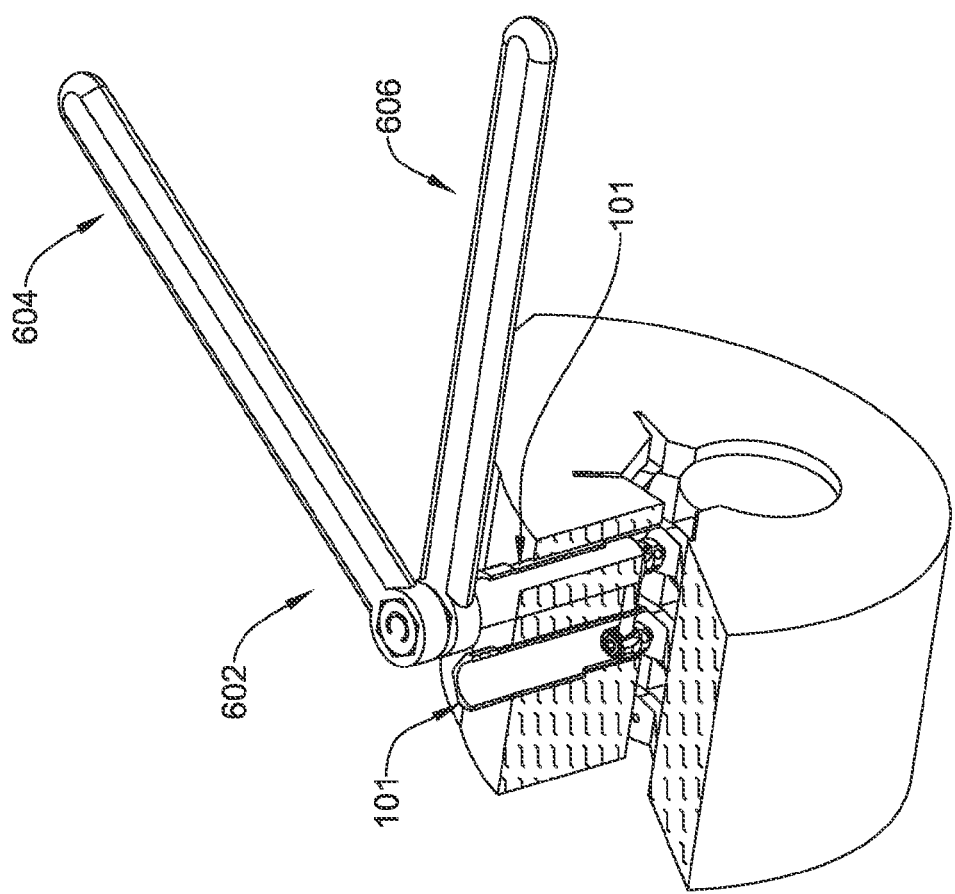

METHODS AND APPARATUS FOR ACCESS TO AND/OR TREATMENT OF THE SPINE

CROSS-REFERENCE TO RELATED APPLICATIONS

This application is a continuation of U.S. patent application Ser. No. 16/122,668, filed on Sep. 5, 2018, now U.S. Pat. No. 10,905,407, issued Feb. 2, 2021, which is a continuation of U.S. patent application Ser. No. 14/727,142, filed Jun. 1, 2015, now U.S. Pat. No. 10,085,732, issued on Oct. 2, 2018, which is a continuation of U.S. patent application Ser. No. 11/760,551, filed Jun. 8, 2007, now U.S. Pat. No. 9,055,934, issued Jun. 16, 2015, which claims the benefit of U.S. Provisional Patent Application No. 60/812,703, filed Jun. 9, 2006. The present application is related to U.S. Provisional Patent Applications No. 60/514,559, filed Oct. 24, 2003, 60/545,587, filed Feb. 18, 2004, and 60/579,643, filed Jun. 15, 2004. This application also is related to U.S. patent application Ser. No. 10/927,633, filed Aug. 26, 2004, now U.S. Pat. No. 7,179,225, issued on Feb. 20, 2007, and is related to U.S. patent application Ser. No. 10/926,579, filed Aug. 26, 2004, now U.S. Pat. No. 7,976,464, issued on Jul. 12, 2011. The entire contents of each of the foregoing applications is hereby expressly incorporated by reference herein.

BACKGROUND

This application relates to surgical systems, assemblies, devices, and methods that may be used for less invasive and/or minimally invasive surgery, and in particular relates to surgical systems, assemblies, devices, and methods that may relate to gaining access to and/or treatment of the spine.

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Systems, assemblies, devices, and methods for performing less invasive and/or minimally invasive techniques have been proposed to reduce the trauma of posterior spinal surgery by reducing the size of the incision and the degree of muscle stripping in order to access the vertebrae. A number of different such systems, assemblies, devices, and methods are known, each having certain advantages and disadvantages. However, there is an ongoing need to provide alternative systems, assemblies, devices, and methods for gaining access to and/or treating the spine of a patient.

SUMMARY OF SOME EXAMPLE EMBODIMENTS

The invention provides several alternative systems, assemblies, devices, and/or methods for gaining access to and/or treating the spine of a patient.

Some example embodiments relate to an access device for providing access to a spinal location within a patient. The access device may include an elongate body having a proximal portion and a distal portion and a length therebetween such that when the distal portion is positioned inside the patient adjacent the spinal location, the proximal portion extends outside the patient. The device may also includes a passage extending through the elongate body between the proximal and distal portions, and one or more channels and/or laterally facing openings and/or cutouts in the distal portion that may be sized and/or configured to permit a fixation element to pass through. In some example embodiments, the distal portion may be expandable from a first non-expanded configuration to a second, expanded configuration.

Some example embodiment relates to a spinal access assembly including two or more spinal access devices, each access device having an elongate body with a proximal portion and a distal portion and a length therebetween such that when the distal portion is positioned inside a patient adjacent a spinal location, the proximal portion extends outside the patient. The spinal access devices may also have a passage extending through the elongate body between the proximal and distal portions, and one or both of the access devices may include one or more channels and/or laterally lacing openings and/or cutouts in the distal portion that may be sized and/or configured to permit a spinal fixation element to pass through. In some example embodiments, the distal portion of one or both of the access devices may be expandable from a first non-expanded configuration to a second, expanded configuration.

Some example embodiments also relate to a spinal access and treatment assembly that may include two or more spinal access devices, such as any of those discussed above, or hereinafter, and a spinal fixation element, and two or more spinal fasteners configured to affix the spinal fixation element to vertebrae of a patient.

Additional embodiments relate to methods for treating the spine of a patient. Some such embodiments may involve the use of two or more access devices, for example, any of those discussed herein. One example method may include inserting a first access device through a first incision in the skin of the patient, the first access device having a first proximal end and a first distal end and a first passage therebetween, wherein a portion of the first distal end has a first opening, and advancing the first access device until the first distal end is adjacent a first spinal location. The method may also include inserting a second access device through a second incision in the skin of the patient, the second access device having a second proximal end and a second distal end and a second passage therebetween, wherein a portion of the second distal end has a second opening, and advancing the second access device until the second distal end is adjacent a second spinal location. A spinal fixation element having a proximal end and a distal end may be inserted through the first passage until the distal end of the fixation element is adjacent the first spinal location. The distal end of the fixation element may be advances through the first opening and through the second opening to the second spinal location, until the proximal end of the fixation element is adjacent the first spinal location and the distal end of the fixation element is adjacent the second spinal location.

Another example method for treating the spine of a patient may include advancing a first access device into the patient such that a distal end of the first access device is adjacent a first spinal location, wherein a portion of the distal end of the first access device may include a channel and/or cutout and/or laterally facing opening. The method may also include advancing a second access device into the patient such that a distal end of the second access device is adjacent a second spinal location, wherein a portion of the distal end of the second access device may include a channel and/or cutout and/or laterally facing opening. A fixation element having a proximal end and a distal end may be inserted through the first access device until the distal end of the fixation element is adjacent the first spinal location, and the fixation element may be advanced through the a channel and/or cutout and/or laterally facing opening of the first access device and through the channel and/or cutout and/or laterally facing opening in the second access device, until the proximal end of the fixation element is adjacent the first spinal location and the distal end of the fixation element is adjacent the second spinal location.

A further method for treating the spine of a patient may include inserting a first retractor through a first incision in the skin of the patient, the first retractor having a first proximal end and a first distal end and a first passage therebetween, wherein a portion of the first distal end may have a first channel and/or cutout and/or laterally facing opening. The method may also includes advancing the first retractor until the first distal end is adjacent a first spinal location, and inserting a second retractor through a second incision in the skin of the patient, the second retractor having a second proximal end and a second distal end and a second passage therebetween, wherein a portion of the second distal end may have a second channel and/or cutout and/or laterally facing opening. The method may also include advancing the second retractor until the second distal end is adjacent a second spinal location, and inserting a fixation rod having a proximal end and a distal end through the first passage and channel and/or cutout and/or laterally facing opening of the first retractor and into the channel and/or cutout and/or laterally facing opening of the second retractor until the distal end of the fixation rod is adjacent the second spinal location and the proximal end of the fixation rod is adjacent the first spinal location.

Some example embodiments relate to a pedicle screw assembly. The screw assembly may include a threaded shaft, and a head including a housing and an elongated body. The housing may be attached to the elongated body at a frangible neck, and the elongated body may be adapted to be removed from the housing at the frangible neck. The housing may also be configured to receive a spinal fixation element. In some embodiments, the elongated body may have a length sufficient such that the elongated body extends above a patient's skin when the screw is secured to the patient's vertebra.

In some embodiments, a breakoff pedicle screw assembly is disclosed, and may include a threaded shaft, and a breakoff head that has a distal portion attached to the shaft and configured to receive a fixation rod, a neck region, and an elongated proximal portion. The neck region may be configured such that application of a sufficient amount of torque to the proximal portion causes the proximal portion to be separated from the distal portion at the neck region. In some embodiments, the elongated proximal portion may have a length sufficient such that the elongated proximal portion extends above a patient's skin when the screw is secured to the patient's vertebra.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

Further objects, features and advantages of the invention will become apparent from the following detailed description taken in conjunction with the accompanying figures showing illustrative embodiments of the invention, in which:

FIGS. 43-46 schematically illustrate example methods for inserting embodiments of screws with breakoff heads and for removing the breakoff heads from the screws, including a perspective view in FIG. 44A and a top view in FIG. 44B of a countertorque handle with retractors, breakoff heads, and a fixation element.

Figure 1:
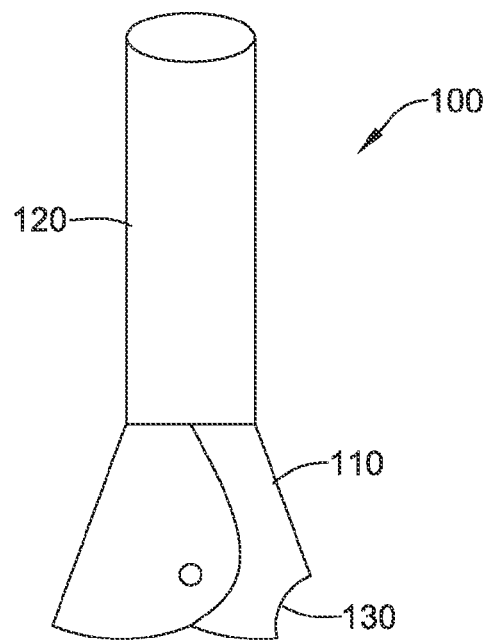
FIG. 1 schematically illustrates an embodiment of an access device.

Throughout the figures, the same reference numerals and characters, unless otherwise stated, are used to denote like features, elements, components or portions of the illustrated embodiments. Moreover, while the subject matter of this application will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION

Various embodiments of apparatuses and procedures described herein will be discussed in terms of minimally invasive procedures and apparatuses, e.g., of endoscopic apparatuses and procedures. However, many aspects of the present invention may find use in conventional, open, and mini-open procedures. As used herein, the term "proximal," as is traditional, refers to the end portion of the apparatus that is closest to the operator, while the term "distal" refers to the end portion that is farthest from the operator.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra(e) within the cervical, thoracic, and lumbar regions of the spine. The procedures may be directed toward surgery involving one or more vertebral levels. Some embodiments are useful for anterior and/or lateral procedures. Moreover, it is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly useful for minimally invasive procedures, e.g., arthroscopic procedures. As discussed more fully below, one embodiment of an apparatus described herein provides an access device that provides retraction, allows visualization of a spinal location, and provides a passage for surgical instruments. In some embodiments, the access device acts as a retractor. In one embodiment the access device has an expandable distal portion. In other embodiments, the access device is not expandable. In addition to providing greater access to a surgical site than would be provided with device having a constant cross-section, the expandable distal portion prevents or substantially prevents the access device, or instruments extended therethrough to the surgical site, from dislodging or popping out of the operative site.

Some of the systems and methods disclosed herein can be used to access a surgical location at or near the spine of a patient to enable procedures on the spine. These procedures can be applied to one or more vertebral levels, as discussed herein. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described herein. These procedures may be performed primarily through retractors or other similar access devices, such as those discussed herein. In some techniques, the procedures may be at least partially performed percutaneously, e.g., over a guidewire or other structure that has a smaller profile than the access devices describe herein. By performing at least a portion of the procedures percutaneously, the amount of time that a retractor or similar access device is deployed or expanded may be reduced. Also, percutaneous techniques described herein increase the ability of the surgeon to quickly and easily deliver place markers, fasteners, and other implants to target sites, to prepare target sites, and to complete procedures. Percutaneous techniques enable the performance of a substantial portion of a spinal procedure with little or no visualization of the location where the procedure is performed.

Accordingly, it is desirable to provide systems, methods, and devices for percutaneous and partially percutaneous access that reduce tissue trauma, require less surgical time, and reduce the need for fluoroscopy and image-guided assistance. In some embodiments, the systems, methods, and devices permit posterolateral fixation and/or fusion procedures to be performed at least partially percutaneously.

In one embodiment, the system includes an access device that provides an internal passage for surgical instruments to be inserted through the skin and muscle tissue of the patient to the surgical site. The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The access device may provide distraction with or without having an expandable component. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures.

One embodiment of the access device includes a wall portion defining a reduced profile configuration for initial percutaneous insertion into the patient. This wall portion may have any suitable arrangement. In one embodiment the wall portion has a generally tubular configuration that may be passed over a dilator that has been inserted into the patient to atraumatically enlarge an opening sufficiently large to receive the access device therein.

The wall portion of the access device can be subsequently expanded to an enlarged configuration, by moving against the surrounding muscle tissue to at least partially define an enlarged surgical space in which the surgical procedures will be performed. Accordingly, the expanded wall portion may act similarly to a dilator. Both the distal and proximal portion may be expanded. However, the distal portion may expand to a greater extent than the proximal portion, because the surgical procedures are to be performed at the surgical site, which is adjacent the distal portion when the access device is inserted into the patient.

While in the reduced profile configuration, the access device defines a first unexpanded configuration. Thereafter, the access device can enlarge the surgical space defined thereby by engaging the tissue surrounding the access device and displacing the tissue outwardly as the access device expands. In some embodiments, the access device is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein. The surgical site is at least partially defined by the expanded access device itself. During use, the access device can move from a first unexpanded configuration to a second expanded configuration.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician may remain substantially stable during such distal movement. In one embodiment, the distal portion is a separate component that is pivotally or movably coupled with the proximal portion. In another embodiment, the distal portion is flexible or resilient in order to permit such relative movement. The access device is configured such that the proximal portion can pivot in at least one direction with respect to the distal portion.

A. Methods and Devices for Spinal Access

As discussed above, the systems disclosed herein can be used to access a surgical location at or near the spine of a patient to enable procedures on the spine. These procedures can be applied to one or more vertebral levels, as discussed herein. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described herein. The procedures may be partially or completely performed percutaneously, e.g., over a guidewire or other structure that has a smaller profile than the access devices describe herein.

Certain of the procedures described herein can be performed in part percutaneously and in part minimally invasively, e.g., through an access device. In some methods, a device that includes a hollow structure is used to form a percutaneous entry or path between the skin and a vertebral surface or a vertebral target site. In other procedures, the percutaneous entry or path may be formed between the skin of the patient and a suitable target site on or near the spine of the patient. A vertebral target site is any site on a vertebra at which a procedure or a portion of a procedure is to be performed. For example, as discussed below, some procedures may advantageously be performed at a pedicle of a vertebra or at a region between a facet joint and a transverse process of a vertebra. In one technique the hollow structure of the percutaneous entry forming device is configured to receive a sharp implement, which is configured to cut and separate tissue. As tissue is cut and separated, the percutaneous access path can be formed between the skin and the vertebral surface.

In some percutaneous methods, cannulated fasteners (e.g., pedicle screws) are implanted through tissue over a guidewire to a vertebral target site, for example, the lumbar region of the spine. In some embodiments, after the fasteners are attached to the target site, a fixation member (e.g., a rod or a plate) is implanted as part of a fusion or fixation procedure. However, certain fixation member implantation methods require an additional incision and muscle dissection for placement of the fixation member and/or require cutting or splitting the tissue between the fasteners from the skin distally to place and secure the fixation member. Also, some methods employ but may not require fluoroscopic or image-guided assistance to place the fasteners at the target site.

Accordingly, it is desirable to provide systems, methods, and devices for percutaneous access that reduce tissue trauma, require less surgical time, reduce the need for fluoroscopy and image-guided assistance. In some embodiments, the systems, methods, and devices permit posterolateral fixation and/or fusion procedures to be performed at least partially percutaneously.

In certain embodiments, the methods involve creating a pedicle tunnel "percutaneously" using, for example, guidewires and implants and instruments that can be delivered thereover. Additionally, one or more such methods can be at least partially performed through one or more small tubular retractors. In certain embodiments, the retractors comprise an expandable portion as described herein. After the implants are in place in each retractor, the distal portions of the retractors can be adjusted to form a tunnel to permit a fixation member to be inserted proximally through one of the retractors and then positioned onto a fastener distally. In some embodiments, the tunnel is formed by expanding the distal portions of one or more retractors. The fixation member (e.g., a rod or a plate) can be positioned onto the fastener without the need for an additional incision or muscle splitting. A benefit of some embodiments of this method is that, where fixation assemblies are to be deployed on both sides of the spinous process, only two small incisions per side of the spinous process are made for a single-level procedure.

Some embodiments of the procedures disclosed herein reduce tissue trauma, because less cutting and splitting of the muscles, fat, and fascia is required. In some procedures, an endoscope and/or lighting devices for visualizing the anatomy can be positioned within one or more of the tubular retractors. Additionally, manipulation of the fasteners (e.g., screw heads) for compression or distraction of the joint space between the fasteners can also be performed with these methods. Embodiments of the methods disclosed herein are suitable for fixation or fusion procedures and may be used with any suitable spinal approach such as, for example, a posterolateral approach.

The following is a non-limiting and nonexclusive list that comprises actions that may be performed in one embodiment of a spinal surgical technique (e.g., a one-level spinal fixation procedure). Additional and/or different actions can be performed in other spinal procedures according to other techniques. Further, the actions may be performed in a different order than shown, and some of the enumerated actions may be eliminated in other techniques.

One embodiment involves a method for an at least partially percutaneous spinal procedure. The procedure may include, for example, a fixation, a fusion, and/or other suitable stabilization procedure. In this example procedure, a trocar and needle (such as a Jamshidi needle or bone biopsy needle) are percutaneously passed through the skin and into the targeted pedicle and into the vertebral body. The trocar and needle form a percutaneous access path that is sometimes referred to herein as a tissue tunnel. In one technique, the trocar is inserted into the needle and the trocar and needle are advanced together through the skin at a skin puncture location and through subcutaneous tissue (e.g., through fat, muscle, and fascia) until a distal end of the trocar and needle are at the vertebral target site. The needle and trocar thus create a tissue tunnel through subcutaneous tissue. In one method, a generally posterolateral approach is employed and the initial advancement of the needle and trocar positions the needle and trocar at the pedicle of the target vertebra. Advancement of the needle and trocar may be aided by fluoroscopy, e.g., using a C-arm or other similar technique.

After a percutaneous entry, or percutaneous entry path, has been created through the skin and subcutaneous tissue, the vertebral target site may be prepared, if desired. In one method, the needle and trocar are advanced further into the target vertebra at the vertebral target site to form a tunnel in the target vertebra. The tunnel may be formed in the pedicle and is sometimes referred to as a pedicle tunnel. A proximal end of the trocar remains outside the patient, above the skin puncture location throughout the target site preparation. Preparation of the vertebral target site may include further procedures, such as tapping of the pedicle tunnel.

In one embodiment, the trocar is removed, leaving the needle in the pedicle. A guidewire, or other elongate body, is inserted into the proximal end of the needle. The guidewire may be advanced through the tissue tunnel and through the pedicle tunnel within the needle. In one application, the guidewire is advanced until a distal end of the guidewire is located in the vertebral body of the target vertebra. The guidewire extends proximally from of the skin and of the proximal end of the needle. The needle is removed leaving the guidewire in place, extending distally into the pedicle tunnel and proximally out of the skin.

Optionally, it may be advantageous to prepare the pedicle tunnel by forming threads within the tunnel. One method of forming threads in the pedicle tunnel involves tapping the pedicle tunnel with a cannulated tap. A cannulated tap is a low profile instrument that has an elongate body and an outside surface. The elongate body extends between a proximal end and a distal end. A bore, or cannulation, is formed through the elongate body between the proximal and distal ends. The elongate body has formed thereon a structure configured to form internal threads within the pedicle tunnel, e.g., on the outer surface. The cannulated tap may be advanced over, e.g., slid over, the guidewire until the distal end is at the vertebral target site. Thereafter the cannulated tap may be rotated about the guidewire and advanced, turning the cannulated tap into the pedicle tunnel. As the cannulated tap advances the threads are formed in the pedicle tunnel. Tapping creates threads in the pedicle tunnel that will mate with corresponding threads on an implant to be inserted later.

In some applications, further dilation of the percutaneous access path or entry facilitates insertion of an implant. In one technique, a small incision is created at the skin puncture location. In one technique, an incision is created that is about 5-15 mm long. In some variations, an incision that is less than 5 mm can be created. The incision also can extend a distance into the tissue beneath the skin. The incision facilitates the insertion of one or more dilators (or obturators) over the wire to increase the size of the percutaneous access path or entry. The dilator may be advanced at least a substantial portion of the distance from the skin puncture location to the surface of the vertebra to reduce the resistance of the tissue beneath the skin to the insertion of an implant. The dilators are removed prior to insertion of an implant in one technique. The dilators/obturators may be inserted at the access site to create a tunnel through the tissue to the pedicle.

Although significant advantages are realized by preparing the vertebral target site prior to insertion of an access device, blood and other body fluids and tissues can hide or obscure the location of the prepared site. After the percutaneous access path or entry has been created, a marker may be delivered over the guidewire to the vertebral target site. Placing a marker within the pedicle tunnel aids the surgeon in finding the pedicle tunnel later in the procedure. Further details of a marker suitable for use with methods discussed herein is disclosed in U.S. patent application Ser. No. 11/184,568, filed Jul. 19, 2005, titled METHODS AND APPARATUSES FOR PERCUTANEOUS IMPLANT DELIVERY, which is hereby incorporated by reference herein in its entirety.

In one method, an access device is inserted into the patient to enclose one or more of the adjacent pedicles in a working space so that a minimally invasive portion of a procedure may be performed. In particular, an incision may be created by connecting, by extending, or by connecting and extending the incisions made for the guidewires. After the incision is made, the tissue may be dilated, and an access device or a retractor may be inserted over the dilator (or obturator). In some embodiments, the access device comprises an expandable distal portion that may be expanded so that the distal portion extends over one or more of adjacent pedicles (and any previously inserted markers). Two tubular retractors may be inserted at two adjacent vertebral sites. In some techniques, after the access device is inserted over the dilator or obturator (or a series of these), the dilator(s) or obturator(s) are removed, leaving the guidewire in place within the access device.

In one technique, a fastener such as, for example, a cannulated pedicle, screw, is inserted over a proximal end of the guidewire. A cannulated screwdriver device can be used to move the fastener through the access device to the vertebral site, where it can be attached to the pedicle and vertebral body (e.g., by screwing with the cannulated screwdriver). In one method, after insertion and attachment of the fastener, the screwdriver and the guidewire can be removed, leaving the fastener and access device in place.

In some methods, after a first fastener is attached to a first vertebral site (and the guidewire removed), the above techniques are repeated so that a second fastener is attached to a second vertebral site and so on. However, in other methods, a trocar, needle, and guidewire are installed at each of the vertebral sites (e.g., at each pedicle), and then the subsequent acts of expanding the surgical site with a dilator/obturator, inserting the access device, and securing a fastener to the vertebral body (e.g., at a pedicle) are performed.

Each access device is oriented properly and expanded distally to allow mating openings of the distal portion to align and create a short tunnel for passing a rod or other fixation element between access devices. The screw heads are oriented and aligned with the tunnel to receive the rod. The rod is then placed proximally though one of the access devices and is targeted and positioned to the tunnel opening by a variety of means (e.g., rod holder, slide-like guide, suture thread, wire or cable, etc.). The rod is manipulated (by pushing or pulling or a combination of these) through the tunnel from one access device to the next (and successive retractors if more than 1-level) until the rod is positioned and seated in all screw heads in preparation for placement of a securing means (e.g., cap screw). The rod is secured to each screw head using fixating and delivery instrument means through each access device. Instruments such as countertorque drivers, torque limiting instruments and compressor/distractor instruments may be utilized as desired by the surgeon. Bone graft may be placed through the tubes and around the screws and connecting member as desired.

It is appreciated that many variations of this method are possible and that the actions described herein can be performed in many ways and in many orders so as to enable access to the vertebral sites. For example, a one-level procedure may involve delivering two fasteners (e.g., pedicle screws) to two adjacent vertebral sites (e.g., L4 and L5) using two access devices.

In certain embodiments, the access device provides an internal passage for surgical instruments to be inserted through the skin and muscle tissue of the patient to the surgical site. The access device has a wall portion defining a reduced profile, or low-profile, configuration for initial percutaneous insertion into the patient. This wall portion may have an suitable arrangement. In one embodiment, the wall portion has a generally tubular configuration that may be passed over a dilator that has been inserted into the patient to atraumatically enlarge an opening sufficiently large to receive the access device therein. In some methods, the distal portion of the access device is expanded prior to insertion of a fastener into the access device, while in other methods the distal portion is expanded at a later stage of the procedure.

In some embodiments, the proximal and distal portions of the access device are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician may remain substantially stable during such distal movement. In one embodiment, the distal portion is a separate component that is pivotally or movably coupled to the proximal portion. In another embodiment, the distal portion is flexible or resilient in order to permit such relative movement.

Figure 2:
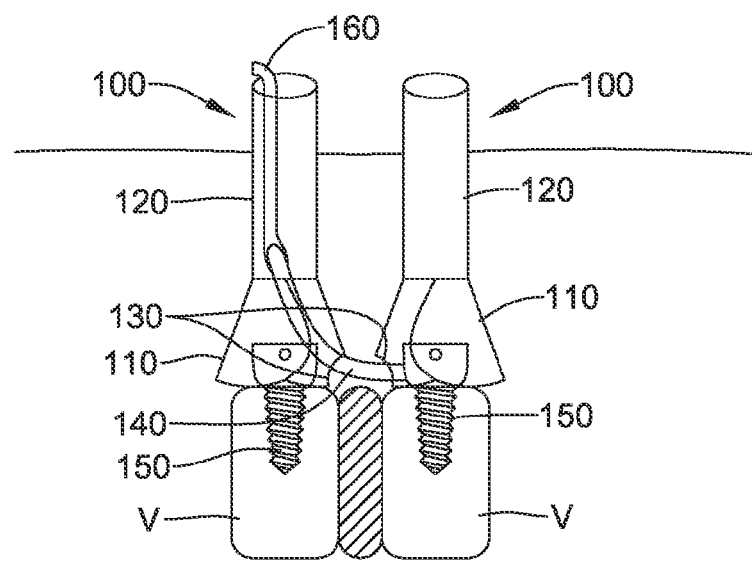
FIGS. 2-3 schematically illustrate an embodiment of a method and assembly for percutaneously performing a one-level spinal procedure.

FIG. 1 schematically illustrates an embodiment of an access device 100 that can be used with the methods disclosed herein. In this embodiment, access device 100 has a tubular configuration with an expandable distal portion 110 configured to have one or more rod delivery channels 130 "cut outs" or "mating openings" and/or "laterally facing openings") that are sized and shaped to permit a fixation element (e.g., a rod or a plate) to pass therebetween. In some embodiments, the channels or cut-outs 130 are in a side wall of the expandable distal portion 110. In other embodiments, laterally facing openings 130 permit a fixation element to pass through. In further embodiments, the access device 100 has two or more cut-outs 130 in opposing sides of the distal portion 110. FIG. 2 schematically illustrates the placement of fixation element 140 (shown as a rod) through channels 130 in an example of a one-level procedure involving two access devices 100 positioned over vertebrae V. Similar methods may involve the placement of three, four, or more access devices to provide access to multiple spinal locations, and may involve multi-level procedures.

Some example structures and/or configurations of access devices that can be used with the methods disclosed herein are disclosed in U.S. patent application Ser. No. 10/926,579, filed Aug. 26, 2004, published as Publication No. U.S. 2005/0273131 A1, U.S. patent application Ser. No. 10/927,633, filed Aug. 26, 2004, now U.S. Pat. No. 7,179,225, U.S. patent application Ser. No. 10/845,389, filed May 13, 2004, entitled "Access Device For Minimally Invasive Surgery," U.S. patent application Ser. No. 10/658,736, filed Sep. 9, 2003, U.S. patent application Ser. No. 10/117,440 (filed Apr. 5, 2002, published Oct. 9, 2003 as Publication No. U.S. 2003/0191371A1), Ser. No. 10/180,658 (filed Jun. 26, 2002, published Jan. 1, 2004 as Publication No. U.S. 2004/0002629A1), Ser. No. 10/792,358 (filed Mar. 3, 2004, published Sep. 9, 2004 as Publication No. U.S. 2004/0176665A1), which are hereby expressly incorporated by reference herein in their entireties. In addition, such assess devices as disclosed therein may be modified and/or may include one or more channels 130 (e.g., "cut outs" or "mating openings" and/or "laterally facing openings") as discussed above.

In one method, first and second access devices are oriented so that the channels 130 are generally facing or aligned with each other as shown in FIG. 2. In techniques using one or more expandable access devices 100, an expandable distal portion 110 of the access device may be expanded to create a short tunnel that permits passage of a fixation element 140. Portions of the fasteners 150 (e.g., the pedicle screw heads) may be oriented and aligned with the tunnel so as to receive the fixation element 140.

The fixation element 140 (e.g., the rod shown in FIG. 2) is then placed proximally through one of the access devices 100 and can be moved to the tunnel opening using a variety of devices and/or techniques. The fixation element 140 may be a rigid element, such as a rigid rod or plate. In another embodiment, the fixation element 140 may be a flexible element that enables the adjacent vertebrae to maintain a degree of their natural range of motion. Additional structure related to flexible fixation elements and technique for application of such elements are set forth in U.S. patent application Ser. No. 10/693,815, filed Oct. 24, 2003, which is hereby incorporated by reference herein in its entirety.

For example, FIG. 2 schematically shows the fixation element 140 being pushed into and through the tunnel with a rod inserter 160. Alternatively, a rod holder, a slide-like guide, a suture thread, wire, or cable can be used to push (and/or pull) the fixation element from one access device, through the tunnel, to the next access device.

Figure 3:
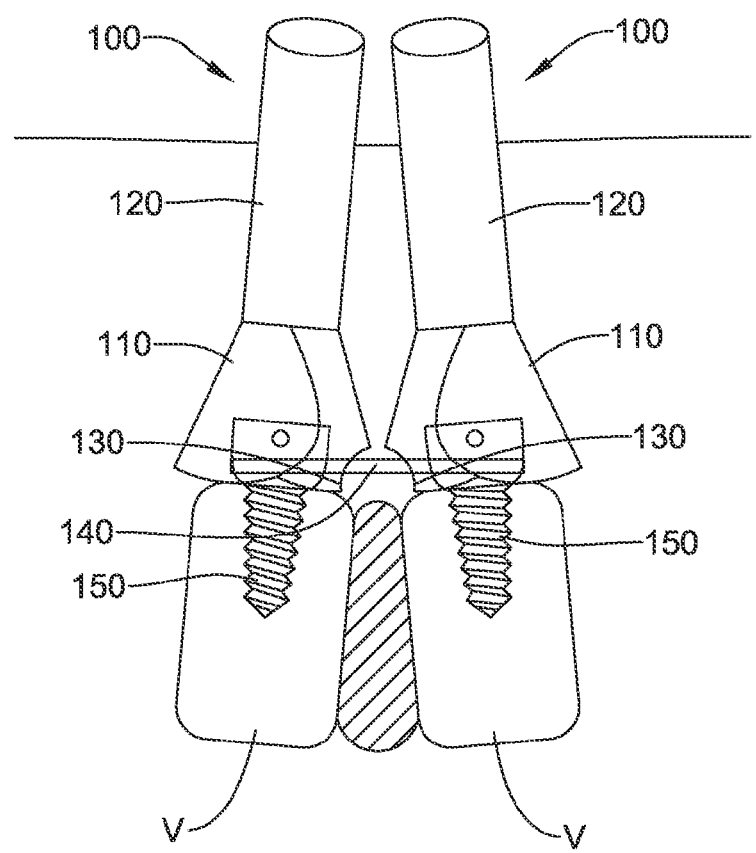

The fixation element 140 can be manipulated by pushing or pulling (or a combination of pushing and pulling) from one access device 100 to the next, through the tunnel. If a multilevel procedure is performed, the fixation element 140 can be manipulated through successive access devices 100. In certain methods, the fixation element 140 is positioned and seated in the fasteners 150 (e.g., within the screw heads) in preparation for placement of a securing means (e.g., a cap screw). The fixation element 140 is secured to each of the fasteners 160 using fixating and delivery instruments and device inserted through the access devices 100. For example, devices such as countertorque drivers, torque limiting instruments, and compressor-distractor instruments may be utilized by the physician. In some methods, bone graft may be placed through the access devices 100 and disposed around the fasteners 150 and fixation elements 140 as needed to enhance the growth of bone between the fasteners 150 and the fixation elements 140 and between these elements and adjacent vertebrae V. FIG. 3 schematically illustrates the completed one-level construct prior to the removal of the access devices 100. A second one-level construct can be applied to the spine on the other side of the spinous process.

Figure 4:
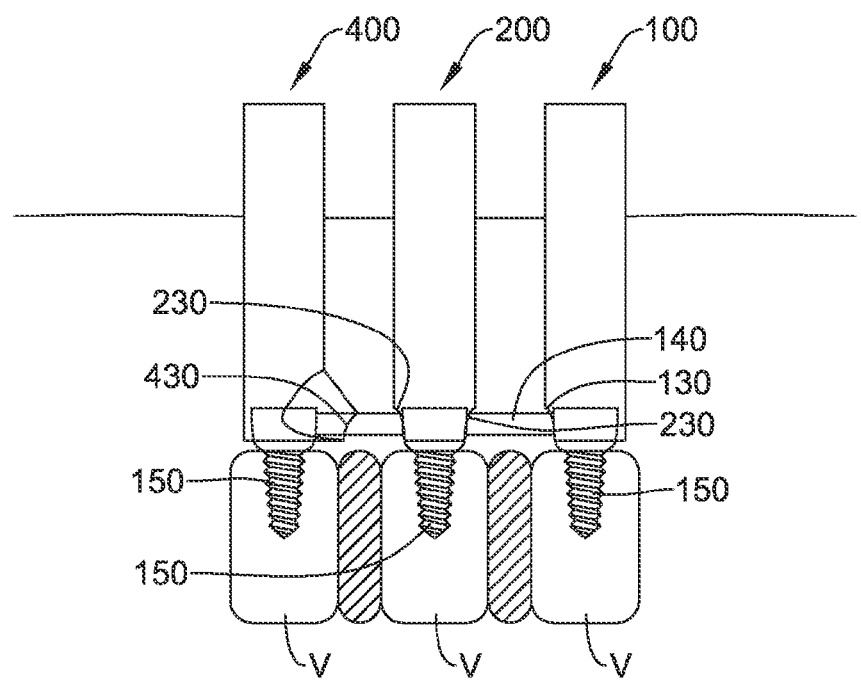
FIG. 4 schematically illustrates an embodiment of a method and assembly for percutaneously performing a multi-level spinal procedure.

One-level, two-level, and more than two-level three-level and other multi-level) procedures are contemplated. FIG. 4 schematically illustrates multilevel constructs utilizing three access devices 100, 200, 400. As shown in FIG. 4, in certain methods the center access device 200 may have channels 230 (e.g., "cut outs" or "mating openings" and/or "laterally facing openings") on opposite sides of the distal wall portion. In some embodiments, the channels 230 are arranged to be about 180 degrees apart. The use of such a "double slotted" access device 200 advantageously permits a fixation element 140 (e.g., a rod) to pass entirely through the center access device 200 so as to engage fasteners 150 disposed on adjacent vertebrae V. In some of these methods, each of the access devices 100, 200, 400 is oriented so that its channels 130, 230, 430 are generally aligned with the channels on the other access devices. This orientation provides a tunnel that is suitable for passage of the fixation element 140 through all of the access devices 100, 200, 400 in a multilevel procedure.

FIG. 4 schematically illustrates various access devices suitable for use in single- or multi-level procedures. A distal portion of the access device 100, 200, 400 is configured with one or more slots, holes, cut outs, openings, channels, or tunnels 130, 230, 430. In some embodiments, the slots are disposed on one side of the distal portion of the access device, while in other embodiments the slots are disposed on both sides (e.g., about 180 degrees apart). In yet other embodiments, slots may be arranged at other positions around the access device in either a uniform or non-uniform distribution of positions. As described with reference to FIG. 4, a two-sided slotted access device is particularly advantageous in multilevel procedures because the mutually opposed slots permit passage of the fixation device 140 entirely through the access device 200 (see FIG. 4). The distal portion of the access device may be expandable, as shown in access device 400, or not expandable, as shown in access devices 200, 100. Many variations are possible. For example, FIG. 4 schematically illustrates one multilevel method that utilizes three access device variations: a one-sided slotted expanding retractor 400, a two-sided slotted non-expanding retractor 200, and a one-sided slotted non-expanding retractor 100. In other embodiments, the distal portion of the access device does not expand, but is configured to pivot or rotate about a pivot point.

Although the methods discussed with reference to FIGS. 1-4 illustrate a posterolateral lumbar spinal surgery procedure through an access device, in other embodiments, similar methods can be used for other regions of the spine (e.g., cervical and thoracic regions), and other approaches may be used (e.g., anterior, lateral, and retroperitoneal). Many variations are possible without departing from the scope of the methods disclosed.

Figure 5:
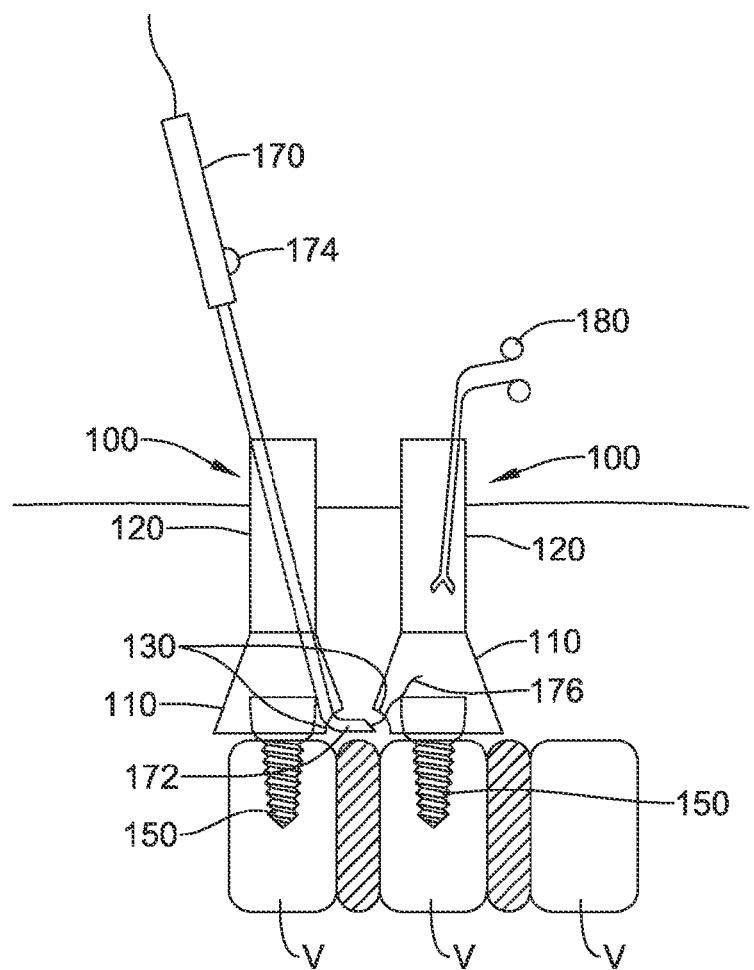
FIGS. 5-7 schematically illustrate embodiments of methods and devices used to insert a fixation element.
Figure 6:
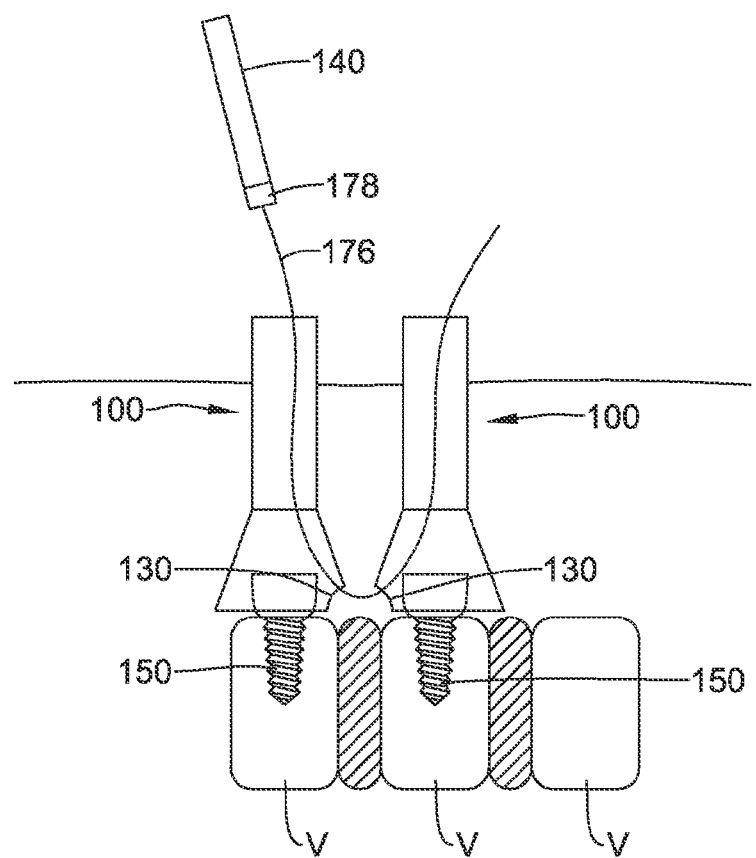
Figure 7:
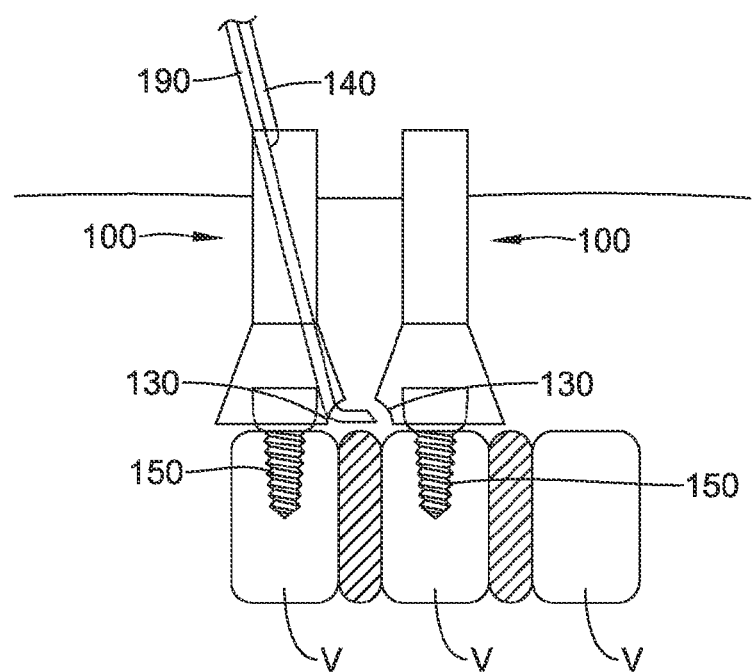

FIGS. 5-7 schematically illustrate embodiments of methods and devices that can be used to insert and position a fixation element 140 during a spinal procedure. In FIG. 5, a suture passer instrument 170 or a needle is used to pass a flexible pulling member such as a suture, wire, cable 176, or other suitable connecting element, through a tunnel formed between two slotted access devices 100. The suture passer 170 is inserted into a first access device 100 and used to position the suture 176 at a slot or cut out 130 at a distal end 110 of the first access device 100. The suture passer 170 can be configured with a rounded or hooked end portion 172 that can be pushed partially or totally through the tunnel so as to provide access to an end of the suture 176 in a second access device 100. A grasping instrument 180 can be used to grab or hold the end of the suture 176 and pull it through the second access device 100. In some embodiments, the suture passer instrument 170 has a thumbwheel 174 configured so that rotation of the thumbwheel 174 causes the suture 176 to be advanced through the suture passer 170.

After a portion of the suture 176 is inserted through the access devices 100 and the tunnel formed therebetween, an end of the suture 176 may be attached to a fixation element or rod 140. See FIG. 6. The attachment may be via an attachment element 178 such as an eyelet, finger trap suture, a flexible cap, clamp or other attachment means, or the like. After attachment, the fixation element 140 may be positioned in the tunnel between the access devices 100 by pulling on the suture 176. In some embodiments, the fixation element 140 is cannulated and passes over the suture 176. After attachment of the suture, the fixation element 140 is positioned in the tunnel between the access devices 100 by pulling on an opposite end of the suture 176. In some methods, additional instruments, such as grasper apparatus 180, may be used to assist in positioning the fixation element 140.

FIG. 7 illustrates an alternative method to insert a fixation element 140. In this method, a guide 190 is used to position the fixation element 140 within the tunnel between the access devices 100. In certain embodiments, the guide 190 is a slotted "slide" to permit the physician to slide the fixation element 140 toward the distal end of the guide 190. In some embodiments, the guide 190 has a concave configuration for receiving and guiding the fixation element 140 through the passage in the access device 100. The guide 190 may have a curved distal end to facilitate guiding the fixation element through a cut-out 130 or opening in the access device. In one technique, the one or more access devices 100 can be pivoted so as to help position the guide 190.

Figure 8:
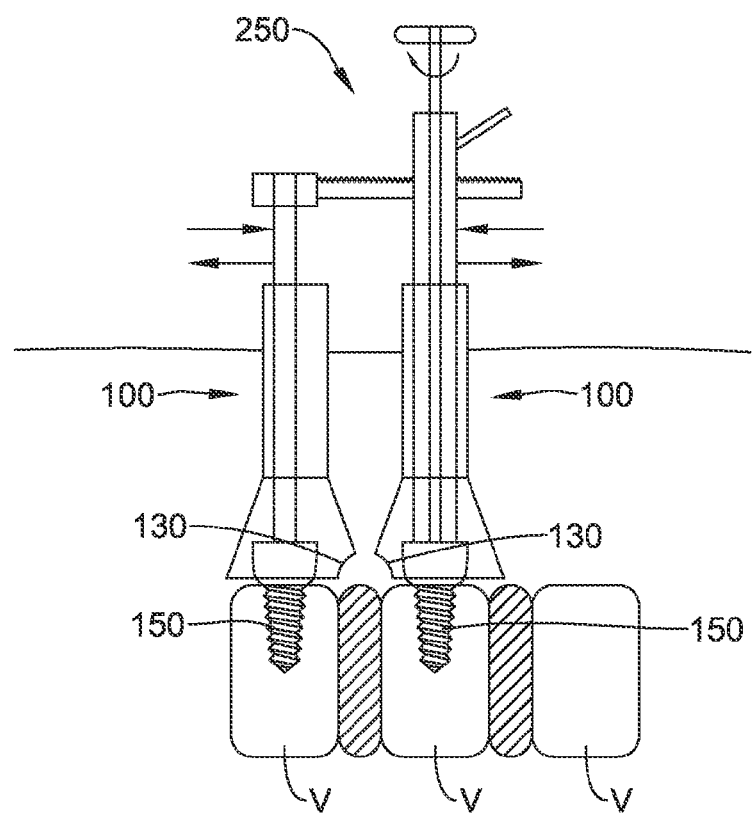
FIG. 8 schematically illustrates an embodiment of a compressor-distractor instrument used with access devices.

Additional instruments, devices, and apparatuses can be used in the fixation or fusion procedures. For example, FIG. 8 schematically illustrates a compressor-distractor device 250 that can be used to shift the vertebrae prior to final securing of the fixation element 140 to the fasteners 150 attached to the vertebrae.

Figure 9:
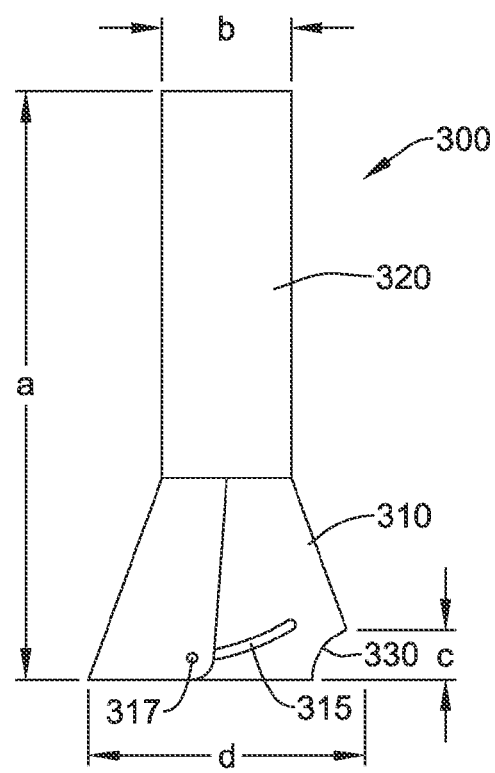
FIGS. 9-12C schematically illustrate various embodiments of access devices with channels and/or cutouts and/or laterally facing openings.
Figure 10:
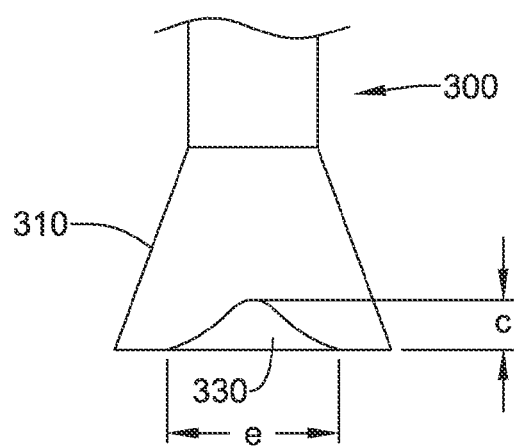

FIGS. 9-12C illustrate several embodiments of access devices that can be used with the percutaneous methods discussed herein. FIGS. 9-10 schematically illustrate side views (FIG. 9) and end views (FIG. 10) of an expanding access device 300 comprising a distal end 310 that is pivotally attached to a tube portion 320, e.g., via one or more rivets or pins or protrusion. The distal end 310 comprises at least one slot 315 that can slide around a pin or rivet 317 attached to the tube portion. In a contracted configuration, the distal end 310 is pivoted inwards so that the pin or rivet 317 engages one end of the slot 315. In an expanded configuration, the distal end 310 is moved away from the tube portion 320 so that the pin or rivet 317 engages the other end of the slot 315. The length of the slot 315 and the position of the pin or rivet 317 can be adjusted to provide for differing amounts of expansion. FIGS. 9-10 also show example dimensions and sizes of certain embodiments, but these dimensions and sizes are not intended to be limiting. For example, various embodiments provide for expansion of the distal end to a diameter (d) of about 20 mm to about 35 mm. Also, the relative size or length of the distal end can be selected to provide suitable expansion. In this embodiment, the distal end comprises a cut out area 330 sized so that a fixation 140 element can pass through the cut out area 330.

For example, the cut out 330 may have a height (c) from about 10 mm to about 20 mm and a width (e) from about 5 mm to about 20 mm in certain embodiments. In this embodiment, a cut out area 330 is shown on one side of the access device 300. In other embodiments, cut out areas 330 may be included on both sides, or on other portions of the distal end.

The tube portion 320 has a proximal end, which in some embodiments, has an inner diameter (b) in a range from about 12 mm to about 20 mm. In certain embodiments, the tube portion may contain a cut out area on a side of the tube opposite to the distal end. The tube portion may have a length that permits the proximal end to extend outside the body when the distal end of the retractor is adjacent a vertebral target location. The length (a) of the expanding access device 300, from the distal end to the proximal end of the tube portion 320 may be in a range from about 50 mm to about 120 mm in various embodiments. Other sizes, lengths, and diameters are possible.

Figure 11A:
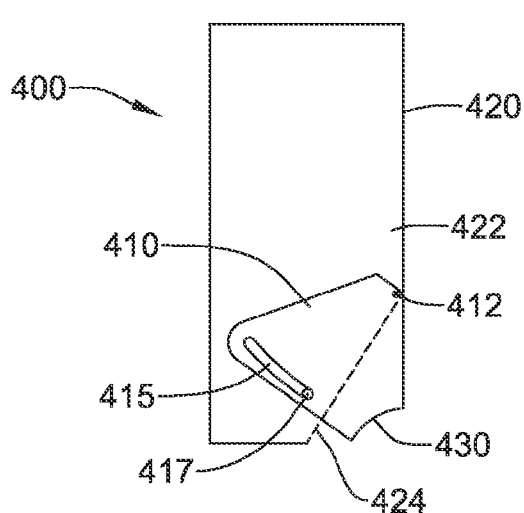
Figure 11B:
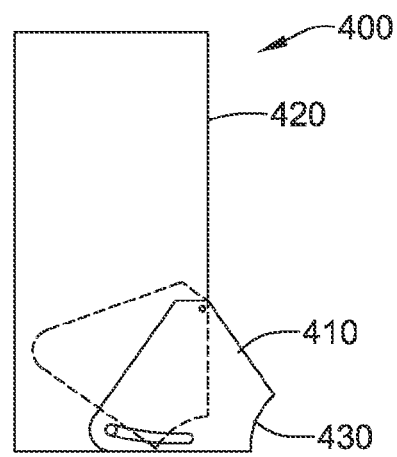
Figure 11C:
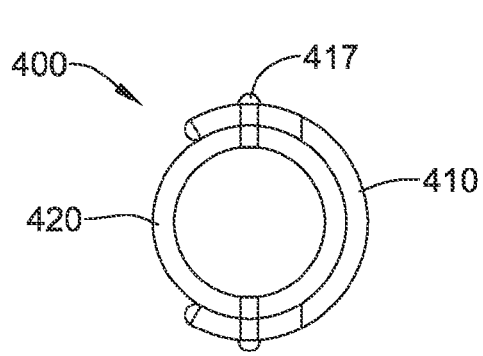
Figure 11D:
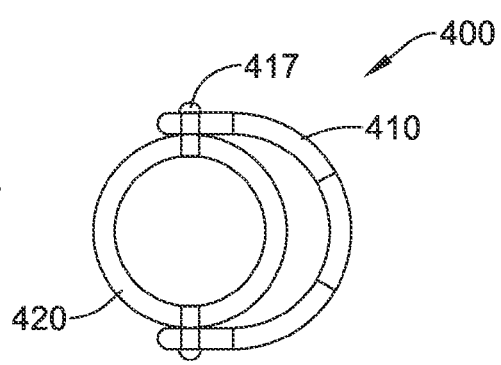

FIGS. 11A-11D schematically illustrate an alternate embodiment of an expanding access device 400 comprising a tube portion 420 and a distal skirt 410 that is pivotally connected to the tube portion 420. FIGS. 11C and 11D are end views of FIGS. 11A and 11B, respectively. The tube portion 420 is elongated and comprises a wall 422 that is generally cylindrical in cross-section. The wall 422 defines a passageway that extends therethrough to permit passage of implants and instruments. A portion of the distal end of the wall 422 is cut off to permit access in an expanded configuration. The skirt 410 overlaps the cut off portion 424 of the distal end of the wall 422 and is pivotally attached to the tube portion 420 by, e.g., one or more rivets 412. In some embodiments, the skirt 410 comprises at least one arcuate slot 415 that is configured to slide around a pin 417 disposed on the tube portion 420 (FIGS. 11A, 11B). In a contracted configuration (FIGS. 11A, 11C), the skirt 410 is pivoted inward toward the tube portion 420 so that the pin 417 is adjacent one end of the arcuate slot 415. In an expanded configuration (FIGS. 11B, 11D), the skirt is pivoted outward about the rivet, away from the tube portion, such that the pin is adjacent the opposite end of the arcuate slot. Accordingly, in the expanded configuration the distal end of the access device 400 has a larger cross-sectional area than in the contracted configuration.

In certain embodiments, the skirt 410 comprises one or more openings 430 or cut out areas (e.g. "channels" or "mating openings" and/or "laterally facing openings" that permit at least a portion of a fixation element to pass therethrough. The cut out area 430 is formed in a region of the skirt 410 that pivots farthest away from the tube portion 420. The cut out area 430 can have any suitable shape and size to permit passage of the fixation element. The alternate expanding access device schematically shown in FIGS. 11A-11D generally has dimensions similar to the expanding access device 300 schematically illustrated in FIGS. 9-10.

Figure 12A:
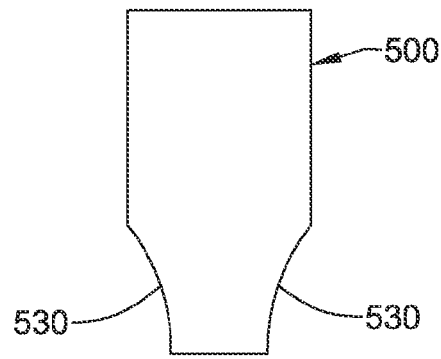
Figure 12B:
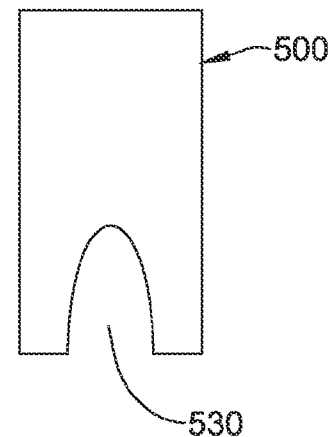
Figure 12C:
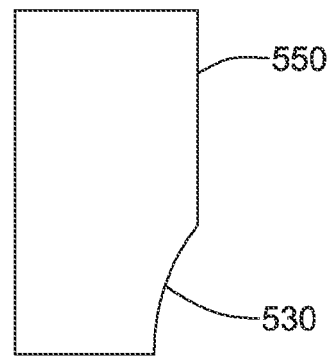

FIGS. 12A-12C schematically illustrate embodiments of non-expanding access devices 500, 550. FIGS. 12A and 12B illustrate access devices 500 with cut outs 530 (e.g. "channels" or "mating openings" and/or "laterally facing openings") on two sides, whereas FIG. 12C illustrates an access device 550 with a single cut out 530 on one side. In these embodiments, the cut out 530 has a generally upside-down "U"-shaped cross-section. Other cross-sectional shapes are possible. For example, FIG. 10 illustrates a cut out 330 with more rounded corners. In yet other embodiments, the cut out can be, for example, circular, oval, triangular, or rectangular. Access devices with cut outs on two sides are particularly suitable as a center access device in a multilevel procedure.

Additional embodiments of devices and components can be used for these or other procedures on the spine. For example, some of these procedures may be single- or multi-level fixation or fusion procedures at target locations on or near the vertebrae. In certain procedures, at least part of the procedure is performed percutaneously. Other parts of the procedure may be performed minimally invasively, e.g., through an access device.

B. Methods a Devices for Spinal Access Using a Multipurpose Tool

Figure 13:
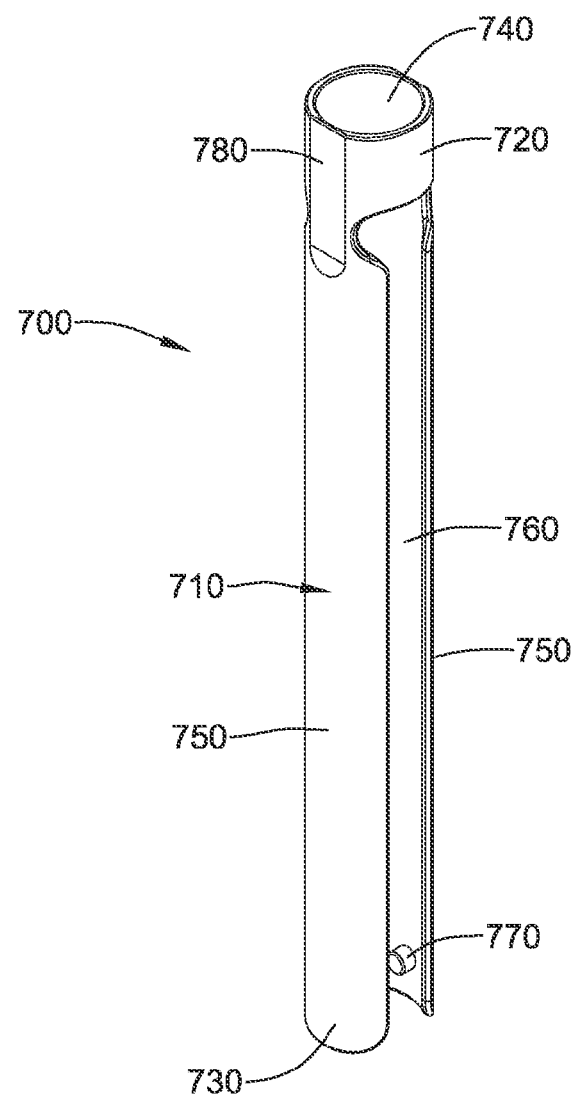
FIGS. 13-14 are perspective views that schematically illustrate embodiments of a multipurpose tool and related apparatuses that can be used in surgical procedures.
Figure 14:
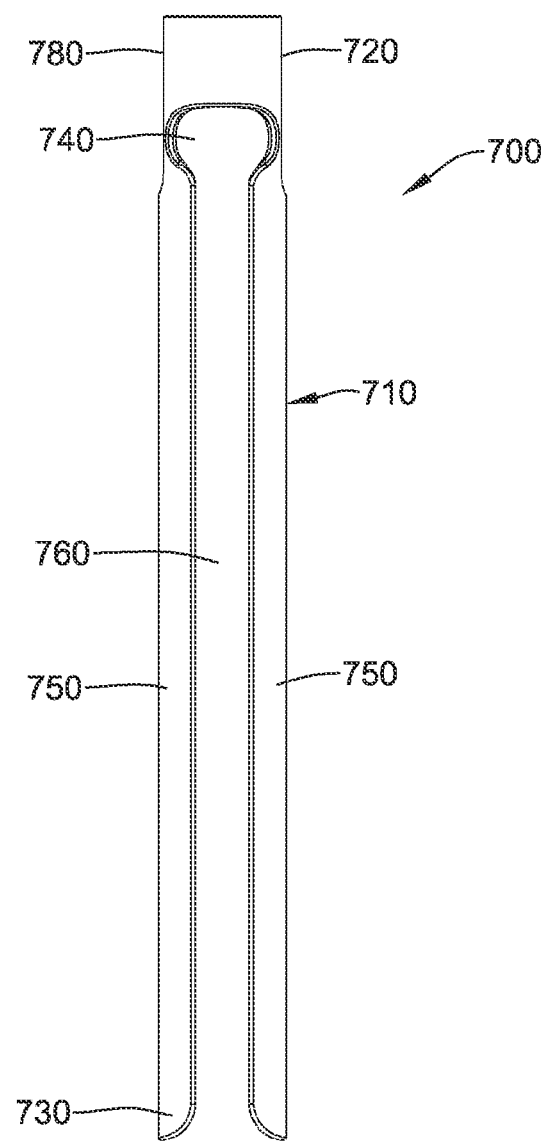

FIGS. 13 and 14 schematically illustrate a multipurpose tool 700 that can be used with any of the procedures discussed herein. For example, the multipurpose tool 700 can be used for purposes such as to assist installation of fasteners onto target sites and/or to assist guiding a fixation element (e.g., a fixation rod) into engagement with the fasteners. Although in some procedures, embodiments of the multipurpose tool 700 are used for several purposes, it is recognized that in other procedures, embodiments of the multipurpose tool are used for only a single purpose. Accordingly, a skilled artisan will understand that an embodiment of the multipurpose tool 700 can be configured for one purpose or for two purposes or for three or more purposes in various techniques, and the multipurpose tool 700 is not to be limited only to those embodiments configured for more than one purpose.

In some embodiments, the multipurpose tool 700 comprises an elongate body 710 with a proximal end 720 and a distal end 730. The elongate body 710 defines a bore or passageway 740 between the proximal and distal ends of the tool. In certain embodiments, the elongate body 710 comprises a generally cylindrical portion at the proximal end 720 of the tool and at least two arms 750 that extend from the cylindrical portion toward the distal end 730 of the tool. The arms 750 are spaced apart from each other and define elongated slots 760 therebetween. In some embodiments, the slots 760 extend substantially along the length of the elongate body 710. The multipurpose tool 700 may have a transverse cross-section that is generally circular, and the arms 750 have corresponding arcuate cross-sections. In some embodiments, the arms 750 have substantially similar shapes and sizes and the slots 760 are symmetrically disposed about the circumference of the elongate body 710. In certain embodiments, the multipurpose tool 700 comprises two arms 750 that define a pair of opposed slots 760. In some embodiments, the width of each of the slots 760 measured circumferentially is typically less than the width of each the arms 750. Although two arms 750 and two slots 760 are shown in FIGS. 13-14, in other embodiments a different number of arms is used such as, for example, three arms, four arms, or five arms. Further, in some embodiments, the length of each of the slots may be different. For example, one of the slots may extend substantially along the length of the tool, while another slot may be shorter.

The multipurpose tool 700 generally is fabricated from a substantially rigid material such as a metal or a plastic. The material should be sufficiently flexible and/or resilient so that the arms 750 tend to return to their initial position after a displacement. In some embodiments, the tool is fabricated from titanium or stainless steel, although other metals can be used such as, for example, nitinol.

Figure 15:
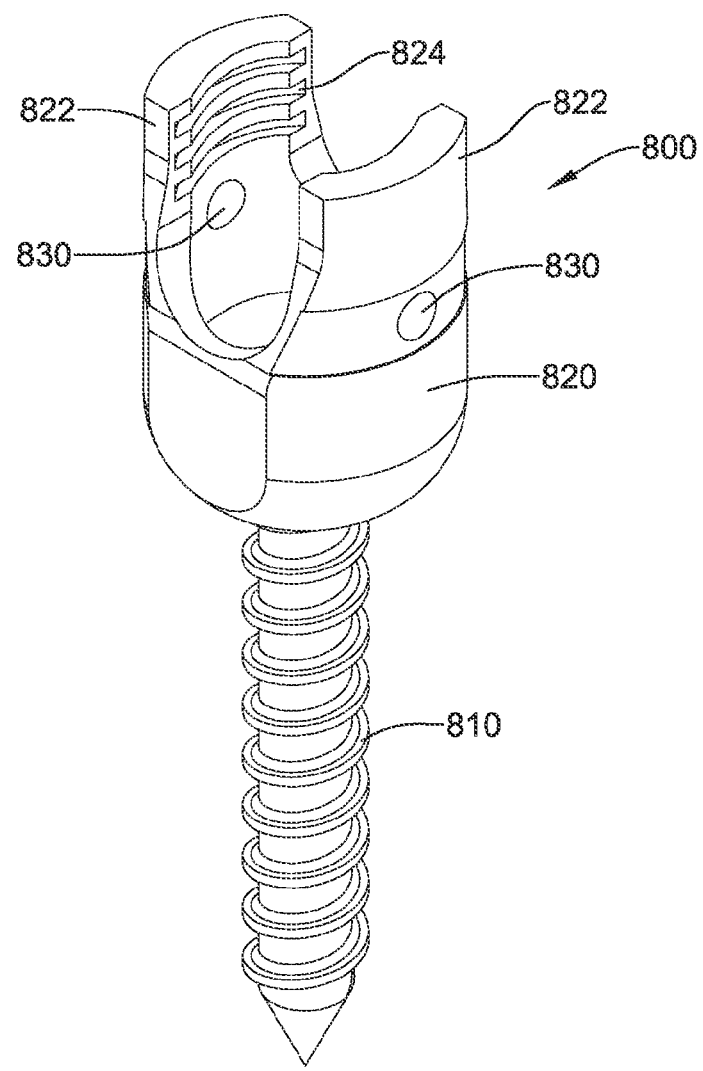
FIG. 15 is a perspective view of an embodiment of a fastener.

In certain procedures, the multipurpose tool 700 is used to grasp and hold other devices or components. For example, in the embodiment shown in FIGS. 13-14, the distal end 730 of the multipurpose tool 700 has a protrusion 770 (FIG. 13)

configured to engage a fastener such as, for example, a pedicle screw assembly. The multipurpose tool 700 can be used to deliver the fastener to a target location on the spine of a patient through, for example, a percutaneous path or channel formed in the tissue of the patient. FIG. 15 illustrates an embodiment of a fastener 800.

Figure 16:
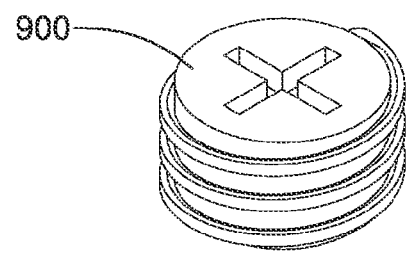
FIG. 16 is a perspective view of an embodiment of a cap screw.

The fastener 800 may be used as a bone anchor such as, for example, a pedicle screw, although in other embodiments, the fastener 800 may be configured for attachment to other vertebral landmarks such as, for example, a facet joint, a transverse or spinous process, or other suitable location. As shown in FIG. 15, the fastener 800 comprises a screw portion or shaft 810 and a head or housing 820. The shaft 810 has a distal threaded portion configured to be inserted into a hole, which may be tapped, in the vertebra at the target location. The head 820 is attached to a proximal end of the shaft 810 and is configured to receive a fixation element (e.g., a fixation rod). In one embodiment, the head 820 comprises two flanges 822 that define a generally "U"-shaped opening formed therebetween. In use, a portion of the fixation element is placed in the U-shaped opening between the flanges 822 and is secured by, for example, a cap screw or set screw 900 (FIG. 16). As shown in FIGS. 15-16, an inner surface 824 of the head 820 may be threaded to receive the externally threaded cap screw 900, which is screwed into the head 820 so as to secure the fixation element within the head. In some embodiments, the fastener 800 is cannulated, e.g., it has an internal lumen configured for a guidewire or the like to pass therethrough so that it may be delivered to the target location.

In other embodiments, the head comprises a housing having a first passage configured to receive a screw portion and a second passage with a longitudinal axis extending transverse to the first passage. The screw portion extends through an opening in the housing into the second passage and is movable to the housing. For example, the screw portion can be positioned in any of a plurality of desired angular positions with respect to the longitudinal axis of the second passage. Further details of fasteners suitable for use with the systems and methods disclosed herein can be found in U.S. patent application Ser. No. 11/415,676, filed May 2, 2006, titled "METHODS FOR CONNECTING A LONGITUDINAL MEMBER TO A BONE PORTION," which is hereby incorporated by reference in its entirety and made part of this specification.

In some embodiments, the fastener 800 is configured to engage the multipurpose tool 700. For example, the head 820 may include one or more recess or detent feature 830 configured to mate with a corresponding protrusion 770 in the multipurpose tool 700. In the embodiment shown in FIG. 15, the detent feature 830 is a cylindrical hole through the flange 822 that is sized and shaped to mate with a corresponding cylindrical protrusion 770 formed on the inner surface of at least one of the arms 750 of the multipurpose tool 700. The depth of the detent feature 830 is generally about the same as the extent of the protrusion 770 on the inner surface of the arms 750. In other embodiments, the protrusion 770 can comprise a dimple, a bump, a ridge, or some other suitable shape. In some embodiments, each of the arms 750 of the multipurpose tool 700 includes a protrusion 770 that can mate with a corresponding detent feature 830 on the head 820 of the fastener 800. For example, in the embodiment show in FIG. 15, each flange 822 of the head 820 comprises a detent feature 830 that mates with a protrusion 770 on each of the arms 750. In other embodiments, the fastener 800 can be grasped by the multipurpose tool 700 via other mechanisms. For example, the distal ends of the arms may have a rim that is configured to engage a corresponding groove in the head. Many other variations are possible.

Figure 17:
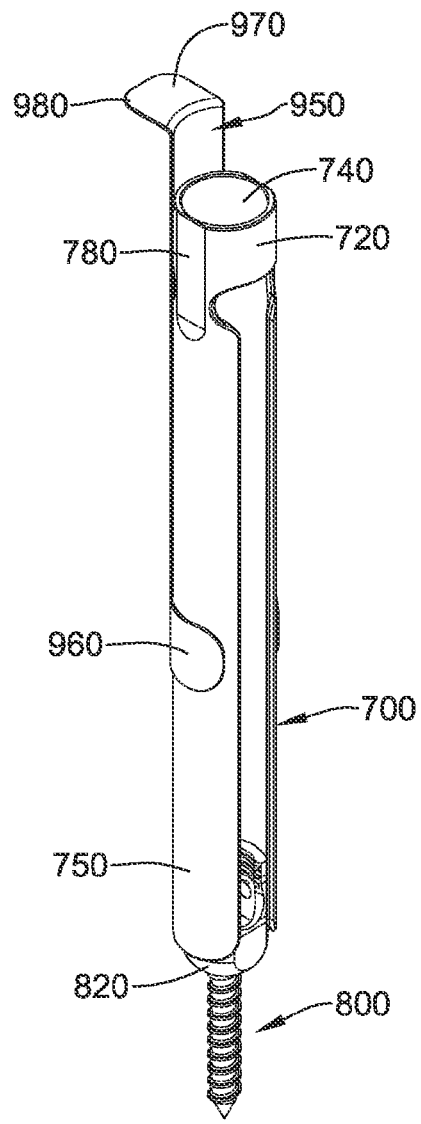
FIG. 17 is a perspective view of the embodiment of a multipurpose tool and fastener with the retaining clip of FIG. 18.

In one embodiment, coupling the fastener 800 to the multipurpose tool 700 involves the user grasping the multipurpose tool 700 and applying a force to urge the arms 750 slightly apart until the protrusions 770 can fit around the head 820 of the fastener 800. The user manipulates the position and orientation of the fastener until the detent features 830 on the head align substantially with the protrusions 770 on the arms 750, at which point the user releases the force on the arms 750, which move inward so as to permit the protrusions 770 to mate with the detent features 830. To release the fastener 800 from the multipurpose tool 700, the user applies a force to slightly spread the arms 750 so that the protrusions 770 disengage the detent features 830. The user may then separate the multipurpose tool from the fastener. In other embodiments, the head may include additional notches and/or grooves that permit the head of the fastener to be "snap-fit" into the distal end of the multipurpose tool. FIG. 17 illustrates the fastener 800 in place within the arms 750 of the multipurpose tool 700. Although FIG. 17 illustrates the multipurpose tool 700 engaging a fastener 800, it is contemplated that the multipurpose tool 700 can be used to engage other devices, components, and/or tools.

The inner diameter of the bore 740 formed within the multipurpose tool 700 may be selected to be approximately the same diameter as the head 820 of the fastener 800. In some embodiments the inner diameter is slightly larger than the diameter of the head of the fastener, while in other embodiments the inner diameter is slightly smaller. In one embodiment, the inner diameter of the multipurpose tool is about half an inch, and the outer diameter of the multipurpose tool is approximately 0.6 inches. In a further embodiment, the inner diameter is approximately 0.527 inches, and the outer diameter is approximately 0.625 inches. The length of the multipurpose tool 700 depends in part upon the depth of the target location below the skin of the patient. For example, the length of the tool is selected so that the proximal end 720 of the tool extends above the skin of the patient when the distal end 730 of the tool is adjacent the target location. In various embodiments, the length of the multipurpose tool 700 is in a range from about 2 inches to about 5 inches, although other lengths can be used.

Figure 18:
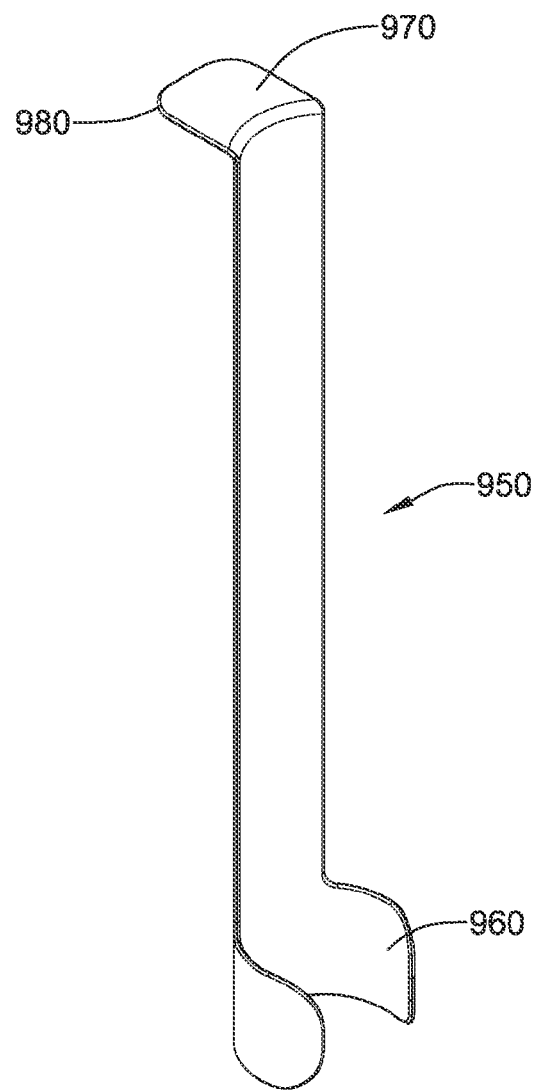
FIG. 18 is a perspective view of an embodiment of a retaining clip.

FIG. 18 schematically illustrates an optional retaining clip 950 that may be used with the multipurpose tool 700. The retaining clip 950 comprises an elongated body having a "C"-shaped clip portion 960 at a distal end and a handle portion 970 at a proximal end. The elongated body and the "C"-shaped clip 960 may be configured to slidably engage the multipurpose tool 700. In some embodiments, the clip portion 960 has an inner diameter that is slightly larger than the outer diameter of the multipurpose tool so that the clip portion 960 can be pushed onto the proximal (or distal) end of the tool. The circumferential extent and the length of the "C"-shaped clip portion 960 are large enough to provide suitable frictional coupling to hold the retaining clip in place on the tool. The cross sectional shape of the clip portion 960 and the elongated body may be selected to conform to the cross-sectional shape of the multipurpose tool 700 to provide a suitably secure engagement therebetween. In some embodiments, this cross sectional shape is substantially circular, which permits the retaining clip to be rotated into any desired orientation around the longitudinal axis of the multipurpose tool. In the embodiment shown in FIG. 18, the handle portion 970 of the retaining clip 950 comprises a tab 980 that is offset from, and may be substantially orthogonal to the elongated body and which can be used to push or to pull the retaining clip 950 into a desired position along and around the multipurpose tool 700. The retaining clip 950 may be fabricated from a substantially rigid and durable material such as a metal or a plastic. In some embodiments the retaining clip 950 is formed from stainless steel or titanium.

FIG. 17 schematically illustrates the multipurpose tool 700 engaged with the retaining clip 950 and fastener 800. The retaining clip 950 has been pushed toward the distal end of the tool such that the "C"-shaped clip portion is near the distal end of the tool 700. The retaining clip 950 can be used to secure the arms 750 of the multipurpose tool 700 around the fastener 800 to be delivered to a target location. Use of the clip 950 beneficially reduces the possibility that the arms of the multipurpose tool 700 will spread apart as the tool is delivered to the target location through a path between the skin and the spine. Additionally, use of the clip 950 reduces the possibility that the fastener 800 will be dislodged from between the arms as it is advanced along a percutaneous path. In some procedures, after the fastener 800 has been delivered to the target location, the retaining clip 950 can be slid upward toward the proximal end of the tool 700 so as to permit the arms to release the fastener. In certain procedures, the retaining clip 950 is completely disengaged from the multipurpose tool 700 after the fastener is delivered to the target location.

The retaining clip 950 provides additional benefits. In certain fixation procedures, a portion of a fixation element (e.g., a fixation rod) is disposed within the head of a fastener 800 (e.g., within the "U"-shaped opening shown in FIG. 15) and then secured into position (e.g., with a cap screw 900). In some of these procedures, after the fixation element has been delivered adjacent the head of the fastener (e.g., generally near or between the flanges defining the opening), the retaining clip 950 advantageously can be used to push the fixation element toward the distal portion of the "U"-shaped opening and to assist seating it in the head. Additionally, the retaining clip can hold the fixation element in place while the cap screw is tightened.

FIGS. 13 and 18 schematically illustrates the proximal end 720 of the multipurpose tool 700 and the distal end of the retaining clip 950 (e.g., the "C"-shaped clip portion). In some embodiments, the circumferential extent of the "C"-shaped clip portion 960 is sufficiently large that it slides onto the proximal end 720 of the tool 700. However, in other embodiments, the circumferential extent of the "C"-shaped clip portion is smaller, which permits the retaining clip to be clipped or snapped onto the tool. In other embodiments, the retaining clip and/or the multipurpose tool include a locking feature configured to prevent the retaining clip from sliding when the locking feature is activated. In some embodiments, the locking feature comprises one or more detents that permit the retaining clip to be locked in selected locations.

Figure 19:
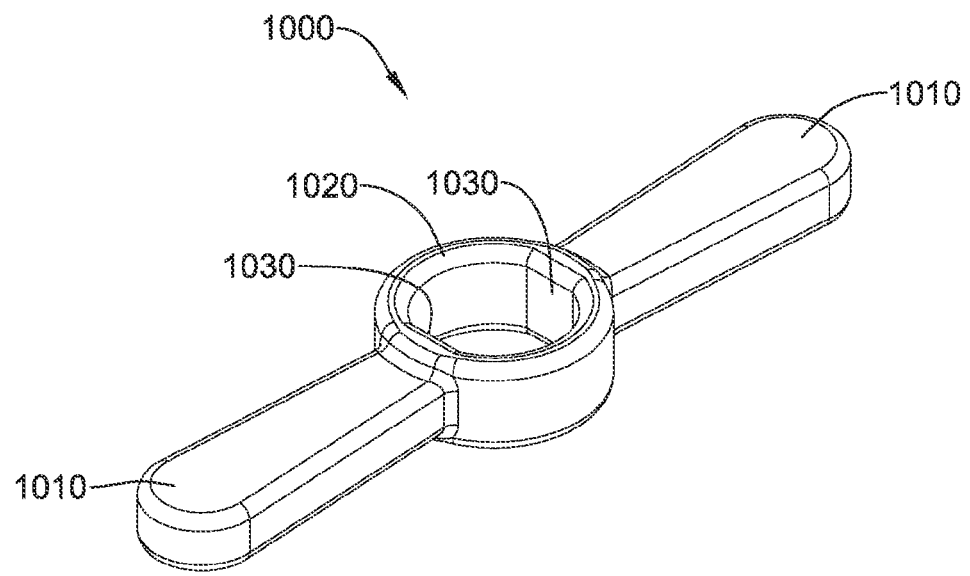
FIG. 19 is a perspective view of an embodiment of an anti-torque handle that can be used with the multipurpose tool illustrated in FIGS. 13-14.

In some procedures, to secure a fastener to a target location in the spine, an instrument such as a screwdriver is used to apply a torquing or twisting force to, for example, the shaft 810 of the fastener 800. It may be beneficial to reduce transfer of the twisting force to other devices or locations including, for example, the multipurpose tool, adjacent vertebral bodies, surrounding tissue, etc. In some procedures, transfer of the twisting force is reduced by applying a counter-torque to the multipurpose tool. FIG. 19 is a perspective view of an embodiment of an anti-torque handle 1000 that can advantageously be used secure the multipurpose tool 700 while a fastener 800 is being tightened. The anti-torque handle 1000 comprises a pair of elongated arms 1010 extending axially away from a central ring portion 1020 configured to engage the proximal end 720 of the multipurpose tool 700. The elongated arms 1010 are sufficiently long so as to enable a surgeon to apply a sufficient counter-torque while tightening the fastener 800. In the embodiment shown in FIG. 19, the central ring portion 1020 has an inner surface that defines a central passage that has a size and shape selected to permit the proximal end 720 of the multipurpose tool 700 to pass therethrough. The anti-torque handle 1000 is adapted to reduce relative rotation between the handle and the multipurpose tool after the handle engages the tool. For example, in some embodiments, the outer surface of the proximal end of the multipurpose tool and the inner surface of the anti-torque handle are configured with correspondingly shaped surfaces that minimize relative rotation. In the embodiment shown in FIG. 19, these surfaces comprise facets 1030 on the inner surface of the central ring portion 1020 of the anti-torque handle 1000 that engage corresponding facets 780 on the proximal end 720 of the multipurpose tool 700 when the handle is placed onto the proximal end of the tool. In other embodiments, a different number of facets can be used. For example, in certain embodiments the proximal end of the tool and the inner surface of the handle are hex-shaped. The facets have a longitudinal extent that can be selected so that the anti-torque handle can be disposed at a suitable position along the multipurpose tool. The anti-torque handle can slide along the tool until the lower portion of the handle engages the lower portion of the facet, which forms a ledge to support the handle. In other embodiments, the handle can be secured to the tool using other mechanisms such as, for example, via one or more deeds, clips, tongue-and-grooves, etc.

The anti-torque handle may provide additional advantages to those described above. For example, it can be disposed on the multipurpose tool and used to move, rotate, advance, and/or orient the multipurpose tool. In some procedures, the anti-torque handle is grasped by the surgeon and used to advance the multipurpose tool through the percutaneous tissue path to target location.

Figure 20:
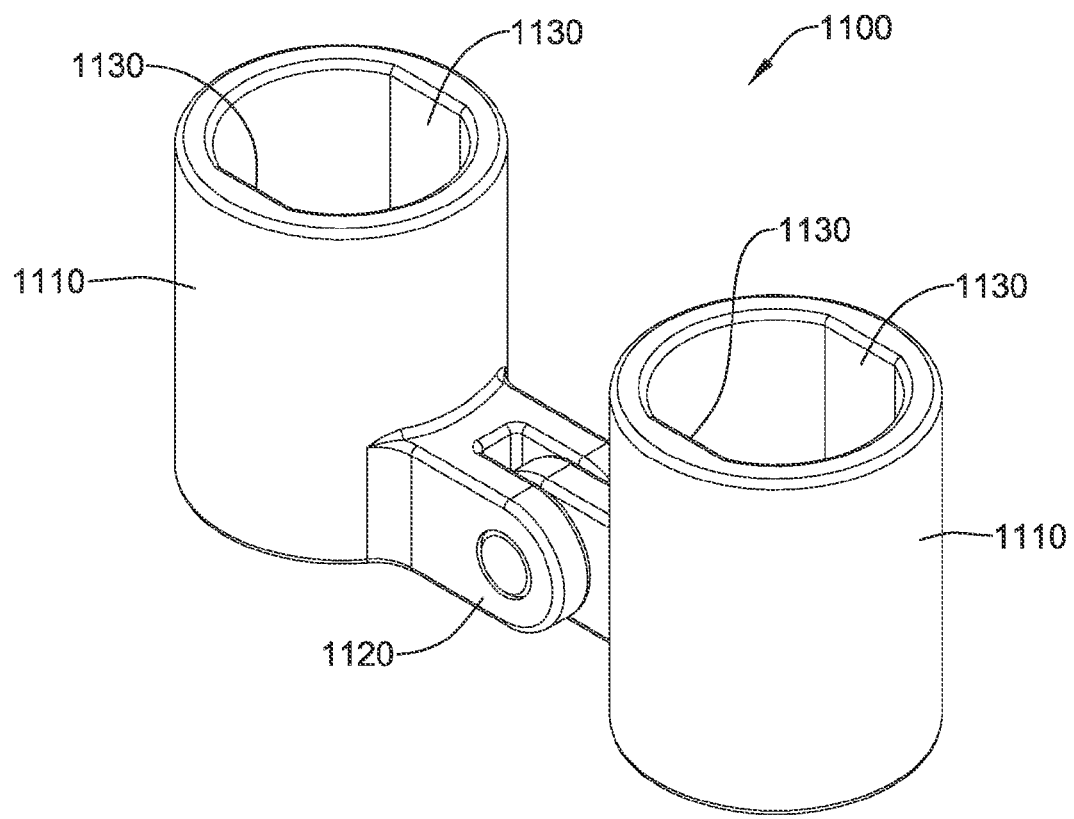
FIG. 20 is a perspective view of an embodiment of a compression/distraction link assembly.
Figure 21:
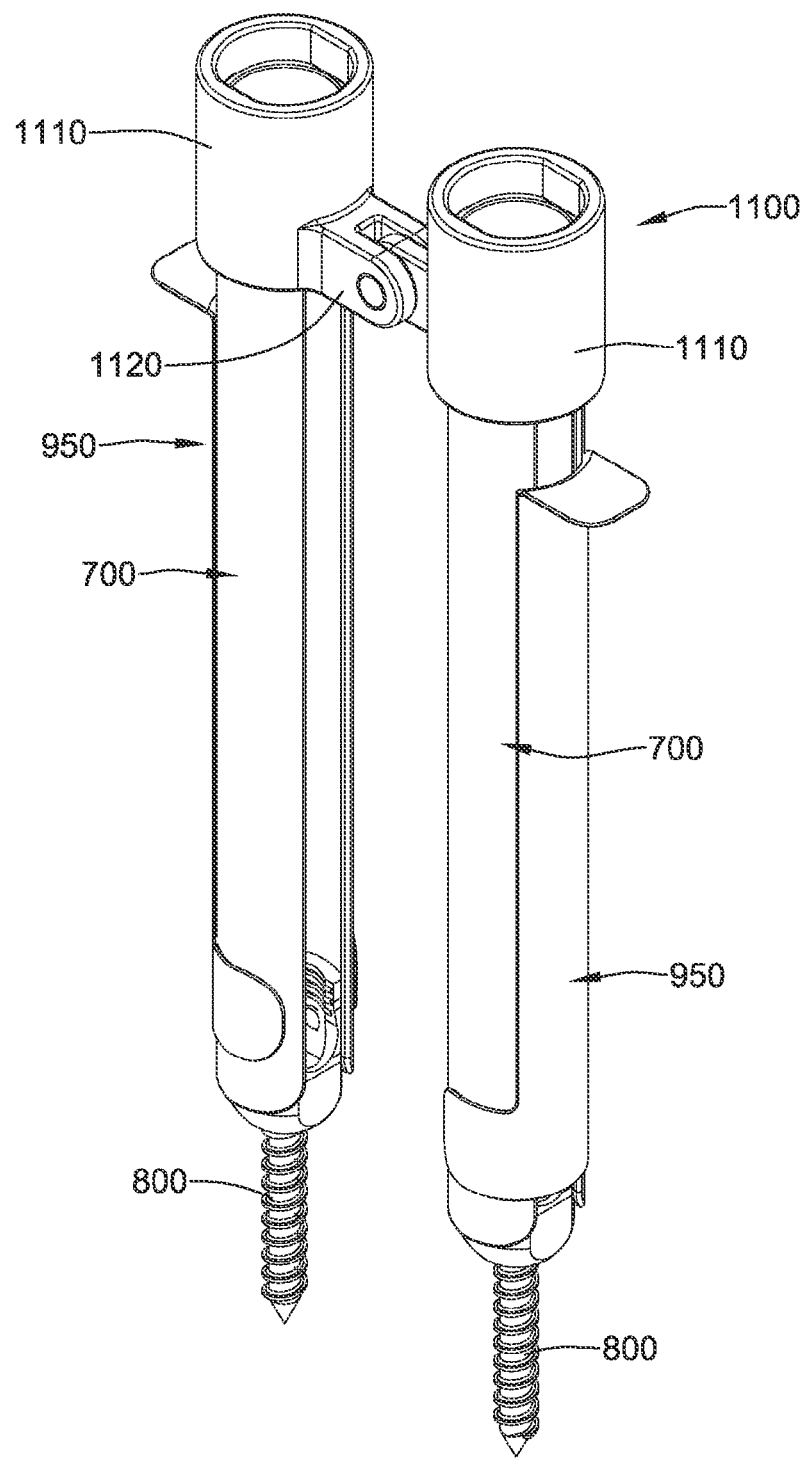
FIG. 21 is a perspective view of the embodiment of the compression/distraction link assembly of FIG. 20 in place on a pair of multipurpose tools.

FIG. 20 is a perspective view that schematically illustrates an embodiment of a compression/distraction link assembly 1100 configured to receive the proximal ends of two adjacent multipurpose tools 700. FIG. 21 is a view that schematically shows the link assembly 1100 disposed Oil the proximal ends of two adjacent multipurpose tools 700. The compression/distraction link assembly 1100 generally comprises two elongated bodies 1110 that are pivotally coupled about a pivot joint 1120. The elongated bodies 1110 have a proximal and distal end, and in some embodiments, the elongated bodies are generally cylindrical in shape. The elongated bodies may have any suitable length including, for example, about 1 inch. Each of the elongated bodies has an inner surface that defines a passage therethrough. The inner diameter of the passage is generally slightly greater than the outer diameter of the proximal end of the multipurpose tool. The inner surface may include one or more facets 1130 configured to engage with facets 780 on the proximal end of the multipurpose tool 700. In certain embodiments two opposing facets are used; however, other numbers of facets can be used (e.g., six facets in a hex configuration). In some embodiments the facets 1130 extend the entire length of the elongated bodies 1110, which enables either the proximal or the distal end of the elongated body 1110 to be disposed onto the multipurpose tool 700. The pivot joint 1120 may comprise a pin joint that permits rotational motion about an axis through the pin. In other embodiments, a pin-in-slot joint may be used to additionally provide limited translation motion between the elongated bodies.

The compression/distraction link assembly 1100 can be used with two multipurpose tools 700 to compress or distract adjacent vertebral bodies in the cephcaudal direction during, for example, a fixation or fusion procedure. By applying suitable forces to one or both of the multipurpose tools, the tools can pivot around the pivot joint such that the distal ends of the tools can be moved toward each other (for compression) or away from each other (for distraction). FIG. 21 is a perspective view that schematically illustrates an example position of the tools 700 in a distraction procedure. In some procedures, to pivot one (or both) tools 700, an instrument can be inserted into the passageway within one (or both) of the elongated bodies 1110 of the link assembly 1100, and a suitable pivoting force can be applied. In certain procedures, a multipurpose tool 700 can be used as the instrument, e.g., the cylindrical portion of the proximal end of the tool 700 can be inserted into the link assembly 1100 and a pivoting force can be applied to the opposing end of the tool 700. However, any other suitable elongated instrument can be used including, for example, a dilator or obturator.

Figure 22:
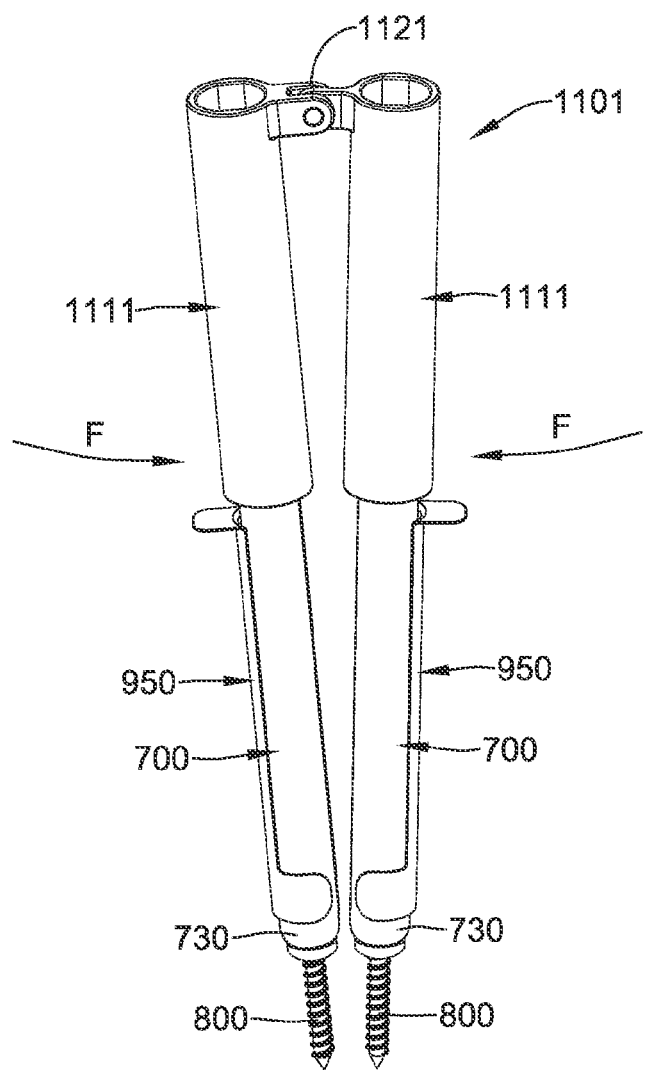
FIGS. 22-23 are perspective view of another embodiment of compression/distraction link assembly in place on a pair of multipurpose tools.
Figure 23:
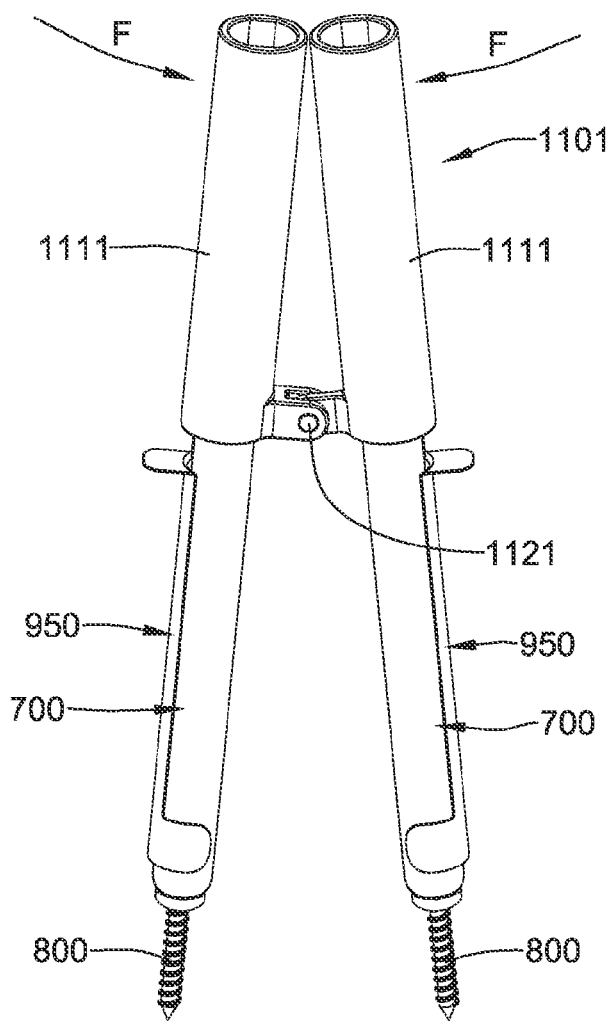

FIGS. 22 and 23 are plan views that schematically illustrate another embodiment of the compression/distraction link assembly 1101. In this embodiment, the length of the elongated bodies 1111 is greater than in the embodiment shown in FIG. 20. In some embodiments, the length of the elongated bodies 1111 is in a range from 1 inch to about 8 inches. In one embodiment, the length is about 6 inches. FIG. 22 schematically illustrates how the link assembly can be used in a compression procedure. A force F can be applied so as to push the elongated bodies 1111 of the link assembly 1101 together. The elongated bodies pivot about the pivot joint 1121 (which is disposed proximal to the surgeon), causing the distal ends 730 of the multipurpose tools 700 to move toward each other. Accordingly, fasteners 800 inserted in vertebral bodies will cause the bodies to shift toward each other. Although the force F is shown as applied to the link assembly 1101, the force F may additionally and/or optionally be applied at any suitable position distal to the pivot joint. In some procedures, a surgeon applies the force F by squeezing together the elongated bodies 1111 of the link assembly. The force F can be applied to shift the vertebral bodies into suitable positions before securing a fixation assembly (e.g., before tightening cap screws onto fixation rods).

FIG. 23 schematically illustrates how the link assembly 1101 can be used in a distraction procedure. In this procedure, the link assembly 1101 is oriented so that the pivot joint 1121 is disposed distal to the surgeon and adjacent the proximal ends 720 of the multipurpose tools 700. In some embodiments, the link assembly 1101 shown in FIG. 22 is inverted so that its opposite end is disposed on the multipurpose tools, as shown in FIG. 23. As shown in FIG. 23, when a force F is applied proximal to the pivot joint, e.g., by squeezing the elongated bodies 1111 of the link assembly together, the distal ends of the multipurpose tools move apart. Accordingly, the fasteners cause a distraction of the vertebral bodies in which the fasteners are seated.

The embodiment of the link assembly shown in FIGS. 22 and 23 advantageously can be used in either a distraction or a compression procedure. The link assembly beneficially provides ease of use, because in both procedures, the surgeon need only apply a squeezing force of suitable magnitude to accomplish the desired compression or distraction. In certain embodiments, the link assembly includes a locking feature that holds the link assembly in a suitable compression or distraction position after the force F is removed. In some embodiments the locking feature comprises a locking element having a pair of generally "C"-shaped clips that clip or snap on to each of the elongated bodies of the link assembly to hold them in a desired orientation. In other embodiments, the locking feature comprises a tether.

Figure 24:
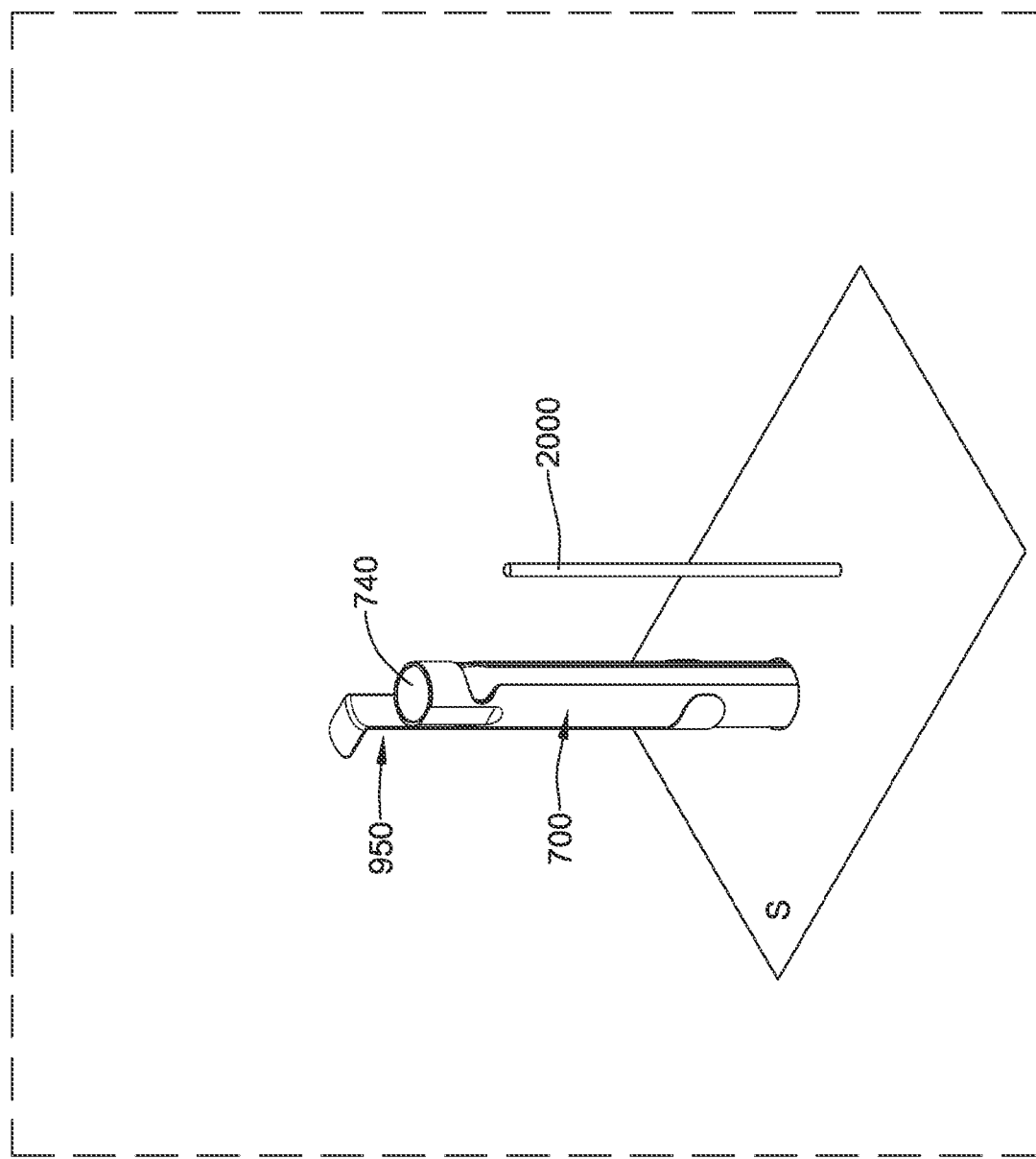
FIGS. 24-25 schematically illustrate various stages of an embodiment of a spinal procedure.
Figure 25:
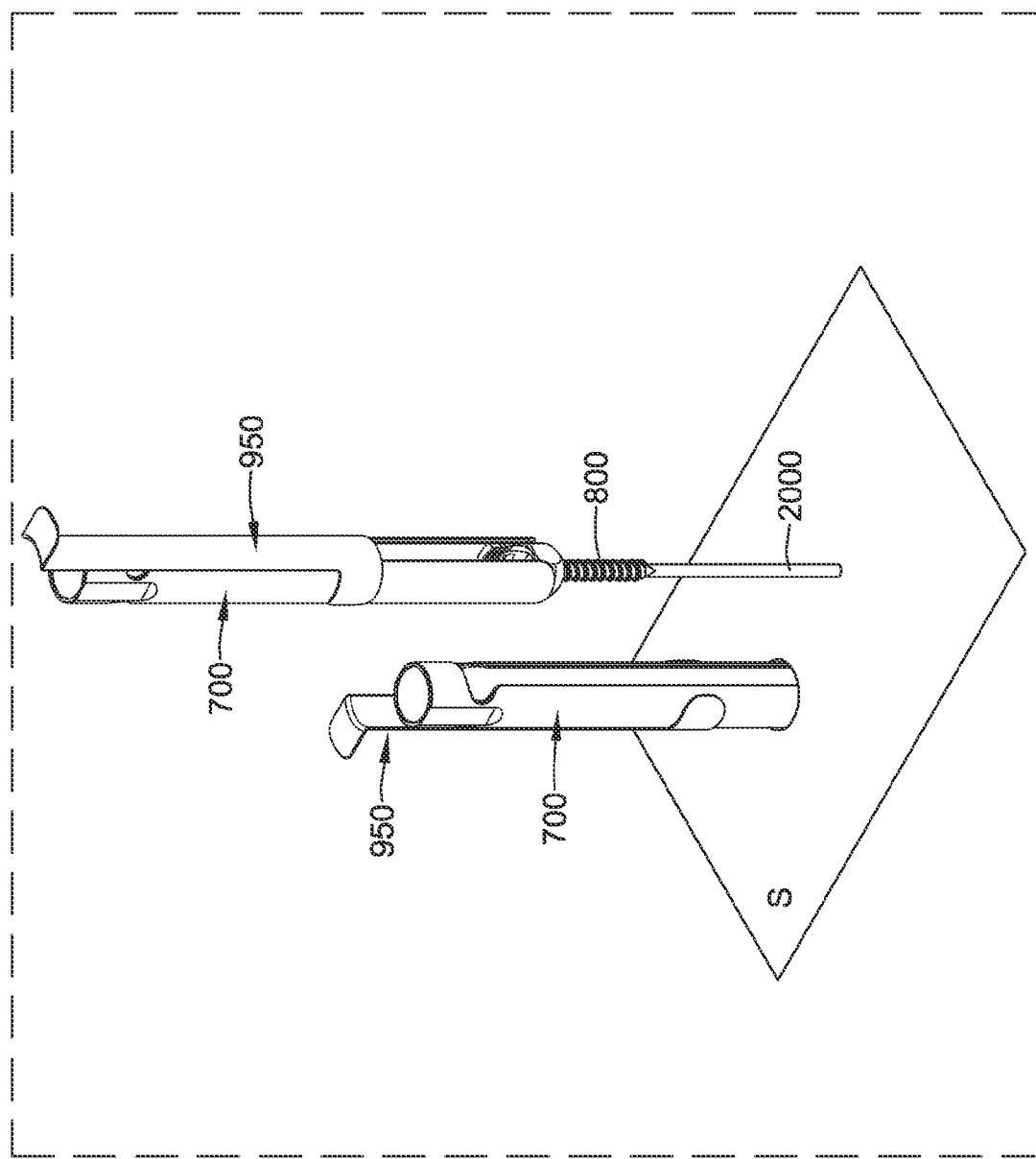

FIGS. 24 and 25 schematically illustrate certain acts that may be performed during various embodiments of procedures used to treat the spine of a patient. FIG. 24 shows a multipurpose tool 700 that has been inserted into a percutaneous path or entry between the skin S and a target location adjacent a vertebral body. In some procedures the multipurpose tool is inserted over a dilator or through an access device, which may subsequently be removed. The multipurpose tool generally is used to deliver a fastener to the target location. An instrument, such as a hex tool or screwdriver, can be inserted into the central bore 740 defined by the arms of the multipurpose tool. The instrument can be used, for example, to screw the fastener into the bone at the target location. FIG. 24 also shows a guidewire 2000 inserted into an adjacent percutaneous path to an adjacent target site. A surgeon may use the instrument, for example, to advance the fastener into the vertebral body. One hand of the surgeon applies a counter-torque to the multipurpose tool by, for example, firmly grasping an anti-torque handle disposed on the proximal end of the tool.

At a later stage of the procedure, the guidewire is removed and a second multipurpose tool is inserted into the adjacent opening to deliver a fastener to the adjacent target location. An instrument, such as a hex tool or screwdriver, is inserted into the second multipurpose tool in preparation for tightening the fastener. An anti-torque handle may be disposed on the second multipurpose tool. An instrument such as an endoscopic screwdriver may be used to advance a clamping member (e.g., a cap screw) through the multipurpose tool to the head of the fastener disposed at the distal end of the tool. It is understood that additional and/or different acts can be performed in different procedures and that not all the illustrated acts are performed in all procedures. For example, in some procedures a target location is prepared by forming a threaded opening with a bone probe and/or bone tap. Hardware components, such as a fixation or fusion element, may be delivered to the target location through, for example, a percutaneous path and/or other incisions. In certain procedures, an access device may be used during certain acts of the procedure. Many variations are possible.

In certain procedures, one or more multipurpose tools can be used to assist installing fasteners (such as pedicle screws) and fixation elements (such as fixation rods) at target locations on the spine. In certain such procedures, the multipurpose tool advantageously provides guidance in delivering the fastener and/or the fixation element to the target location. As an example of the some of the advantages provided by a multipurpose tool, an embodiment of one percutaneous fixation procedure will now be described.

Under fluoroscopy, a trocar and needle (such as a Jamshidi targeting needle or a bone biopsy needle) are percutaneously passed through the skin and tissue of the patient to a target location on the spine of the patient (e.g., a pedicle). A guidewire is inserted through the Jamshidi targeting needle and advanced to the target location. Using fluoroscopy, a distal end of the guidewire is tamped into the vertebral body. These acts may be repeated for as many target sites as desired. Short incisions are made on opposite sides of the guidewire to assist dilation of the percutaneous path. The incisions are generally aligned with each other and may be about 5 mm in length. The percutaneous path is dilated by inserting a series of one or more dilators. The path may be dilated until a 40-mm diameter dilator has been used. The smaller dilators can be removed leaving the 40-mm diameter dilator and the guidewire in the percutaneous path. A cannulated tap is threaded over the guidewire and advanced to the target location. The tap can be used to tap the target location (e.g., to create a threaded hole in, for example, the pedicle). Fluoroscopy can be used to assist tapping the target location. After tapping is complete, the dilator and the tap can be removed, leaving the guide wire in the percutaneous path.

A cannulated fastener (e.g., a cannulated pedicle screw) is engaged at the distal end of a multipurpose tool. The guidewire is threaded through the cannulated fastener and the bore defined within the multipurpose tool. An instrument such as a hex wrench (e.g., a cannulated 3.5-mm hex wrench) can be used to assist threading the guidewire through the fastener. The distal end of the multipurpose tool is advanced through the percutaneous path to the target location. The distal end of a first multipurpose tool and a first fastener are disposed at the first vertebral site. The second guidewire is disposed at the second site. Under fluoroscopy, the fastener can be screwed into the bone at the target location using the hex wrench. The multipurpose tool is rotated so that the slots between the arms of the tool are aligned with an adjacent guidewire (or adjacent multipurpose tool). The anti-torque handle can be used to rotate the multipurpose tool. The above acts may be repeated so as to attach as many fasteners to target locations as desired.

A fixation element, such as a fixation rod, is delivered to the target location. For example, a rod holder can be used to grasp the rod and advance it to the spine. In some procedures, an additional incision that extends between the skin and the spine is made between adjacent sites to provide an access plane through the skin and tissue to the vertebral sites. In other procedures, a tissue tunnel or canal is formed between the target sites as further described below. Using fluoroscopy the fixation element is advanced through the multipurpose tool (and/or various incisions or canals) to the target site and positioned as needed, for example, between the first and second multipurpose tools. The fixation element is then secured to the fasteners, for example, by installing cap screws. In certain procedures, a 4.0-mm hex wrench is used to deliver the cap screw through the multipurpose tool and to tighten the cap screw to secure the fixation element into position at the target location. In one embodiment, a hex wrench is used for tightening the cap screw into the first fastener. A rod holder or other grasper apparatus is used for grasping the fixation rod between the two multipurpose tools to prevent twisting of the fixation rod as the cap screw is tightened. These acts are repeated as needed to secure one or more fixation elements to the spine of the patient. After the fixation rod is secured to the fasteners, the multipurpose tools are removed from the patient's body. Cap screws are then inserted into the heads of the first and the second fasteners and the fixation rod firmly secured therebetween. In other procedures, similar acts can be used to install additional fixation and/or fusion elements at vertebral sites. Additionally, similar acts can be used for multi-level procedures and for procedures at different vertebral sites such as, for example, facet joints and transverse or spinous processes.

FIGS. 24-25 show various stages of an example spinal procedure, such as a fixation or stabilization procedure. The example procedure shown in FIGS. 24-25 is a one-level procedure, but the acts and stages shown can also be applied to multi-level procedures. FIGS. 24-25 are intended to illustrate various stages of an example procedure but are not intended to be limiting with respect to the types of acts, methods, devices, and components that can be used.

First and second guidewires are percutaneously advanced through first and second percutaneous paths to a first and a second target location on the spine of the patient. In the view shown in FIG. 24, first and second guidewires 2000 have been inserted at first and second target locations, and a first multipurpose tool 700 has been inserted over the guidewire and advanced to the first target location. A cannulated instrument can then be disposed within the bore 740 defined within the multipurpose tool 700. When in use the cannulated instrument may have a handle that extends above the multipurpose tool. The instrument can be a hex wrench or a screwdriver configured to screw a fastener into the bone at the first vertebral site. FIG. 24 shows the surgical site after the cannulated instrument has been removed from the first multipurpose tool.

A series of dilators may then be used to expand the diameter of the second percutaneous path. In one procedure, three nested, cannulated dilators are used; however, a different number can be used in other procedures. The outermost dilator has an outer diameter of about ½ inch, and the outer diameter of the first multipurpose tool is about ¾ of an inch. In this procedure, the centers of the two adjacent percutaneous paths are spaced about 1.5 inches apart.

The dilators at the second site are then removed and an instrument such as, for example, a bone probe or a bone tap is advanced to the second vertebral site. The bone probe and/or bone tap can be used, for example, to form a threaded hole in the bone (e.g., in a pedicle). The instrument (e.g., the bone probe/tap) is then removed. As shown in FIG. 25, a cannulated fastener 800 (e.g., a cannulated pedicle screw) is disposed between the arms of a second multipurpose tool 700, and the fastener 800 is threaded over the guidewire 2000 in preparation for insertion into the second percutaneous path. A retaining clip 950 is attached to the second multipurpose tool 700 and is then slid toward the distal end of the tool to secure the fastener and to prevent the arms of the tool from spreading apart. In a subsequent stage of the procedure, the second multipurpose tool is advanced to the second vertebral site, the second guidewire is removed, and an instrument such as a hex wrench or screwdriver is inserted through the bore of the second tool to screw the second fastener into the bone at the second target location. At this stage of the procedure, the retaining clips on both multipurpose tools are retracted (e.g., pulled away from the spine).

In one embodiment, an incision is made between the two multipurpose tools, which extends from the skin to the target sites adjacent the spine. The incision is used to provide an access plane through which a fixation element (e.g., a fixation rod) can be advanced to the target site by, for example, a grasper apparatus. The fixation rod is manipulated by a grasper apparatus until each end of the rod is disposed within the heads of the first and second fasteners. As further described herein, the retaining clips can be slid downward (e.g., toward the spine) to assist in pushing and/or holding the ends of the fixation rod in place within the heads. A first cap screw is then advanced into the bore in the first multipurpose tool by an instrument such as a hex wrench. The surgeon tightens the first cap screw so as to secure the end of the rod at the first vertebral site. In some procedures, a compression or distraction procedure can be performed to shift the vertebrae into suitable positions. After the second cap screw is tightened, both multipurpose tools are removed.

Figure 26:
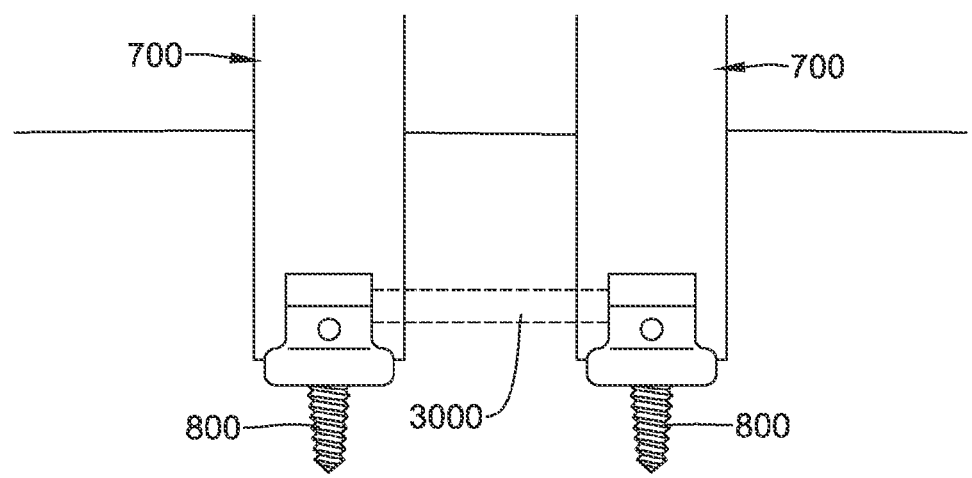
FIGS. 26-27 schematically illustrate an example of a formation of a tissue tunnel in a spinal procedure.
Figure 27:
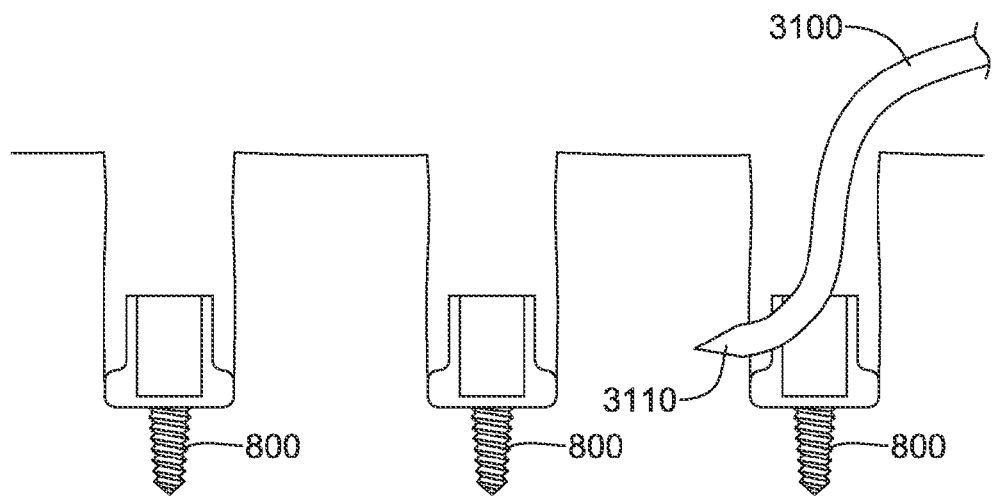
Figure 28:
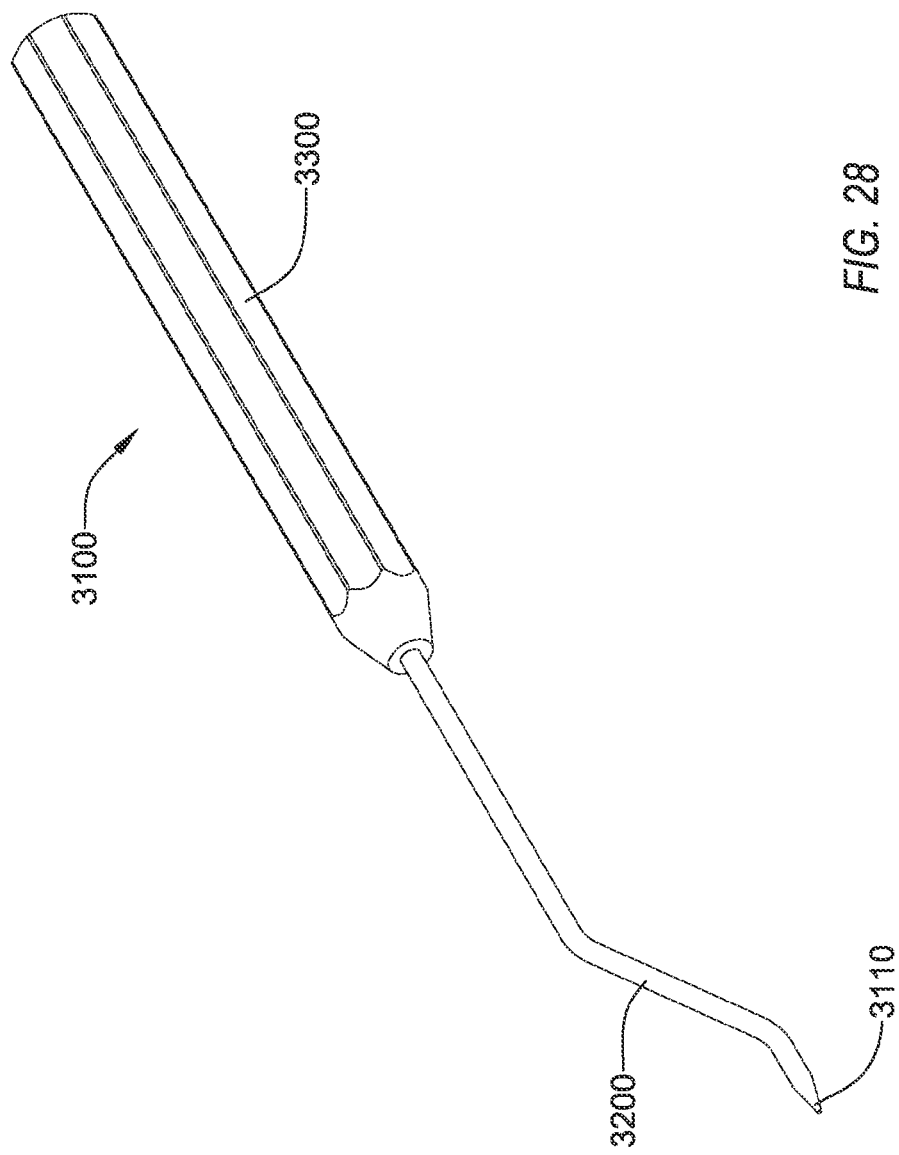
FIGS. 28-29 schematically illustrate embodiments of a passageway tool adapted to form a tissue tunnel.
Figure 29:
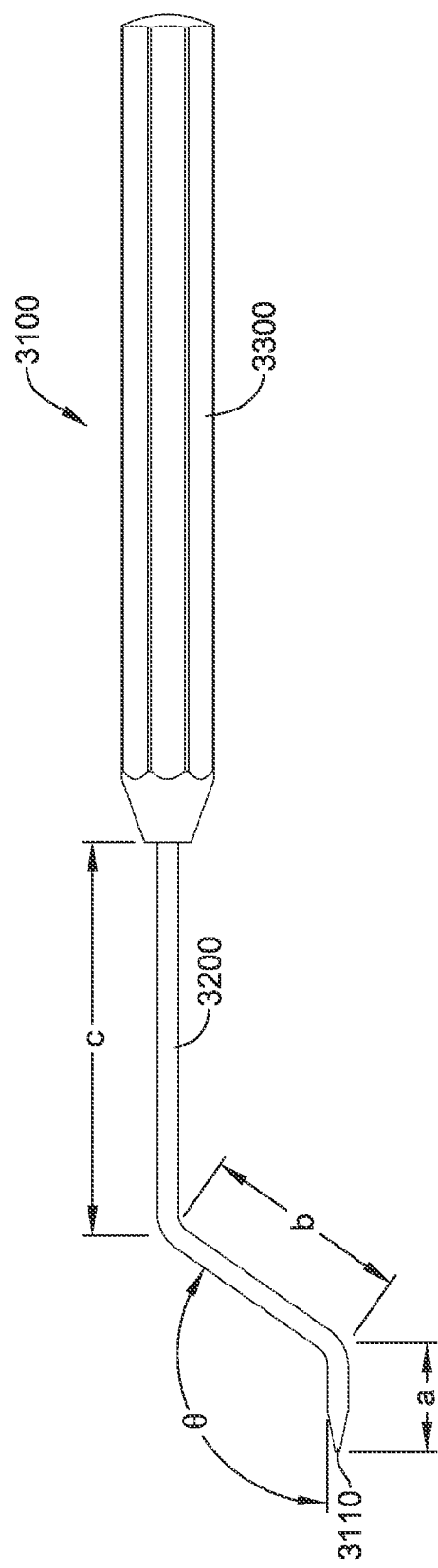

In some methods, a tissue tunnel (or canal) is formed between adjacent target vertebral sites to facilitate positioning a fixation element (e.g., a fixation rod) between the target sites. FIG. 26 schematically illustrates a tissue tunnel 3000 formed between adjacent heads of fasteners 800. In certain procedures, the tissue tunnel 3000 is formed with a pointed passageway tool 3100 as schematically illustrated in FIG. 27 (in which the multipurpose tools are not drawn for purposes of clarity). In certain embodiments, the passageway tool 3100 has a pointed tip 3110 that can be used percutaneously to pierce the tissue of the patient so as to create the tissue tunnel 3000. FIGS. 28 and 29 schematically illustrate an embodiment of a passageway tool 3100 comprising a needle attached to a handle. The needle has a distal end with a pointed tip 3110 for puncturing tissue.

In certain procedures, the tip of the passageway tool is advanced to the target location by inserting the tip of the tool into the central bore within the multipurpose tool. The passageway tool is inserted into the bore through the slots between the arms of the multipurpose tool so as to permit a wider vertical range of motion of the passageway tool. When the tip of the passageway tool reaches the target location (e.g., adjacent the head of a fastener), the passageway tool is pushed toward an adjacent target location. The pointed end of the passageway tool thereby creates the tissue tunnel as it slides or otherwise moves between adjacent target locations. In some procedures, the passageway tool is inserted into one of the percutaneous paths and used to make a complete tissue tunnel from one target site to an adjacent target site. However, in other procedures, the passageway tool is used to make a first tunnel extending partially toward the adjacent site. The passageway tool is then inserted into the adjacent percutaneous path and manipulated to make a second tunnel that joins with the first tunnel thereby forming the complete tissue tunnel. In yet other procedures, two (or more) passageway tools are used to create the tissue tunnel.

An advantage of using the passageway tool to create the tissue tunnel is that no additional punctures, incisions, or percutaneous paths in the patient are required. Because the passageway tool is advanced and manipulated through a previously opened percutaneous path, additional trauma to the patient is reduced. In order to form a more horizontal tissue tunnel (e.g., substantially parallel to an axis between the adjacent vertebral sites), a proximal end of the passageway tool (e.g., the handle which is outside the patient) can be lowered toward the patient's skin thereby causing the distal end of the tool to assume a more horizontal orientation. As the passageway tool is manipulated to create the tissue tunnel, surrounding tissue at the sides of the percutaneous path may be stretched or retracted. However, a suitably curved or shaped needle on the passageway tool can permit easier entry to the target location and can reduce trauma to surrounding tissue as the tool is manipulated to form the tissue tunnel.

FIGS. 28 and 29 are perspective views that schematically illustrate an embodiment of a passageway tool 3100 comprising a needle 3200 attached to a handle 3300. The needle 3200 has a distal end with a sufficiently sharp tip 3110 for puncturing tissue. In some embodiments, the needle is shaped so that a sufficiently horizontal tissue tunnel can be formed. For example, the needle may have a curved "C" or "S" shape in some embodiments. In the embodiment shown in FIGS. 28 and 29, the needle comprises three linear segments: a tip segment, a middle segment, and a handle segment. An angle θ is defined between the tip segment and the middle segment. The lengths of the segments and the angle θ can be selected to permit the passageway tool to rotated, oriented, and otherwise manipulated within the percutaneous path to provide a sufficiently horizontal tissue tunnel while minimizing trauma to the surrounding tissue. FIG. 29 shows example dimensions (in inches) of one embodiment of the passageway tool that is configured for insertion into a percutaneous opening with an inside diameter of about 0.6 inches. In this embodiment the tip segment (a) is 1.0 inches, the middle segment (b) is 2.1 inches, the handle segment (c) is about 3.5 inches, and the angle θ is about 125 degrees. Other embodiments of the passageway tool can have different dimensions and configurations, and the above dimensions and angles are intended to be representative and not limiting.

The following list describes various acts that may be performed in one embodiment of a percutaneous fixation procedure utilizing the multipurpose tool and the passageway tool.

1. Under fluoroscopy, locate a target site (e.g., a pedicle) of the vertebral body with a Jamshidi targeting needle (or a bone biopsy needle).
2. After locating the target site, use fluoroscopy to determine if the target site is suitable for tapping. If the site is suitable, tamp the Jamshidi targeting needle into the site.
3. Remove the stylet from the Jamshidi targeting needle, and thread a guidewire through the Jamshidi targeting needle. Tamp the guidewire into the vertebral body under fluoroscopy.
4. Repeat steps 1, 2, and 3 as needed to prepare additional target sites for a guidewire.
5. Make an incision on either side of each guidewire as if drawing a line through the guide wires. The incisions may be about 5 mm in length.
6. Dilate over the guide wire until a 15-mm diameter dilator has been used.
7. Remove the smaller dilators leaving in place the 15-mm diameter dilator and the guidewire.
8. Thread the guidewire thru a cannulated tap and tap the target site (e.g., the pedicle) using fluoroscopy for guidance.
9. After tapping is complete, the dilator and the cannulated tap are removed, while the guidewire is left in place.
10. Attach a fastener (e.g., a pedicle screw) to a distal end of a multipurpose tool. Thread the guidewire thru the multipurpose tool/fastener assembly using a cannulated 3.5-mm hex wrench. A retaining clip may be used to hold the fastener in place and to prevent the arms of the multipurpose tool from spreading apart during insertion.
11. Under fluoroscopy, advance the multipurpose tool/fastener assembly to the target site. An anti-torque handle can be disposed on the proximal end of the multipurpose tool to assist in advancing the tool. Using a screwdriver or a hex wrench, screw the fastener into the bone at the target site. Remove the guidewire after the fastener is secured to the target site. Rotate the multipurpose tool so that one of the slots between the arms of the tool is sufficiently aligned with the adjacent guidewire or multipurpose tool. The anti-torque handle can be used to rotate the multipurpose tool.
12. Repeat steps 6 through 11 as needed.
13. Form a tissue channel between two adjacent vertebral sites using a pointed passageway tool. Insert the passageway tool into the multipurpose tool disposed at either site until the point of the passageway tool reaches the head of the fastener. The passageway tool is then advanced toward the other vertebral site so that a "tunnel" is created between the two heads of the fasteners. The passageway tool may have a curved or shaped needle portion that can be rotated and oriented so as to form a tissue tunnel substantially parallel to the cephcaudal direction. Using fluoroscopy, verify that a suitable "tunnel" has been formed.

14. Retract the retaining clip from each of the multipurpose tool/fastener assemblies so that the distal end of the retaining clip is above the "tunnel". Verify with fluoroscopy.
15. With an axial fixation rod holder, grasp one end of the fixation rod and place the other end through the multipurpose tool. Advance the rod until each end of the rod is over a respective head of a fastener. Verify with fluoroscopy.
16. When the rod placement is verified, push down each of the retaining clips to secure the ends of the fixation rod onto the heads of the fasteners.
17. With the fixation rod in position, advance cap screws through the bore in the multipurpose tool using a 4.0-mm hex wrench. One cap screw may be loosely tightened to permit an end of the rod to move. The other cap screw should be tightened to specification with the 4.0 mm hex wrench to secure the fixation rod.
18. If compression/distraction of the vertebral bodies is desired, the compression/distraction link assembly is disposed onto the proximal ends of the two multipurpose tools.
19. Compress or distract as needed for the fixation procedure using the compression/distraction link assembly.
20. When the vertebral bodies are in the desired positions, torque down the loosely secured cap screw onto the fixation rod using the 4.0-mm hex wrench.
21. After the fixation rod is secured, remove the retaining clips from the multipurpose tools and then remove the multipurpose tools from the percutaneous entry path.

In other embodiments of this procedure, additional and/or different acts may be performed, and some or all of the acts may be performed in a different order. Variations of the above embodiment may be used for multi-level spinal procedures. Further, variations of the above procedure can be adapted for use where the target site is a facet joint, a transverse or spinous process, or other suitable vertebral location. Many variations are possible.

C. Additional Methods and Devices for Providing Access to a Surgical Site

Figure 30:
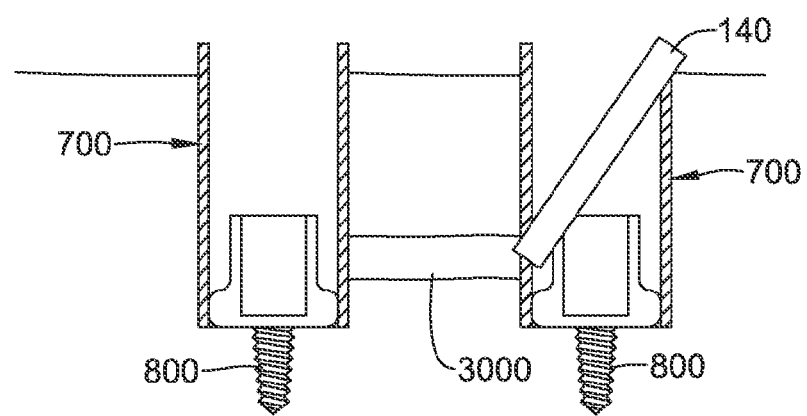
FIGS. 30-32 schematically illustrate an example insertion of a fixation rod into a tissue tunnel.
Figure 31:
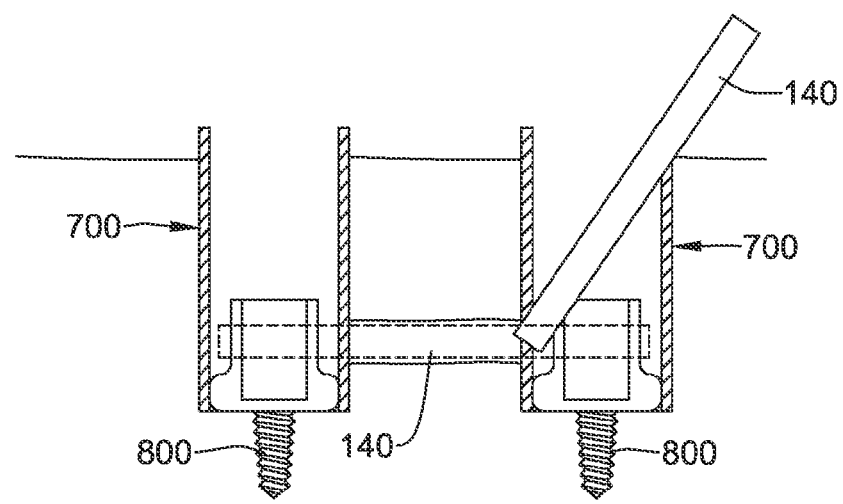

As described above, in various procedures a passageway tool is used to create a tissue tunnel or canal between the adjacent target sites, a fixation element (e.g., a fixation rod) may be advanced through the central bore of the multipurpose tool and into the tissue tunnel formed by the passageway tool. It is advantageous if the fixation element is inserted into the multipurpose tool through the slots defined between the arms of the tool so as to provide a wider vertical range through which to manipulate the element. FIG. 30 schematically illustrates the tunnel 3000 formed by the passageway tool and the fixation rod 140 being advanced into position. FIG. 31 schematically illustrates an initial and a final position of the fixation rod 140. In manipulating the rod into position, portions of the tissue surrounding the percutaneous path may be stretched and/or retracted; however, additional incisions, punctures, or percutaneous paths are generally not required in order to position the fixation element within the tunnel.

Figure 32:
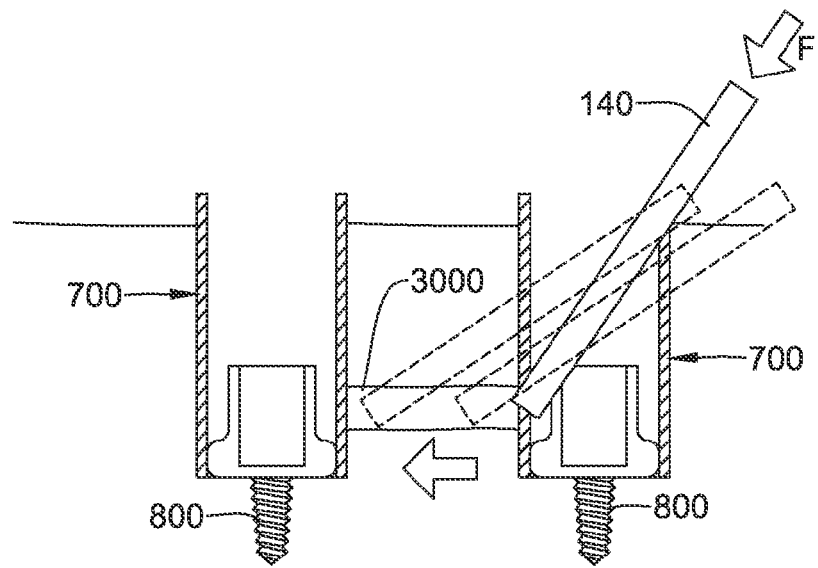

In some procedures, the fixation rod is pushed through the tissue tunnel, and in other methods the rod is pulled through the tissue tunnel. In yet other embodiments, a combination of pushing and pulling is used. FIG. 32 schematically illustrates a "pushing" method that uses a force F to push the fixation rod 140 into position. In FIG. 32, the rod 140 is pushed from right to left as indicated by the arrow ("rod direction"). In some pushing techniques, no special tools are used, and the fixation rod can be pushed by any suitable device including, for example, a hex tool or a screwdriver. The rod is manipulated into the tissue tunnel 3000 as it is being pushed, because of the absence of resistance from the surrounding tissue. The movement of the rod in the tunnel may be lubricated by blood present in the tunnel.

Figure 33:
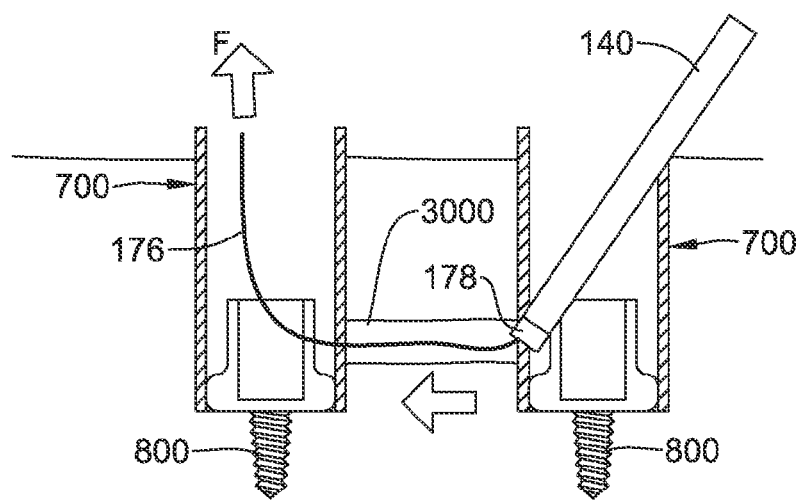
FIGS. 33-34 schematically illustrate various example methods, assemblies, and aspects for inserting a fixation rod into a tissue tunnel.

FIG. 33 schematically illustrates a "pulling" technique that can be used alone or in combination with the pushing technique. In this embodiment of the pulling technique, a threading feature and/or flexible puller member, such as, for example, a suture, a cable, or a wire 176 is connected to an end of the fixation rod 140, and a force F is applied to an end of the threading feature so as to pull the rod through the passageway 3000 created by the passageway tool. In some techniques, the suture is connected to the fixation rod by an attachment element 178. The attachment element 178 may comprise an eyelet or a finger trap suture or flexible cap or some other suitable device or structure for connecting the suture 176 to the rod 140.

Figure 34:
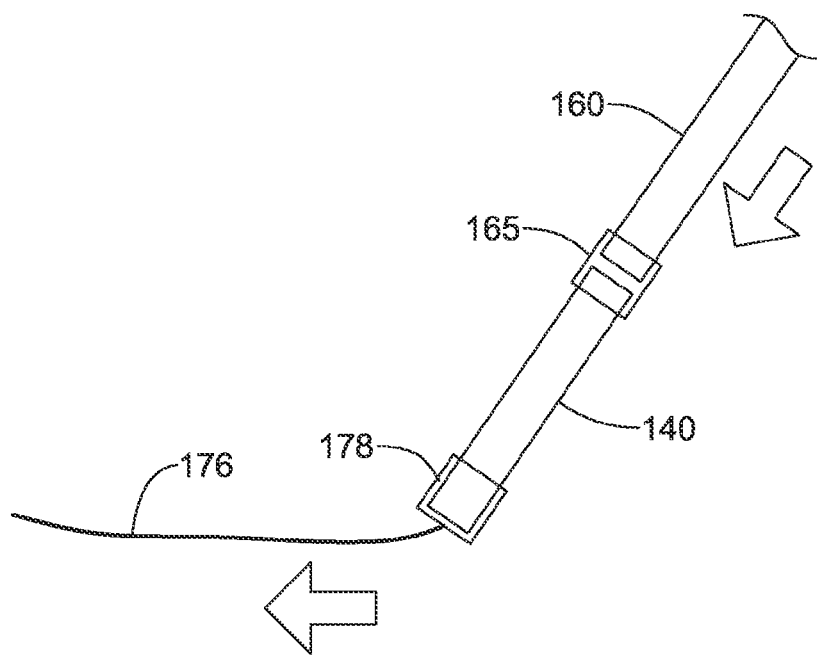
Figure 35:
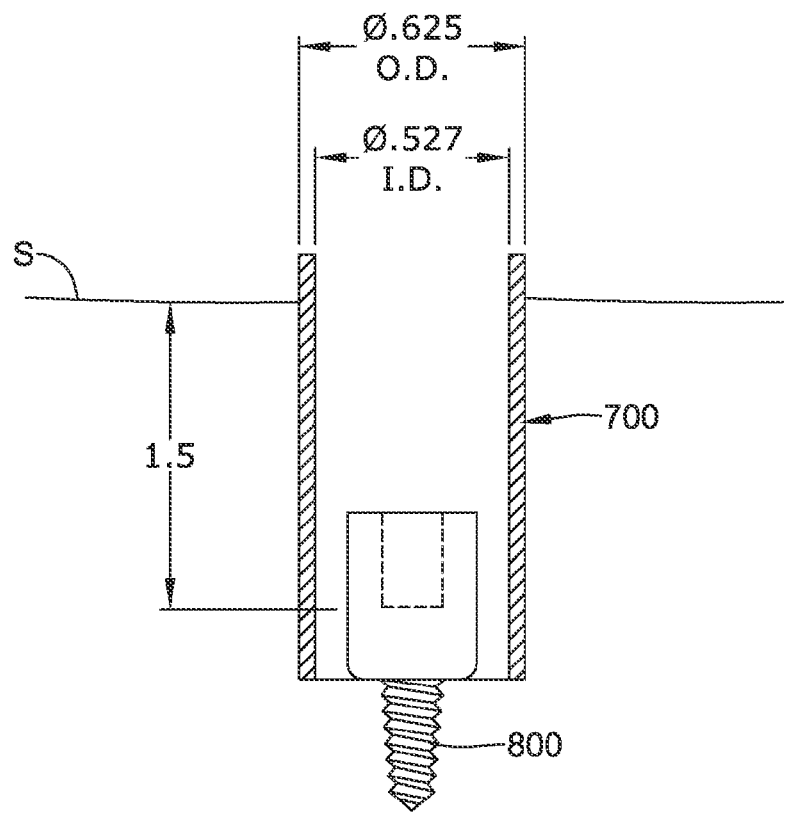
FIG. 35 schematically illustrates dimensions and sizes of one embodiment of a multipurpose tool.

Some techniques utilize a combination of the pulling and the pushing methods. As shown in FIG. 34, a coupling element 165 may be used to mechanically connect a pushing device 160 (such as a hex tool, a screwdriver, or other instrument) to the fixation rod 140 while it is being advanced into position. The coupling element 165 may aid in transmitting the pushing force to the fixation rod. The coupling element 165 may also stabilize the pushing motion by inhibiting lateral deflection of the rod away from the direction of the passageway and canal created by the passageway tool. The fixation rod may also be pulled while it is being pushed. In certain techniques, pulling force and pushing force are alternated. FIG. 35 schematically shows dimensions and sizes for one embodiment of a multipurpose tool 700 that can be used with various methods discussed herein. The multipurpose tool 700 shown in FIG. 35 has an inner diameter (I.D.) of 0.527 inches, an outer diameter (O.D.) of 0.625 inches, and an inserted depth between the skin S and the distal portion of the rod-receiving opening in the fastener head of 1.5 inches.

Figure 36A:
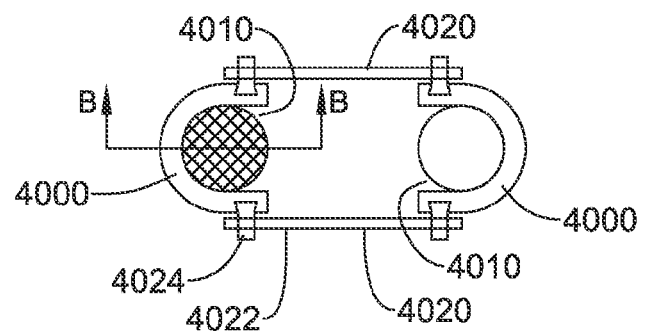
FIGS. 36A, 36B, and 37-39 schematically illustrate embodiments of screw installation tools.
Figure 36B:
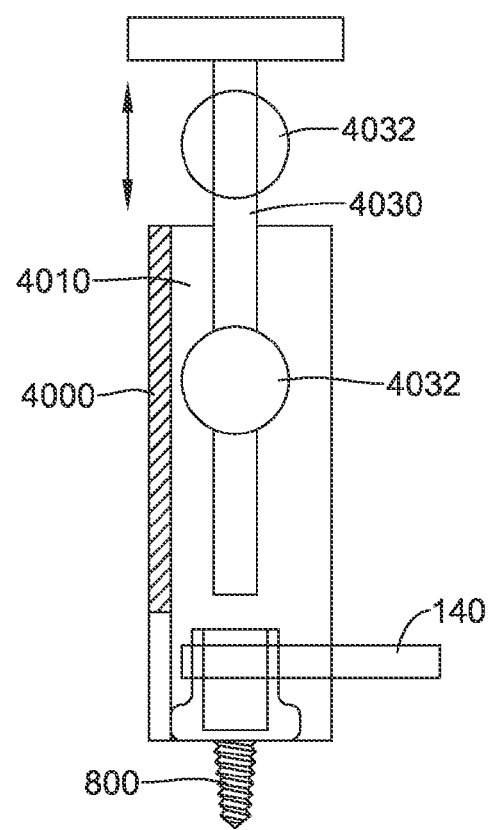
Figure 37:
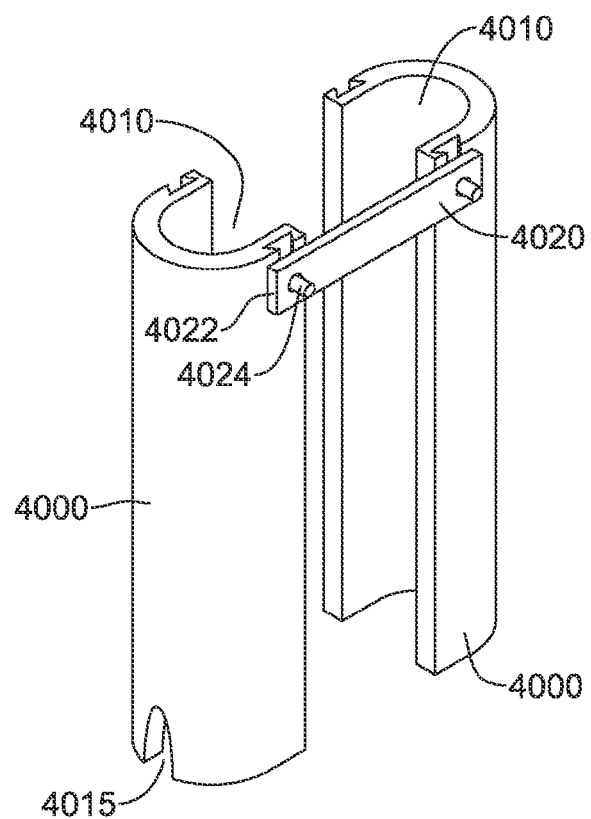

FIGS. 36A-39 schematically illustrate further devices and methods that can be used to provide surgical access to a vertebral site. FIGS. 36A, 36B, and 37 schematically illustrates a pair of elongated, generally "U"-shaped (or hemispherical) pedicle screw installation tools 4000. The "U"-shaped tool has an inner channel 4010 that is sized to provide clearance for a pedicle screw assembly 800 and a fixation rod 140. In some methods, two installation tools are inserted through the skin of the patient and extend from the skin to the vertebral site. A positioning member 4020 can be secured to both installation tools 4000 so as to preserve the position and orientation of the installation tools and to prevent the tools from moving towards or away from each other. In one embodiment, one positioning member is secured to each side of the pair of installation tools, as shown in FIG. 36A, a top view. In other embodiments, a single positioning member is used, as shown in FIG. 37. In certain embodiments, the positioning member comprises a pivot strap 4022 that is attached to the installation tools via screws or rivets 4024. In some embodiments, one or more of the "U"-shaped installation tools have a side window 4015 (e.g. "channels" and/or "cut outs" or "mating openings" and/or "laterally facing openings") disposed at the distal end. The side window 4015 is configured to receive the fixation rod 140.

FIG. 36B is a cross-section taken through line B-B in FIG. 36A, and also schematically shows an embodiment of a hex screwdriver 4030 that can be used to guide the pedicle screws 800 through the channel 4010 between the arms of the "U." Additionally, the hex screwdriver 4030 can be used for angular alignment and adjustment. In some embodiments, the hex screwdriver 4030 comprises a ball feature 4032 disposed on the shaft of the screwdriver 4030. In such embodiments, the screwdriver has a range of transverse angular motion. However, in other embodiments, two ball features 4032 are disposed on the shaft. When both ball features are disposed within the "U"-shaped channel, the transverse angular motion of the screwdriver is substantially limited, and the screwdriver provides linear (e.g., vertical) movement (as well as rotational movement).

Figure 38:
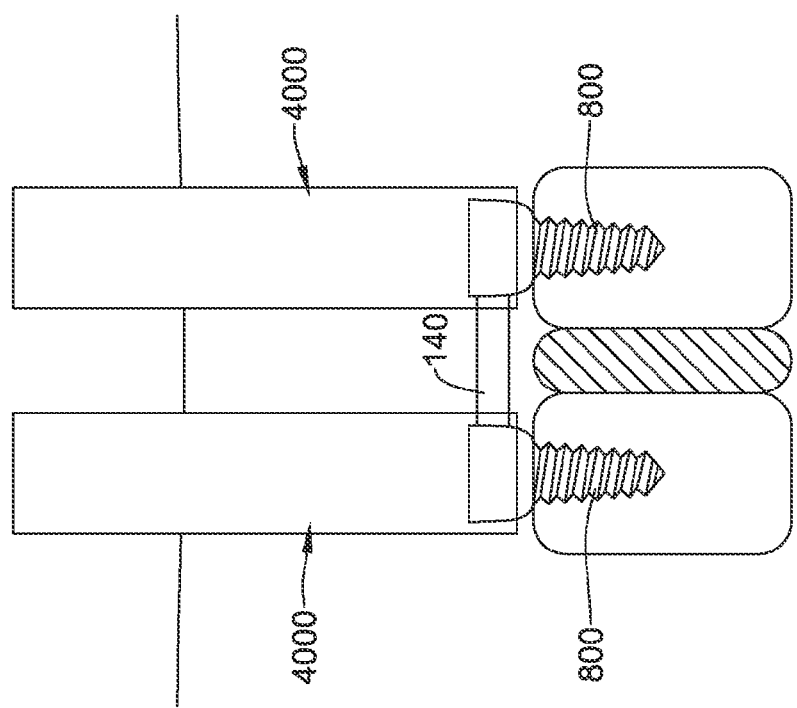
Figure 39:
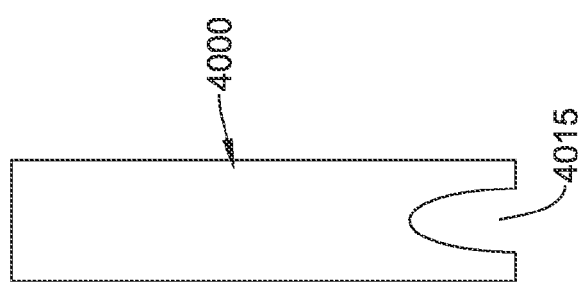

FIG. 38 shows two pedicle screw installation tools 4000 inserted at adjacent vertebral sites. A distal end of each of the tools can include one or more side windows 4015, which can be used to assist positioning of a fixation member. Pedicle screws 800 can be inserted into the pedicle via a targeting needle and a guidewire (as described above).

In one technique, an incision is made between the two installation tools and the fixation element (e.g., a rod) is inserted through the incision and into position onto the pedicle screws. After the fixation element is in position, the element can be secured to the pedicle screws via set screws or cap screws. The set screws or cap screws can be inserted via the installation tools (and the guidewire in some methods). In this technique, there is generally no debridement of muscle tissue, and dead tissue is absorbed by the body.

D. Systems and Methods for Spinal Procedures Using Break-off Screw Heads

FIGS. 40-45 schematically illustrate an example spinal procedure for at least partially percutaneously delivering a fixation element 140 (e.g. a fixation rod) to a target site adjacent the vertebrae of a patient. The procedure may include, for example, a fixation, a fusion, and/or other suitable stabilization procedure, and the procedure can be a one-level or multi-level procedure. The target site may be any suitable site on the vertebra of the patient including, for example, a pedicle, a spinous or transverse process, a facet joint, or a combination of such sites. Although a generally posterior approach is illustrated in FIGS. 40-45 (e.g., a postero-lateral approach), in other procedures other spinal approaches may be used such as, for example, anterior, lateral, or retroperitoneal.

Figure 40:
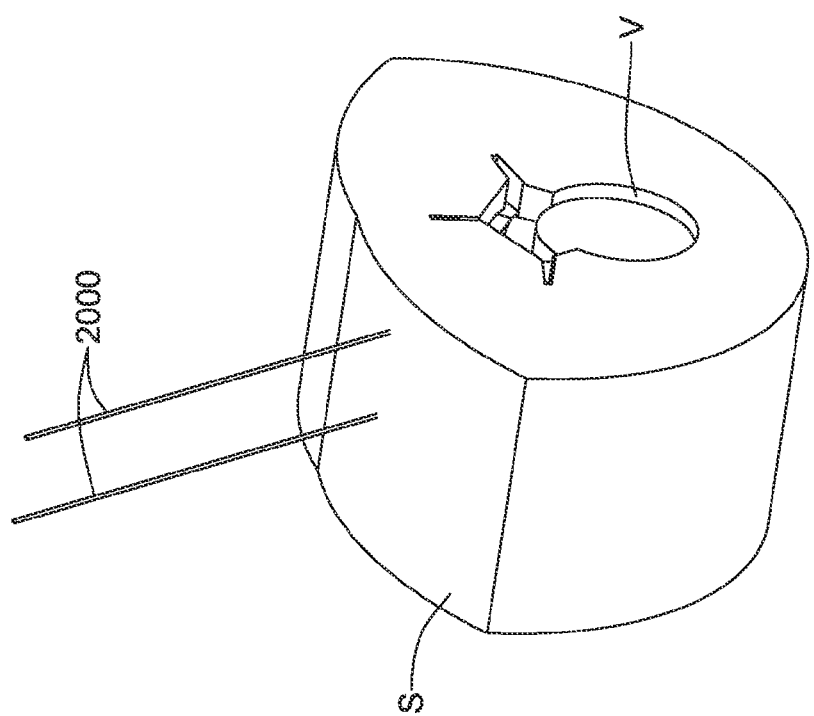
FIGS. 40-41 schematically illustrate embodiments of apparatuses used in an example spinal procedure for at Least partially percutaneously delivering an implant to a vertebral site.

FIG. 40 is a perspective view that, schematically illustrates a stage in the procedure when two guidewires 2000 have been delivered to suitable target sites. For example, a trocar and needle (such as a Jamshidi needle or bone biopsy needle) are percutaneously passed through the skin S and into the targeted pedicle and into the vertebral body V. The trocar and needle form a percutaneous access path that is sometimes referred to herein as a tissue tunnel. In one technique, the trocar is inserted into the needle and the trocar and needle are advanced together through the skin at a skin puncture location and through subcutaneous tissue (e.g., through fat, muscle, and fascia) until a distal end of the trocar and needle are at the vertebral target site. The needle and trocar thus create a tissue tunnel through subcutaneous tissue. In one method, a generally posterolateral approach is employed and the initial advancement of the needle and trocar positions the needle and trocar at the pedicle of the target vertebra. Advancement of the needle and trocar may be aided by fluoroscopy, e.g., using a C-arm or other similar technique.

After a percutaneous entry, or percutaneous entry path, has been created through the skin and subcutaneous tissue, the vertebral target site may be prepared, if desired. In one method, the needle and trocar are advanced further into the target vertebra at the vertebral target site to form a tunnel in the target vertebra. The tunnel may be formed in the pedicle and is sometimes referred to as a pedicle, tunnel. A proximal end of the trocar may remain outside the patient, above the skin puncture location throughout the target site preparation. Preparation of the vertebral target site may include further procedures, such as tapping of the pedicle tunnel.

In one embodiment, the trocar is removed, leaving the needle in the pedicle. A guidewire 2000, or other elongate body, is inserted into the proximal end of the needle. The guidewire may be advanced through the tissue tunnel and through the pedicle tunnel within the needle. In one application, the guidewire is advanced until a distal end of the guidewire is located in the vertebral body of the target vertebra. The guidewire extends proximally from the skin and the proximal end of the needle at the stage of the procedure illustrated in FIG. 40. In some techniques, the guidewire has an outer diameter of about 1.5 mm. The needle is removed leaving the guidewire in place, extending distally into the pedicle tunnel and proximally out of the skin. In similar manner, additional guidewires can be delivered to other target vertebral sites (e.g., FIG. 40 schematically illustrates two guidewires).

In some applications, further dilation of the percutaneous access path or entry facilitates insertion of an access device and/or retractor 101. In certain techniques, a small incision is created at the skin puncture location, which in one technique is about 5-15 mm long. In some variations, an incision that is less than 5 mm can be created. The incision also can extend a distance into the tissue beneath the skin. The incision facilitates the insertion of one or more dilators (or obturators) over the guidewire to increase the size of the percutaneous access path or entry. In some techniques, a cannulated dilator with an outer diameter of about 5 mm is used. The dilator may be advanced at least a substantial portion of the distance from the skin puncture location to the surface of the vertebra to reduce the resistance of the tissue beneath the skin to the insertion of an implant. The dilators are removed prior to insertion of a retractor in one technique.

Figure 41:
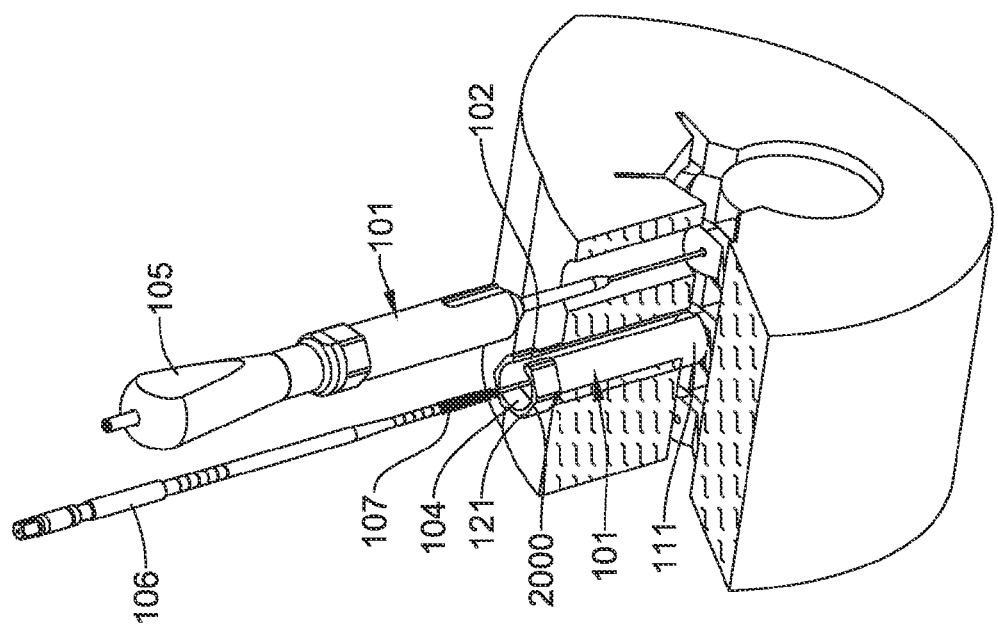

In certain techniques, an access device and/or retractor 101 is placed within the percutaneous entry path to provide a space for the insertion of an implant at a later stage of the procedure, as shown in FIG. 41. Additionally, the retractor can protect the tissue from damage caused by instruments (e.g., sharp cutting flutes of a cannulated tap). The retractor 101, in certain embodiments, is an elongate body having a proximal end 121 and a distal end 111 and having a bore or cannulation 104 extending therebetween. The elongate body has a length such that the proximal end 121 extends out from the skin when the distal end 111 is adjacent the vertebral site. The bore 104 has an inside diameter that is slightly larger than the width of implants to be delivered therethrough. In some embodiments, the elongate body may include one or more slots 102 or openings to provide an increased amount of access to the vertebral sites. For example, in some embodiments the elongate body has a generally "C"-shaped cross section, wherein the opening in the "C" comprises a slot 102 that extends between the proximal 121 and distal 111 ends. Certain such embodiments also have a shorter slot or opening at the distal end to provide further access to implants at the target site. The proximal end 121 of the retractor may be fashioned into a hex-shape (or other suitable shape) to permit instruments, handles, etc. to grasp and firmly hold the retractor. The outside surface of the retractor may be threaded or ribbed to prevent the retractor from migrating during the procedure. The retractor may be configured to permit other instruments (e.g., a visualization instrument) to be attached thereto. The retractor is fabricated from a substantially rigid material such as a metal (e.g., stainless steel or titanium). In one embodiment, the retractor is made from plastic, which advantageously can electrically insulate body tissue from implants and instruments within the bore of the retractor. The retractor can be made of material (such as plastic or thin metal) which is radiolucent, allowing for fluoroscopic visualization through the retractor.

In some techniques, the retractor is inserted into the dilated percutaneous access path and advanced through the tissue tunnel until the distal end is adjacent the target site. The retractor 101 may be advanced over the guidewire 2000 using a cannulated obturator 105 (or cannulated dilator) as schematically illustrated, for example, in FIG. 41. Additional retractors can be positioned so as to provide access to additional target sites. In techniques using "C"-shaped retractors, the openings in adjacent retractors may be aligned so as to face each other.

Optionally, it may be advantageous to prepare the pedicle tunnel by forming threads within the tunnel. One method of forming threads in the pedicle tunnel involves tapping the pedicle tunnel with a cannulated tap 106. A cannulated tap 106 is a low profile instrument that has an elongate body and an outside surface. The elongate body extends between a proximal end and a distal end. A bore, or cannulation, is formed through the elongate body between the proximal and distal ends. The elongate body has formed thereon a structure 107 configured to form internal threads within the pedicle tunnel, e.g., on the outer surface. The cannulated tap 106 may be advanced over, e.g., slid over, the guidewire until the distal end is at the vertebral target site. FIG. 41 is a cutaway perspective view that schematically illustrates the cannulated tap 106 being advanced over the guidewire 2000 and through the bore 104 in a retractor 101. Thereafter the cannulated tap may be rotated about the guidewire and advanced, turning the cannulated tap into the pedicle tunnel. As the cannulated tap advances the threads are formed in the pedicle tunnel. Tapping creates threads in the pedicle tunnel that will mate with corresponding threads on an implant to be inserted later.

An implant such as, for example, a fastener (e.g., a pedicle screw) can be inserted into and advanced to the target location through the bore in the retractor. In one technique, a fastener such as, for example, a cannulated pedicle screw, is inserted over a proximal end of the guidewire. In some procedures, a cannulated screwdriver or other instrument can be used to move the fastener through the access device to the vertebral site, where it can be attached to the pedicle and vertebral body (e.g., by screwing with the cannulated screwdriver). In one method, after insertion and attachment of the fastener, the screwdriver and the guidewire can be removed, leaving the fastener and retractor in place.

Figures 42A, 42B:
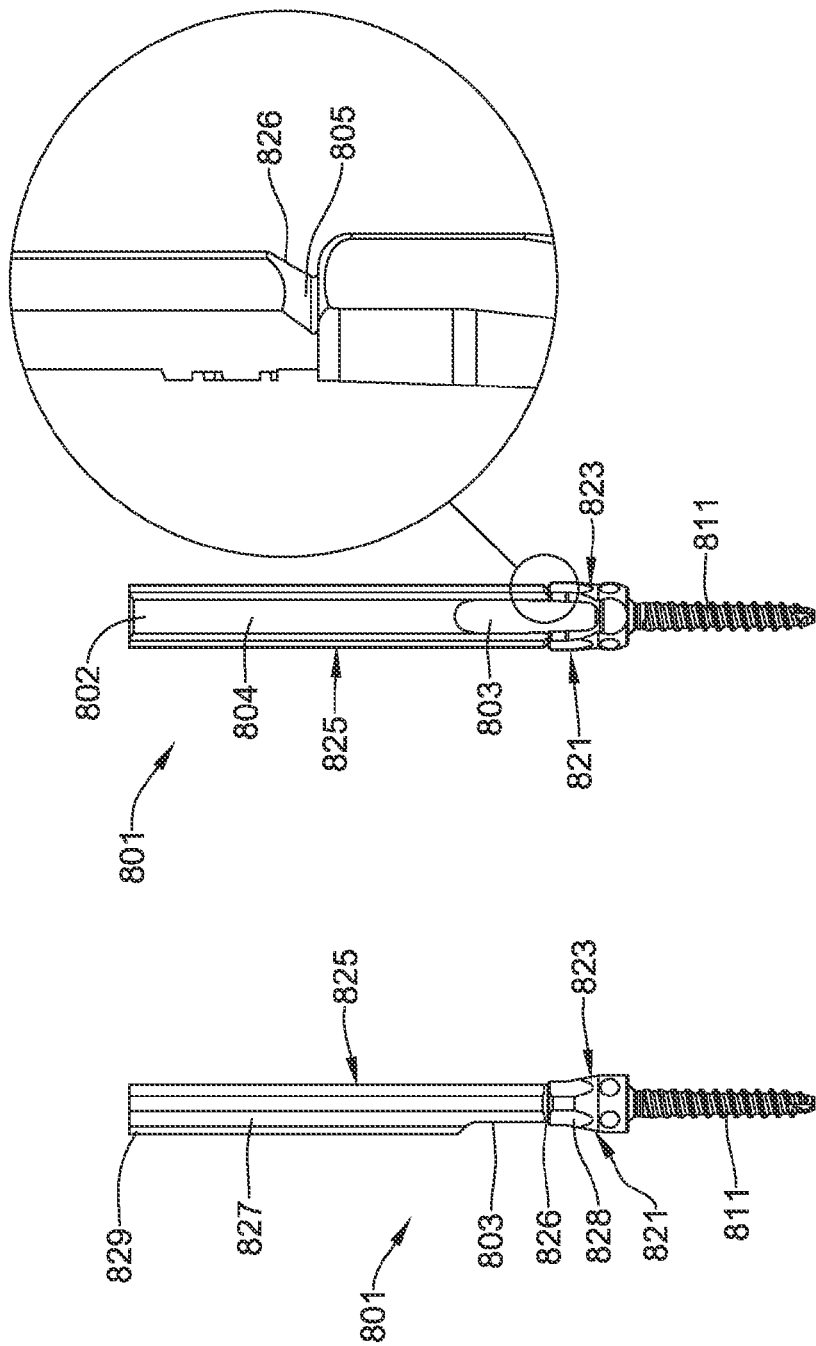
FIGS. 42A-42B schematically illustrate an embodiment of a screw with a breakoff head.

In certain techniques, the fastener is a screw with an extended breakoff head. FIGS. 42A and 42B include side views (from two roughly perpendicular directions) schematically showing an embodiment of a screw 801 with an extended breakoff head 821. For example, the fastener may comprise an elongated screw portion 811 extending along a longitudinal axis and having threads configured to mate with the threads formed in the pedicle tunnel by the cannulated tap. The screw portion 811 may be cannulated to permit passage over a guidewire. The screw portion 811 of the fastener is attached to a breakoff head 821 that, in some embodiments, comprises a housing 823 and an elongated body 825. The housing 823 is configured to retain a fixation element 140. For example, the housing 823 may include a portion that is substantially "U"-shaped in a longitudinal cross-section relative to the longitudinal axis, generally similarly to the "U"-shaped head of the fastener described with reference to FIG. 15. A portion of a fixation element 140 (e.g., an end of a fixation rod) may be placed within the housing 823 and secured by, for example, a cap screw 900 as further described herein. The housing 823 may be configured with facets 828 (such as a hex shape) that can couple to other tools such as a screw head cutter (described further below).

The head 821 of the fastener shown in FIGS. 42A and 42B further comprises the breakoff head, which is an elongated body 825 attached to the housing 823 at a neck 826 and extending to a proximal end 829. The breakoff head 821 has a length between the neck 826 and the proximal end 829 that is sufficient for the proximal end 829 to extend above the skin of the patient when the fastener is secured to the target site. Advantageously, such a fastener can be advanced to the target site by manually holding the proximal end and guiding the screw portion through the bore of the retractor and into, e.g., the pedicle tunnel. Because of the length of the breakoff head, the proximal end of the fastener remains outside the patient. Accordingly, such a fastener is readily accessible to the physician, unlike certain smaller listeners that can be difficult to access when placed at the target site at the distal end of the tissue tunnel. In one embodiment, the length of the breakoff head is sufficient for the proximal end to extend above the retractor so that the proximal end can be coupled to other instruments.

The breakoff head 821 has an outer surface 827 that may be shaped (e.g., with a hex shape) to permit such coupling to instruments such as, e.g., a countertorque handle or removal device. The breakoff head 821 has a bore or cannulation 802 extending between the neck 826 and the proximal end 829 to permit passage of the fastener 801 over a guidewire. In one embodiment, the outer surface 827 of the breakoff head 821 comprises one or more slots 804 or openings to assist or guide passage of a fixation element (e.g., a fixation rod) to the target site. In the embodiment shown in FIGS. 42A and 42B, a first slot 804 extends the entire length of the outer surface on one side of the breakoff head. Thus, the breakoff head has a proximal portion that is substantially "C"-shaped in a transverse cross section relative to the longitudinal axis. A second slot 803 on the opposing side may extend from the neck part way to the proximal end. The first and second slots 803, 804 align with the opening defined with the arms of the "U"-shaped housing 823 to permit portions of the fixation element to be positioned within the housing 823.

In some embodiments, the head 821 has an elongated body 825 extending along a longitudinal axis and has a distal portion 823 that is substantially "U"-shaped in a longitudinal cross section relative to the longitudinal axis. The elongated body 825 has a proximal portion that is substantially "C"-shaped in a transverse cross section relative to the longitudinal axis. A first slot 804 is defined in the substantially "C"-shaped proximal portion and a second slot 803 is defined in the substantially "U"-shaped distal portion, and the first slot is aligned with the second slot. The housing 823 includes a portion that is substantially "U"-shaped in a longitudinal cross-section relative to the longitudinal axis, and the substantially "U"-shaped distal portion of the elongate body 825 is aligned with the substantially "U"-shaped portion of the housing.

The fastener may be fabricated from a substantially rigid material such as a metal (e.g., stainless steel or titanium). The breakoff head and the housing generally may be integrally machined from the same material. In some embodiments, the neck is configured so that the breakoff head can be detached from the housing and then removed from the patient. For example, the neck 826 may comprise a region of material having a reduced cross sectional area compared to other regions of the breakoff head. Accordingly, when a differential torque or shearing force is applied between the housing and the breakoff head, the neck will mechanically fail (e.g., break, snap, or fracture) when the applied torque or shearing force reaches a sufficiently large value (e.g., a yield stress of the material). In some embodiments, the neck 826 comprises one or more grooves 805 cut into the outer surface (and/or an inner surface) of the breakoff head to provide the reduced cross section suitable for the breakoff feature of the neck (see detail B in FIG. 42B). However, in other embodiments, the breakoff feature is achieved by, for example, perforating the neck or by any other suitable mechanism that reduces the yield stress at the neck.

Figure 43:
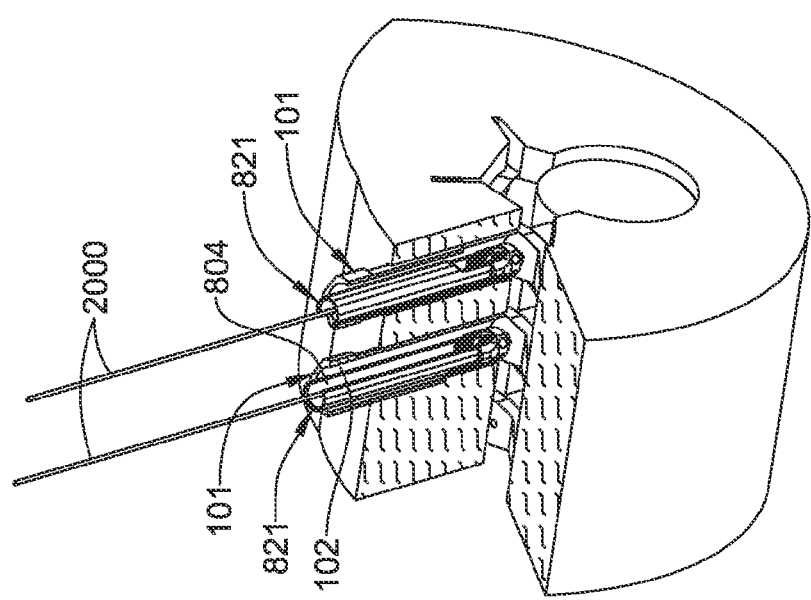

FIG. 43 is a perspective cutout view that schematically illustrates a stage in the example procedures when two fasteners with extended breakoff heads 821 are positioned over guidewires 2000 within adjacent retractors 101. Each fastener is aligned so that the first slot 804 in the breakoff head 821 aligns with the slot 102 in the "C"-shaped retractor 101. Additionally, the adjacent retractors are aligned so that the slots are generally aligned with each other. Accordingly, the aligned slots in adjacent retractors and breakoff heads define guides for opposing ends of a fixation element to be advanced to the target site as further described below. In some techniques, the guidewires are removed from the patient after insertion of the fasteners.

In some embodiments, two separate incisions are made and two retractors are inserted and a fixation element is inserted through one retractor as discussed above. In another embodiment, an incision is made between the two adjacent retractors, along an imaginary line joining the aligned slots of the retractors. The incision extends below the skin and through tissue to the adjacent target vertebral sites. The incision creates a percutaneous path for the insertion of a suitable fixation element. The percutaneous path is a portion of a plane defined between adjacent retractors and may be referred to herein as a tissue plane.

Figure 44B:
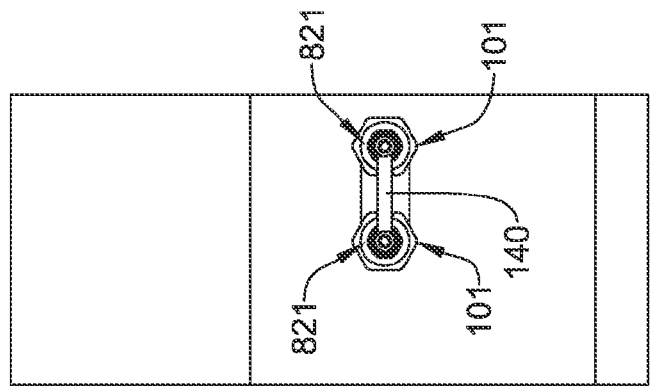
Figure 44A:
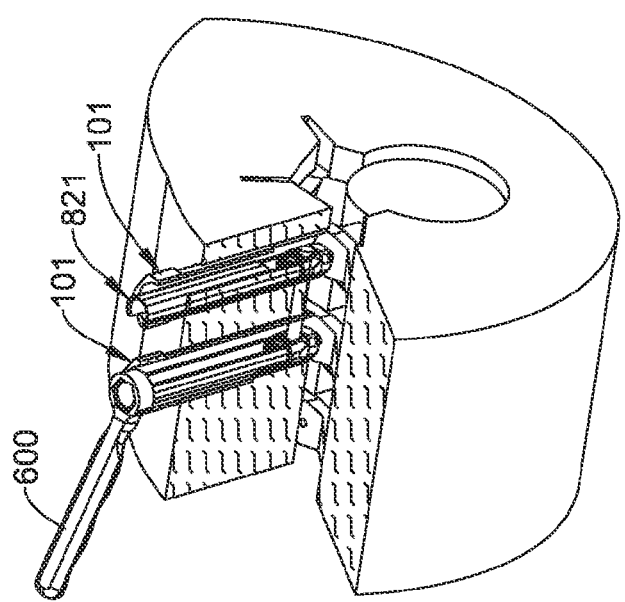

In some techniques, the fixation element is advanced through the tissue plane with the aid of a grasping instrument. As described above with reference to FIG. 43, the generally aligned slots in the "C"-shaped retractor and breakoff head define a guide for advancing an end of the fastener toward the housing of the fastener at the target site. In one technique, opposing ends of the fixation element are placed within the guides formed by opposing retractor/breakoff heads, and the fixation element is advanced through the tissue plane to the vertebral site. The guides provide several benefits. For example, the guides assist in keeping the fixation element in the tissue plane as it is advanced to the target site and facilitate insertion of the ends of the fixation element into the housings of the fasteners. Also, the use of guides makes it easier to advance the fixation element through the tissue plane, since the portions of the fixation element disposed in the guides do not experience resistance from the tissue. FIGS. 44A and 44B include a top view (FIG. 44B) that schematically illustrates the generally aligned "C"-shaped retractors 101 and breakoff heads 821 and the fixation element 140 (here, a rod) with opposite ends disposed in the guides.

However, in other techniques, only one end of the fixation element is placed within a guide, and the fixation element is advanced to the target site, for example, by advancing the fixation element at an angle. When the fixation element has reached the target sites, the ends of the element are positioned within the housings of the fasteners and then secured, e.g., by cap screws. In some techniques, the cap screw is advanced through the bore of the extended breakoff head to reach the housing of the fastener. The housing has an inner surface which is threaded to receive the cap screw. In one embodiment, the threads in the housing extend into the inner surface of the breakoff head near the neck which beneficially permits the cap screw to engage the threads at a more accessible, proximal position.

An instrument such as a screwdriver can be used to tighten the cap screws. As schematically illustrated in FIG. 44A, in some techniques, a countertorque handle 600 is attached to the proximal end of the breakoff head 821 (which extends above the proximal end of the retractor) and is used to provide countertorque while the cap screws are being tightened. In other techniques, an elongated tube having a notch at a distal end configured to mate with the fixation element is advanced over the breakoff head so that countertorque can be applied to the fixation element. In some techniques, a grasping instrument is used to apply countertorque to the fixation element. If desired, compression and/or distraction of the vertebrae may be performed prior to the final tightening of the cap screws.

After the fixation element has been secured, the breakoff heads of the fasteners are detached from the housing and removed from the patient. In some techniques a screw head cutter and/or removal tool 602 is attached to the breakoff head, and a differential torque or shearing force is applied so as to shear (or snap or otherwise break) the breakoff head from the housing. FIG. 45 is a perspective view that schematically illustrates a stage of the example procedure when the screw head cutter 602 has been attached to the breakoff head disposed in the retractor 101 on the right side of the drawing in preparation for detachment from the housing. FIG. 45 also illustrates the retractor 101 on the left side of the drawing in which the breakoff head has been removed.

Figure 46:
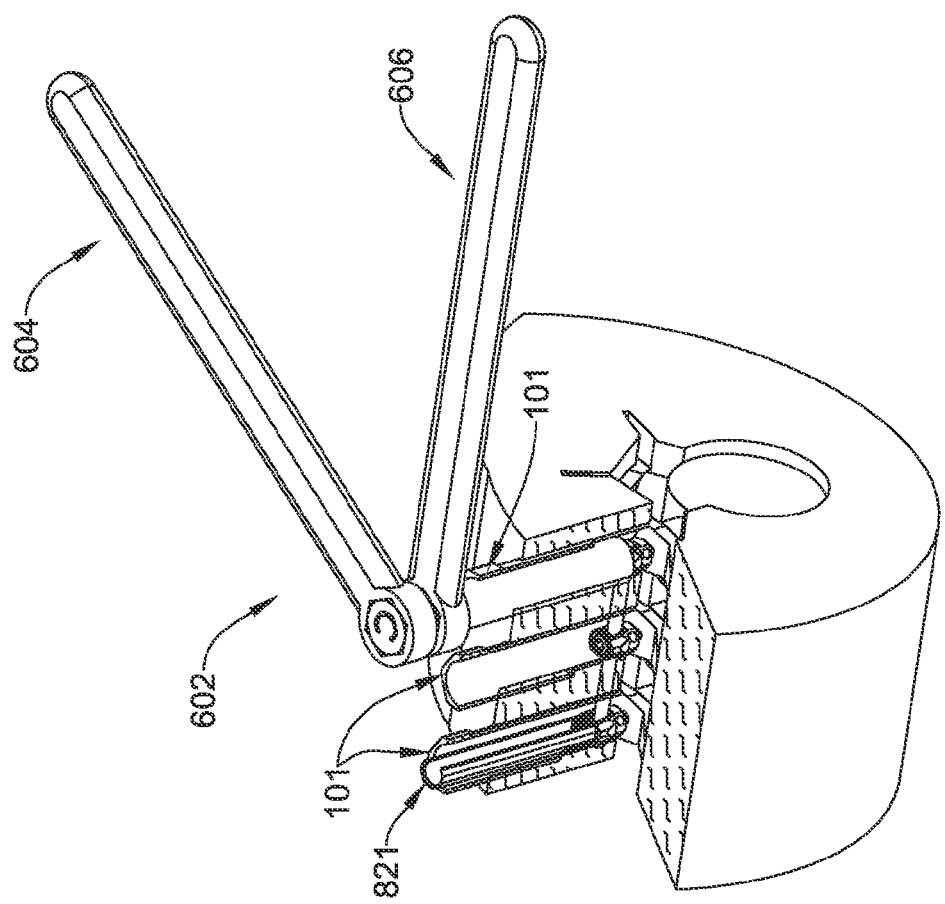

FIG. 46 is a perspective view schematically illustrating a stage in an example two-level spinal procedure, for example, a two-level fixation or stabilization procedure. At the stage shown, the screw head cutter 602 is attached to the breakoff head 821 in the rightmost retractor 101 in preparation for detachment and removal from the patient. The breakoff head has been removed from the middle retractor, while the breakoff head 821 is still within the leftmost retractor 101 at this stage. Thus it is recognized that the devices and methods presented herein are suitable for use in one-level as well as two-level or multi-level spinal procedures.

Figure 47:
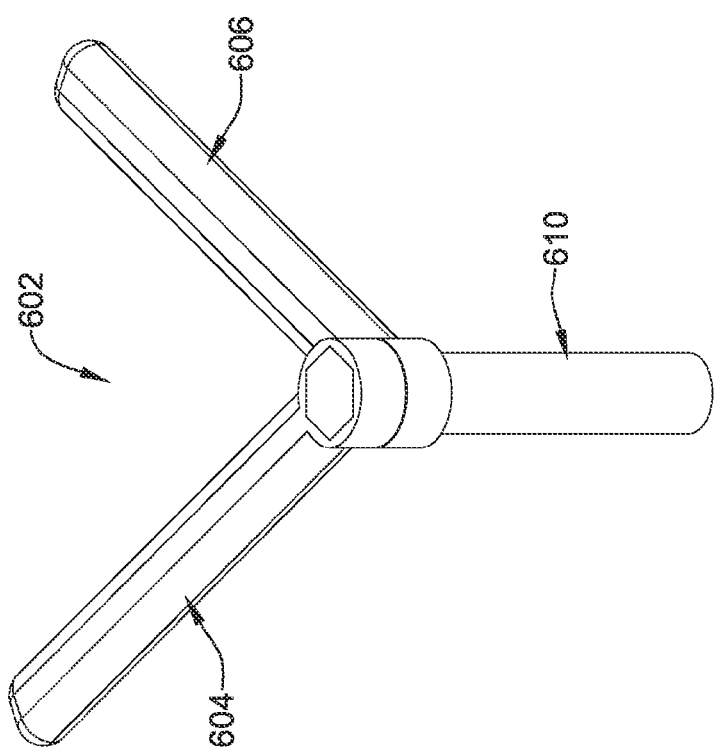
FIGS. 47-48 schematically illustrate various views of an embodiment of a screw head removal tool that can be used to remove the breakoff heads, for example, from the example screws shown in FIGS. 42A-42B.
Figure 48:
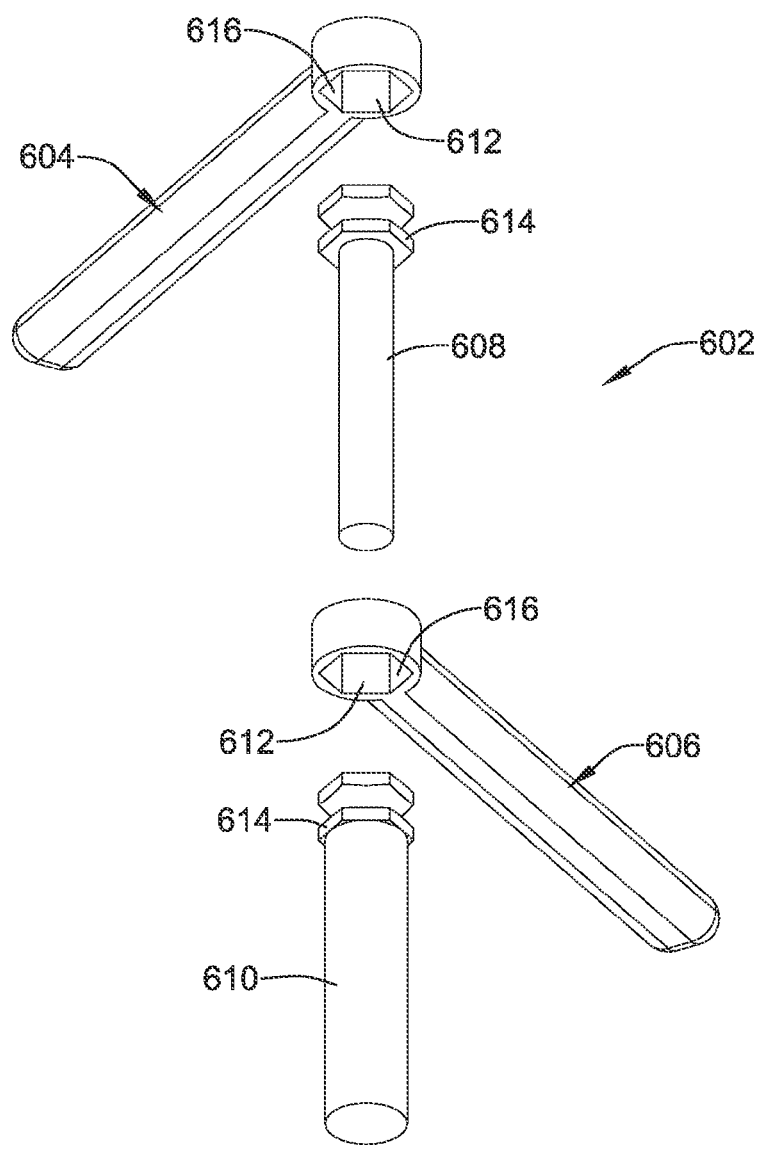

FIGS. 47-48 schematically illustrate an embodiment of a screw head cutter 602 which is generally similar to the screw head cutter illustrated in FIGS. 45-46. The screw head cutter 602 is adapted to detach a breakoff head 821 from a housing in a fastener by, for example, exerting a differential torque or shearing force between the breakoff head 821 and the housing 823. FIG. 47 is a perspective view and FIG. 48 is an exploded perspective view.

In the embodiment shown in FIGS. 47-48, the cutter comprises a first 604 and second 606 handle, an inner sleeve 608, and an outer sleeve 610. The first and second handles 604, 606 each comprise a central annular portion 612 that can be attached to a proximal end of the inner sleeve and the outer sleeve, respectively. For example, the ends of the sleeves may comprise a hex shaped portion 614 that is configured to mate with hex-shaped facets 616 on an inner surface of the central annular portion 612 of the handles 604, 606 (see FIG. 48). The inner and outer sleeves are each elongated bodies configured so that the inner sleeve can be disposed within a central cavity in the outer sleeve. For example, the inner and outer sleeves may comprise generally cylindrical tubes with the outer diameter of the inner sleeve being slightly less than the inner diameter of the central cavity in the outer sleeve so that the inner sleeve can slide into the outer sleeve. The exploded views in FIG. 48 illustrate a possible method of assembling the screw head cutter. The second handle 606 is attached to the proximal end of the outer sleeve 610, and the inner sleeve 608 is inserted into the central cavity in the outer sleeve 610. The proximal end of the inner sleeve has an enlarged cross section (compared to the elongated tubular portion), which prevents the inner sleeve from sliding through the outer sleeve and which extends above the proximal end of the outer sleeve. The first handle 604 is then attached to the proximal end of the inner sleeve 608. The inner sleeve can rotate within the outer sleeve, hence, forces applied to one or both handles can be used to turn the inner sleeve relative to the outer sleeve.

The inner sleeve comprises a passageway with a cross-sectional shape that permits the inner sleeve to slide onto the breakoff head, thereby substantially surrounding the breakoff head. An inner surface of the passageway may be configured with facets (e.g., hex cuts) that mate with corresponding facets (e.g., a hex shape) on the outer surface of the breakoff head. In some embodiments, the passageway is disposed substantially centrally within the inner sleeve. However, in other embodiments the cross-sectional shape of the passageway resembles the cross-sectional shape of the breakoff head. For example, the passageway can be "C"-shaped to accommodate a "C"-shaped breakoff head. When the inner sleeve is slid onto the breakoff head, a portion of the inner sleeve is disposed within the central bore of the breakoff head, which beneficially can support and stabilize the breakoff head during the detachment procedure.

The screw head cutter is coupled to a fastener by guiding the cutter onto the breakoff head so that the inner sleeve passes over the breakoff head (as described above). The outer sleeve may be slightly longer than the inner sleeve so that a distal end of the outer sleeve engages the housing of the fastener. Accordingly, the inner sleeve engages the breakoff head, and the outer sleeve engages the housing, so that threes applied to the first and second handles tend to cause a relative rotation of the inner and outer sleeves. The relative rotation exerts a shear stress on the breakoff head, which as described above, fails mechanically at the neck, thereby detaching the breakoff head from the housing. In one technique, the second handle is held firmly so as not to rotate the housing (which is coupled to the vertebral site by the screw portion). A force is applied to the first handle to cause the inner sleeve to rotate and snap off the breakoff head. One technique thereby reduces the transfer of shear stresses to the vertebrae during the detachment procedure. After the breakoff head is detached from the housing, the breakoff head is removed from the patient.

The various devices, methods and techniques described above provide a number of ways to carry out the invention. It is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of the embodiments herein.

Many of the systems, apparatuses, methods, and features described herein can be combined with many of the systems, apparatuses, methods and features disclosed in the following patents and patent applications. The entire disclosure of all of the following patents and patent applications is hereby incorporated by reference herein and made a part of this specification: U.S. Pat. No. 6,361,488 (issued Mar. 26, 2002), U.S. Pat. No. 6,530,880 (issued Mar. 11, 2003), U.S. Pat. No. 6,648,888 (issued Nov. 18, 2003), U.S. Pat. No. 6,652,553 (issued Nov. 25, 2003), U.S. Pat. No. 6,641,583 (issued Nov. 4, 2003), U.S. Pat. No. 6,554,832 (issued. Apr. 29, 2003), U.S. Pat. No. 6,673,074 (issued Jan. 6, 2004), U.S. patent application Ser. No. 09/821,666 (filed Mar. 29, 2001, published Oct. 3, 2002 as Publication No. U.S. 2002/0143328A1), Ser. No. 09/824,411 (filed Apr. 2, 2001, published Oct. 3, 2002 as Publication No. U.S. 2002/0143330A1), Ser. No. 09/921,326 (filed Aug. 2, 2001, published Feb. 6, 2003 as Publication No. U.S. 2003/0028191A1), Ser. No. 09/940,402 (filed Aug. 27, 2001, published Feb. 27, 2003 as Publication No. US 2003/0040656A1), Ser. No. 10/075,668 (filed Feb. 13, 2002, published Aug. 14, 2003 as Publication No. U.S. 2003/0153911A1), Ser. No. 10/087,489 (filed Mar. 1, 2002, published. Sep. 4, 2003 as Publication No. U.S. 2003/0167058A1), Ser. No. 10/178,875 (filed Jun. 24, 2002, published Dec. 25, 2003 as Publication No. U.S. 2003/0236529A1), Ser. No. 10/280,489 (filed Oct. 25, 2002, published Apr. 17, 2003 as Publication No. US 2003/0073998A1), Ser. No. 10/280,799 (filed Oct. 25, 2002), Ser. No. 10/361,887 (filed Feb. 10, 2003, published Aug. 14, 2003 as Publication No. US 2003/0153927A1), Ser. No. 10/658,736 (filed Sep. 9, 2003), Ser. No. 10/678,744 (filed Oct. 2, 2003), Ser. No. 10/693,815 (filed Oct. 24, 2003), Ser. No. 10/693,250 (filed Oct. 24, 2003), Ser. No. 10/693,663 (filed Oct. 24, 2003), Ser. No. 10/842,651 (filed May 10, 2004), Ser. No. 10/845,389 (filed May 13, 2004) U.S. Provisional Applications No. 60/471,431 (filed May 16, 2003), 60/497,763 (filed Aug. 26, 2003), 60/497,822 (filed Aug. 26, 2003), 60/513,796 (filed Oct. 22, 2003), 60/513,013 (filed Oct. 23, 2003), 60/514,559 (filed Oct. 24, 2003), 60/545,587 (filed Feb. 18, 2004), 60/558,296 (filed Mar. 31, 2004), 60/579,643 (filed Jun. 15, 2004).

What is claimed is:

1. A minimally invasive vertebral fixation system, the system comprising:
 a bone anchor including a saddle-shaped housing configured to receive a fixation element;
 a multipurpose tool including an elongate body formed from displaceable opposing elongate arms extended from a cylindrical proximal portion, each arm of the opposing elongate arms including a protrusion extending radially inward from an interior surface engageable with a corresponding recess on an outer surface of the saddle-shaped housing; and a retaining clip including an elongated body with a c-shaped clip portion coupled to a distal end of the elongated body, the c-shaped clip portion configured to receive and constrain the opposing elongate arms of the multipurpose tool from displacing outward when engaging the saddle-shaped housing of the bone anchor when the retaining clip is in a distal position relative to the multipurpose tool, wherein the engagement of the c-shaped clip portion to the opposing elongate arms of the multipurpose tool when the opposing elongate arms are engaged with the bone anchor allows for single-handed insertion of the bone anchor at a target location.

2. The system of claim 1, wherein the opposing elongate arms are spaced apart from each other to define opposing elongated slots configured to receive the fixation element during insertion into the saddle-shaped housing.

3. The system of claim 2, wherein the opposing elongate arms and the opposing elongate slots are symmetrically disposed about the perimeter of the elongate body of the multipurpose tool.

4. The system of claim 3, wherein the width of each slot of the opposing elongate slots is less than the width of each arm of the opposing elongate arms.

5. The system of claim 1, wherein each arm of the opposing elongate arms includes an arcuate cross-section corresponding to the cylindrical proximal portion of the elongate body of the multipurpose tool, and wherein the c-shaped clip portion includes an arcuate cross-section corresponding to the opposing elongate arms.

6. The system of claim 5, wherein the c-shaped clip portion includes a cross-sectional diameter sized to produce a friction fit when slid over the elongate body of the multipurpose tool.

7. The system of claim 1, wherein the retaining clip includes a handle disposed on a proximal end, the handle comprising a tab set in an offset or orthogonal orientation to the elongated body of the retaining clip and adapted for use in pushing or pulling on the retaining clip.

8. The system of claim 1, further comprising an anti-torque handle including a central ring portion adapted to interface with the cylindrical proximal portion of the multipurpose tool.

9. The system of claim 8, wherein the cylindrical proximal portion includes external facets distributed around the perimeter, and the central ring portion includes corresponding internal facets distributed around an internal surface to interface with the external facets on the cylindrical proximal portion.

10. A multipurpose tool for use with a pedicle screw in a spinal fixation system, the multipurpose tool comprising:

an elongate body formed from opposing elongate arms extended from a cylindrical proximal portion, each arm of the opposing elongate arms including a protrusion extending radially inward from an interior surface and configured to engage a corresponding recess on an outer surface of a U-shaped housing of the pedicle screw; and a retaining clip including an elongated body with a c-shaped clip portion positioned at a distal end of the retaining clip, the c-shaped clip portion configured to receive and constrain the opposing elongate arms of the elongate body when the retaining clip is in a distal position relative to the elongate body.

11. The system of claim 10, wherein the opposing elongate arms are spaced apart from each other to define opposing elongated slots configured to receive a fixation element during insertion into the U-shaped housing.

12. The system of claim 11, wherein the opposing elongate arms and the opposing elongate slots are symmetrically disposed about the perimeter of the elongate body.

13. The system of claim 12, wherein the width of each slot of the opposing elongate slots is less than the width of each arm of the opposing elongate arms.

14. The system of claim 10, wherein each arm of the opposing elongate arms includes an arcuate cross-section corresponding to the cylindrical proximal portion of the elongate body of the multipurpose tool, and wherein the c-shaped clip portion includes an arcuate-cross-section corresponding to the opposing elongate arms.

15. The system of claim 14, wherein the c-shaped clip portion includes a cross-sectional diameter sized to produce a friction fit when slid over the elongate body of the multipurpose tool.

16. The system of claim 10, wherein the retaining clip includes a handle disposed on a proximal end, the handle comprising a tab set in an offset or orthogonal orientation to the elongated body of the retaining clip and adapted for use in pushing or pulling on the retaining clip.

17. The system of claim 10, further comprising an anti-torque handle including a central ring portion adapted to interface with the cylindrical proximal portion of the multipurpose tool, wherein the interfacing of the anti-torque handle with the multipurpose tool when the opposing elongate arms are engaged with the pedicle screw allows for single-handed insertion of the pedicle screw at a target location.

18. The system of claim 17, wherein the cylindrical proximal portion includes external facets distributed around the circumference, and the central ring portion includes corresponding internal facets distributed around an internal surface to interface with the external facets on the cylindrical proximal portion.

19. A method for minimally invasive vertebral fixation, comprising:

engaging a bone anchor with displaceable opposing elongate arms extending from a cylindrical proximal portion of an elongate body of a multipurpose tool, each arm of the opposing elongate arms including a protrusion extending radially inward from an interior surface engageable with a corresponding recess on an outer surface of a saddle-shaped housing, of the bone anchor the saddle-shaped housing configured to receive a fixation element;

engaging the elongate body of the multipurpose tool with a retaining clip including an elongated body with a c-shaped clip portion at a distal end of the elongated body;

displacing the retaining clip to a distal position relative to the multipurpose tool, wherein the c-shaped clip portion is configured to receive and constrain the opposing elongate arms of the multipurpose tool from displacing outward when engaging the saddle-shaped housing of the bone anchor when the retaining clip is in the distal position relative to the multipurpose tool, and wherein the engagement of the c-shaped clip portion to the opposing elongate arms of the multipurpose tool when the opposing elongate arms are engaged with the bone anchor allows for single-handed insertion of the bone anchor at a target location.

20. The method of claim 19, wherein the retaining clip includes a handle disposed on a proximal end, the handle comprising a tab set in an offset or orthogonal orientation to the elongated body of the retaining clip and adapted for use in pushing or pulling on the retaining clip.

* * * * *